US011133084B2

(12) United States Patent
Schnall-Levin et al.

(10) Patent No.: US 11,133,084 B2
(45) Date of Patent: *Sep. 28, 2021

(54) SYSTEMS AND METHODS FOR NUCLEIC ACID SEQUENCE ASSEMBLY

(71) Applicant: 10X Genomics, Inc., Pleasanton, CA (US)

(72) Inventors: Michael Schnall-Levin, San Francisco, CA (US); Iain MacCallum, Cambridge, MA (US)

(73) Assignee: 10X GENOMICS, INC., Pleasanton, CA (US)

(*) Notice: Subject to any disclaimer, the term of this patent is extended or adjusted under 35 U.S.C. 154(b) by 1000 days.

This patent is subject to a terminal disclaimer.

(21) Appl. No.: 15/801,868

(22) Filed: Nov. 2, 2017

(65) Prior Publication Data
US 2018/0165411 A1    Jun. 14, 2018

Related U.S. Application Data

(63) Continuation of application No. 14/752,773, filed on Jun. 26, 2015, now Pat. No. 10,839,939.

(60) Provisional application No. 62/017,589, filed on Jun. 26, 2014.

(51) Int. Cl.
*G16B 30/00* (2019.01)
*G16B 45/00* (2019.01)

(52) U.S. Cl.
CPC ............. *G16B 30/00* (2019.02); *G16B 45/00* (2019.02)

(58) Field of Classification Search
None
See application file for complete search history.

(56) References Cited

U.S. PATENT DOCUMENTS

| | | |
|---|---|---|
| 5,149,625 A | 9/1992 | Church et al. |
| 5,202,231 A | 4/1993 | Drmanac et al. |
| 5,413,924 A | 5/1995 | Kosak et al. |
| 5,436,130 A | 7/1995 | Mathies et al. |
| 5,512,131 A | 4/1996 | Kumar et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,736,330 A | 4/1998 | Fulton |
| 5,834,197 A | 11/1998 | Parton |
| 5,851,769 A | 12/1998 | Gray et al. |
| 5,856,174 A | 1/1999 | Lipshutz et al. |
| 5,958,703 A | 9/1999 | Dower et al. |
| 5,994,056 A | 11/1999 | Higuchi |
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |
| 6,143,496 A | 11/2000 | Brown et al. |
| 6,172,218 B1 | 1/2001 | Brenner |
| 6,297,006 B1 | 10/2001 | Drmanac et al. |
| 6,297,017 B1 | 10/2001 | Thompson |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,406,848 B1 | 6/2002 | Bridgham et al. |
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,913,935 B1 | 7/2005 | Thomas |
| 6,929,859 B2 | 8/2005 | Chandler et al. |
| 6,969,488 B2 | 11/2005 | Bridgham et al. |

(Continued)

FOREIGN PATENT DOCUMENTS

| | | |
|---|---|---|
| EP | 0249007 A2 | 12/1987 |
| EP | 0637996 B1 | 7/1997 |

(Continued)

OTHER PUBLICATIONS

Fredrickson, C.K. et al., "Macro-to-micro interfaces for microfluidic devices" Lab Chip (2004) 4:526-533.
Freiberg, et al. "Polymer microspheres for controlled drug release" Int J Pharm. Sep. 10, 2004;282(1-2):1-18.
Fu. A.Y. et al. "A microfabricated fluorescence-activated cell sorter" Nature Biotech (Nov. 1999) 17:1109-1111.
Fulton et al., "Advanced multiplexed analysis with the FlowMetrix system" Clin Chem. Sep. 1997;43(9): 1749-56.
Garstecki, P. et al. "Formation of monodisperse bubbles in a microfluidic flow-focusing device" Appl. Phys. Lett (2004) 85(13):2659-2651. DOI: 10.1063/1.1796526.
Gartner, et al. The Microfluidic Toolbox: examples for fluidic interfaces and standardization concepts. Proc. SPIE 4982, Microfluidics, BioMEMS, and Medical Microsystems, (Jan. 17, 2003); doi: 10.1117/12.479566.

(Continued)

Primary Examiner — Joseph Woitach

(57) ABSTRACT

Determination of a nucleic acid sequence using sequence reads of the nucleic acid. The reads, in sets of reads, include a first portion for a subset of the nucleic acid and a common second portion identifying a reaction partition that formed the read, where the partition has the subset of the nucleic acid in the form of a fragment. A set of k-mers is created for a read, with identifiers of the source reads for each k-mer are retained. The k-mers are used to determine whether to derive a contig sequence representative of the nucleic acid, where the contig comprises an origin node comprising a first set of overlapping k-mers and one of a first destination node comprising a second set of overlapping k-mers and a second destination node comprising a third set of overlapping k-mers. The sequence of the nucleic acid is assembled using at least the contig.

20 Claims, 25 Drawing Sheets

Specification includes a Sequence Listing.

(56) References Cited

U.S. PATENT DOCUMENTS

| | | |
|---|---|---|
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,323,305 B2 | 1/2008 | Leamon et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 | 5/2010 | Stone et al. |
| 7,709,197 B2 | 5/2010 | Drmanac |
| 7,745,178 B2 | 6/2010 | Dong |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,067,159 B2 | 11/2011 | Brown et al. |
| 8,133,719 B2 | 3/2012 | Drmanac et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,337,778 B2 | 12/2012 | Stone et al. |
| 8,592,150 B2 | 11/2013 | Drmanac et al. |
| 8,603,749 B2 | 12/2013 | Gillevet |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,871,444 B2 | 10/2014 | Griffiths et al. |
| 8,889,083 B2 | 11/2014 | Ismagilov et al. |
| 9,012,370 B2 | 4/2015 | Hong |
| 9,017,948 B2 | 4/2015 | Agresti et al. |
| 9,029,083 B2 | 5/2015 | Griffiths et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,694,361 B2 | 7/2017 | Bharadwaj et al. |
| 9,695,468 B2 | 7/2017 | Hindson et al. |
| 9,824,068 B2 | 11/2017 | Wong et al. |
| 10,119,167 B2 | 11/2018 | Srinivasan et al. |
| 10,221,442 B2 | 3/2019 | Hindson et al. |
| 10,395,758 B2 | 8/2019 | Schnall-Levin |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0051992 A1 | 5/2002 | Bridgham et al. |
| 2002/0089100 A1 | 7/2002 | Kawasaki |
| 2002/0092767 A1 | 7/2002 | Bjornson et al. |
| 2002/0179849 A1 | 12/2002 | Maher |
| 2003/0008285 A1 | 1/2003 | Fischer |
| 2003/0008323 A1 | 1/2003 | Ravkin et al. |
| 2003/0027221 A1 | 2/2003 | Scott et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0104466 A1 | 6/2003 | Knapp et al. |
| 2003/0108897 A1 | 6/2003 | Drmanac |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0111241 A1 | 5/2007 | Cereb et al. |
| 2007/0154903 A1 | 7/2007 | Marla et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0213766 A1 | 9/2008 | Brown et al. |
| 2008/0241820 A1 | 10/2008 | Krutzik et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0118488 A1 | 5/2009 | Drmanac et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kum |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0069263 A1 | 3/2010 | Shendure et al. |
| 2010/0105112 A1 | 4/2010 | Holtze et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston et al. |
| 2010/0210479 A1 | 8/2010 | Griffiths et al. |
| 2010/0216153 A1 | 8/2010 | Lapidus et al. |
| 2011/0033854 A1 | 2/2011 | Drmanac et al. |
| 2011/0053798 A1 | 3/2011 | Hindson et al. |
| 2011/0071053 A1 | 3/2011 | Drmanac et al. |

(56) References Cited

U.S. PATENT DOCUMENTS

| | | |
|---|---|---|
| 2011/0086780 A1 | 4/2011 | Colston et al. |
| 2011/0092376 A1 | 4/2011 | Colston et al. |
| 2011/0092392 A1 | 4/2011 | Colston et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0041727 A1 | 2/2012 | Mishra et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0196288 A1 | 8/2012 | Beer |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0230338 A1 | 9/2012 | Ganeshalingam et al. |
| 2012/0309002 A1 | 12/2012 | Link |
| 2012/0316074 A1 | 12/2012 | Saxonov |
| 2013/0028812 A1 | 1/2013 | Prieto et al. |
| 2013/0046030 A1 | 2/2013 | Rotem et al. |
| 2013/0078638 A1 | 3/2013 | Berka et al. |
| 2013/0079231 A1 | 3/2013 | Pushkarev et al. |
| 2013/0109575 A1 | 5/2013 | Kleinschmidt et al. |
| 2013/0130919 A1 | 5/2013 | Chen et al. |
| 2013/0157870 A1 | 6/2013 | Pushkarev et al. |
| 2013/0157899 A1 | 6/2013 | Adler et al. |
| 2013/0178368 A1 | 7/2013 | Griffiths et al. |
| 2013/0185096 A1 | 7/2013 | Giusti et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0225418 A1 | 8/2013 | Watson |
| 2013/0268206 A1 | 10/2013 | Porreca et al. |
| 2013/0274117 A1 | 10/2013 | Church et al. |
| 2013/0311106 A1 | 11/2013 | White et al. |
| 2013/0317755 A1 | 11/2013 | Mishra et al. |
| 2014/0057799 A1 | 2/2014 | Johnson et al. |
| 2014/0065234 A1 | 3/2014 | Shum et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0200166 A1 | 7/2014 | Rooyen et al. |
| 2014/0206554 A1 | 7/2014 | Hindson et al. |
| 2014/0214334 A1 | 7/2014 | Plattner et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0323316 A1 | 10/2014 | Drmanac et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0066385 A1 | 3/2015 | Schnall-Levin et al. |
| 2015/0111256 A1 | 4/2015 | Church et al. |
| 2015/0133344 A1 | 5/2015 | Shendure et al. |
| 2015/0218633 A1 | 8/2015 | Hindson et al. |
| 2015/0220532 A1 | 8/2015 | Wong |
| 2015/0224466 A1 | 8/2015 | Hindson et al. |
| 2015/0225777 A1 | 8/2015 | Hindson et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0232291 A1 | 8/2016 | Kyriazopoulou-Panagiotopoulou et al. |
| 2016/0304860 A1 | 10/2016 | Hindson et al. |
| 2016/0350478 A1 | 12/2016 | Chin et al. |
| 2017/0235876 A1 | 8/2017 | Jaffe et al. |
| 2018/0196781 A1 | 7/2018 | Wong |
| 2018/0265928 A1 | 9/2018 | Schnall-Levin et al. |

FOREIGN PATENT DOCUMENTS

| | | |
|---|---|---|
| EP | 1019496 B1 | 9/2004 |
| EP | 1482036 B1 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| GB | 2485850 A | 5/2012 |
| JP | 5949832 A | 3/1984 |
| JP | 2006507921 A | 3/2006 |
| JP | 2006289250 A | 10/2006 |
| JP | 2007-193708 A | 8/2007 |
| JP | 2007268350 A | 10/2007 |
| JP | 2009208074 | 9/2009 |
| RU | 2321638 C2 | 4/2008 |
| WO | 1996029629 A2 | 9/1996 |
| WO | 1996041011 A1 | 12/1996 |
| WO | 1999009217 A1 | 2/1999 |
| WO | 1999052708 A1 | 10/1999 |
| WO | 2000008212 A1 | 2/2000 |
| WO | 2000026412 A1 | 5/2000 |
| WO | 2001014589 A2 | 3/2001 |
| WO | 2001089787 A2 | 11/2001 |
| WO | 2002031203 A2 | 4/2002 |
| WO | 2002086148 A1 | 10/2002 |
| WO | 2004002627 A2 | 1/2004 |
| WO | 2004010106 A2 | 1/2004 |
| WO | 2004069849 A2 | 8/2004 |
| WO | 2004091763 A2 | 10/2004 |
| WO | 2004102204 A1 | 11/2004 |
| WO | 2004103565 A2 | 12/2004 |
| WO | 2004105734 A1 | 12/2004 |
| WO | 2005002730 A1 | 1/2005 |
| WO | 2005021151 A1 | 3/2005 |
| WO | 2005023331 A2 | 3/2005 |
| WO | 2005040406 A1 | 5/2005 |
| WO | 2005049787 A9 | 6/2005 |
| WO | 2005082098 A2 | 9/2005 |
| WO | 2006030993 A1 | 3/2006 |
| WO | 2006078841 A1 | 7/2006 |
| WO | 2006096571 A2 | 9/2006 |
| WO | 2007001448 A2 | 1/2007 |
| WO | 2007002490 A2 | 1/2007 |
| WO | 2007024840 A2 | 3/2007 |
| WO | 2007081385 A2 | 7/2007 |
| WO | 2007081387 A1 | 7/2007 |
| WO | 2007089541 A2 | 8/2007 |
| WO | 2007114794 A1 | 10/2007 |
| WO | 2007121489 A2 | 10/2007 |
| WO | 2007133710 A2 | 11/2007 |

(56) References Cited

FOREIGN PATENT DOCUMENTS

| | | | |
|---|---|---|---|
| WO | 2007138178 | A2 | 12/2007 |
| WO | 2007140015 | A2 | 12/2007 |
| WO | 2007149432 | A2 | 12/2007 |
| WO | 2008021123 | A1 | 2/2008 |
| WO | 2008091792 | A2 | 7/2008 |
| WO | 2008102057 | A1 | 8/2008 |
| WO | 2008109176 | A2 | 9/2008 |
| WO | 2008121342 | A2 | 10/2008 |
| WO | 2008134153 | A1 | 11/2008 |
| WO | 2007139766 | A3 | 12/2008 |
| WO | 2009005680 | A1 | 1/2009 |
| WO | 2009011808 | A1 | 1/2009 |
| WO | 2009023821 | A1 | 2/2009 |
| WO | 2009061372 | A1 | 5/2009 |
| WO | 2009085215 | A1 | 7/2009 |
| WO | 2010004018 | A2 | 1/2010 |
| WO | 2010033200 | A2 | 3/2010 |
| WO | 2010115154 | A1 | 10/2010 |
| WO | 2010126614 | A2 | 11/2010 |
| WO | 2010127304 | A2 | 11/2010 |
| WO | 2010148039 | A2 | 12/2010 |
| WO | 2010151776 | A2 | 12/2010 |
| WO | 2011047870 | A1 | 4/2011 |
| WO | 2011056546 | A1 | 5/2011 |
| WO | 2011066476 | A1 | 6/2011 |
| WO | 2011074960 | A1 | 6/2011 |
| WO | 2012012037 | A1 | 1/2012 |
| WO | 2012048341 | A1 | 4/2012 |
| WO | 2012055929 | A1 | 5/2012 |
| WO | 2012061832 | A1 | 5/2012 |
| WO | 2012100216 | A2 | 7/2012 |
| WO | 2012083225 | A3 | 8/2012 |
| WO | 2012106546 | A2 | 8/2012 |
| WO | 2012112804 | A1 | 8/2012 |
| WO | 2012116331 | A2 | 8/2012 |
| WO | 2012142531 | A2 | 10/2012 |
| WO | 2012142611 | A2 | 10/2012 |
| WO | 2012149042 | A2 | 11/2012 |
| WO | 2012166425 | A2 | 12/2012 |
| WO | 2013035114 | A1 | 3/2013 |
| WO | 2013055955 | A1 | 4/2013 |
| WO | 2013123125 | A1 | 8/2013 |
| WO | 2013177220 | A1 | 11/2013 |
| WO | 2014028537 | A1 | 2/2014 |
| WO | 2014093676 | A1 | 6/2014 |
| WO | 2015157567 | A1 | 10/2015 |
| WO | 2015200891 | A1 | 12/2015 |
| WO | 2016130578 | A1 | 8/2016 |

OTHER PUBLICATIONS

Ghadessy, et al. Directed evolution of polymerase function by compartmentalized self-replication. Proc Natl Acad Sci U S A. Apr. 10, 2001;98(8):4552-7. Epub 2001 Mar. 27, 2001.
Gonzalez, et al. The influence of CCL3L1 gene-containing segmental duplications on HIV-1/AIDS susceptibility. Science. Mar. 4, 2005;307(5714)1434-40. Epub Jan. 6, 2005.
Gordon et al. "Consed: A Graphical Tool for Sequence Finishing," Genome Research (1998) 8:198-202.
Granieri, Lucia "Droplet-based microfluidics and engineering of tissue plasminogen activator for biomedical applications" Ph.D. Thesis, Nov. 13, 2009 (131 pages).
Grasland-Mongrain, E. et al. "Droplet coalescence in microfluidic devices" Internet Citation, 2003, XP002436104, Retrieved from the Internet: URL:http://www.eleves.ens.fr/home/grasland/rapports/stage4.pdf [retrieved on Jun. 4, 2007].
Guo, M.T. et al., "Droplet microfluidics for high-throughput biological assays" Lab Chip (2012) 12:2146-2155.
Gyarmati et al., "Reversible Disulphide Formation in Polymer Networks: A Versitile Functional Group from Synthesis to Application," European Polymer Journal, 2013, 49, 1268-1286.

Hashimshony, T et al. "CEL-Seq: Single-Cell RNa-Seq by Multiplexed Linear Amplification" Cell Rep. Sep. 27, 2012;2(3):666-73. doi: 10.1016/j.celrep.2012.08.003. Epub Aug. 30, 2012.
He "Selective Encapsulation of Single Cells and Subcellular Organelles into Picoliter- and Femtoliter-Volume Droplets" Anal. Chem 77: 1539-1544 (2005).
Heng et al. "Fast and accurate long-read alignment with Burrows-Wheeler transform," Bioinformatics (2010) 25(14): 1754-1760.
Holtze, C. et al. Biocompatible surfactants for water-in-fluorocarbon emulsions. Lab Chip. Oct. 2008;8(10):1632-9. doi: 10.1039/b806706f. Epub Sep. 2, 2008.
Huang et al. "EagleView: A genome assembly viewer for next-generationsequencing technologies," Genome Research (2008) 18:1538-1543.
Huebner, "Quantitative detection of protein expression in single cells using droplet microfluidics", Chem. Commun. 1218-1220 (2007).
Hug, H. et al. "Measurement of the number of molecules of a single mRNA species in a complex mRNA preparation" J Theor Biol. Apr. 21, 2003;221(4):615-24.
Jena et al., "Cyclic olefin copolymer based microfluidic devices for biochip applications: Ultraviolet surface grafting using 2-methacryloyloxyethyl phosphorylchloline" Biomicrofluidics (Mar. 15, 2012) 6:012822 (12 pages).
Jung, W-C et al., "Micromachining of injection mold inserts for fluidic channel of polymeric biochips" Sensors (2007) 1:1643-1654.
Kanehisa et al. "KEGG: Kyoto Encyclopedia of Genes and Genomes," Nucleic Acids Research (2000) 28:27-30.
Khomiakov A et al., "Analysis of perfect and mismatched DNA duplexes by a generic hexanucleotide microchip". Mol Bioi (Mosk). Jul.-Aug. 2003;37(4):726-41. Russian. Abstract only.
Kim et al. "HapEdit: an accuracy assessment viewer for haplotype assembly using massively parallel DNA-sequencing technologies," Nucleic Acids Research (2011) pp. 1-5.
Kim, et al. Albumin loaded microsphere of amphiphilic poly(ethylene glycol)/ poly(alpha-ester) multiblock copolymer. Eur J Pharm Sci. Nov. 2004;23(3):245-51.
Kim, et al. Fabrication of monodisperse gel shells and functioNal microgels in microfluidic devices. Angew Chem Int Ed Engl. 2007;46(11):1819-22.
Kim, J et al., "Rapid prototyping of microfluidic systems using a PDMS/polymer tape composite" Lab Chip (2009) 9:1290-1293.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Klein, et al. Droplet barcoding for single-cell transcriptomics applied to embryonic stem cells. Cell. May 21, 2015; 161:1187-1201.
Knight, et al. Subtle chromosomal rearrangements in children with unexplained mental retardation. Lancet. Nov. 13, 1999;354(9191):1676-81.
Koster et al., "Drop-based microfluidic devices for encapsulation of single cells", Lab on a Chip The Royal Soc. of Chem. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Lagus, T.P. et al., "A review of the theory, methods and recent applications of high-throughput single-cell droplet microfluidics" J. Phys. D: Appl. Phys. (2013) 46:114005 (21 pages).
Layer et al. "LUMPY: A probabilistic framework for structural variant discovery," Genome Biology (2014) 15(6):R84.
Li, Y. et al., "PEGylated PLGA Nanoparticles as protein carriers: synthesis, preparation and biodistribution in rats," Journal of Controlled Release, vol. 71, pp. 203-211 (2001).
Lippert et al. "Algorithmic strategies for the single nucleotide polymorphism haplotype assembly problem," Brief. Bionform (2002) 3:23-31.

(56) References Cited

OTHER PUBLICATIONS

Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24(6):703-707 (Jun. 2006).
Lowe, Adam J."Norbornenes and [n]polynorbornanes as molecular scaffolds for anion recognition" Ph.D. Thesis (May 2010). (361 pages).
Lupski. Genomic rearrangements and sporadic disease. Nat Genet. Jul. 2007;39(7 Suppl):S43-7.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, D.A. et al., "Injection molded microfluidic chips featuring integrated interconnects" Lab Chip (2006) 6:1346-1354.
Makino, K. et al. "Preparation of hydrogel microcapsules Effects of preparation conditions upon membrane properties" Colloids and Surfaces: B Biointerfaces (1998) 12:97-104.
"SSH Tunnel—Local and Remote Port Forwarding Explained With Examples," Trackets Blog, http://blog.trackets.aom/2014/05/17/ssh-tunnel-local-and-remote-port-forwarding-explained-with-examples.html; Retrieved from the Internet Jul. 7, 2016.
Abate et al., Valve-based flow focusing for drop formation. Appl Phys Lett. 2009;94. 3 pages.
Abate, A.R. et al. "Beating Poisson encapsulation statistics using close-packed ordering" Lab on a Chip (Sep. 21, 2009) 9(18):2628-2631.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Biol., 329:196-205 (2006).
Akselband, "Rapid mycobacteria drug susceptibility testing using gel microdrop (GMD) growth assay and flow cytometry", J. Microbiol. Methods, 62:181-197 (2005).
Anna et al., "Formation of dispersions using 'flow focusing' in microchannels", Appln. Phys. Letts. 82:3 364 (2003).
Attia, U.M et al., "Micro-injection moulding of polymer microfluidic devices" Microfluidics and nanofluidics (2009) 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.
Bansal et al. "An MCMC algorithm for haplotype assembly from whole-genome sequence data," (2008) Genome Res 18:1336-1346.
Bansal et al. "HapCUT: an efficient and accurate algorithm for the haplotype assembly problem," Bioinformatics (2008) 24:1153-1159.
Baret et al. "Fluorescence-activated droplet sorting (FADS): efficient microfluidic cell sorting based on enzymatic activity" Lab on a Chip (2009) 9(13):1850-1858.
Bentley et al. "Accurate whole human genome sequencing using reversible terminator chemistry," (2008) Nature 456:53-59.

Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Bransky, et al. A microfluidic droplet generator based on a piezoelectric actuator. Lab Chip. Feb. 21, 2009;(4):516-20. doi: 10.1039/b814810d. Epub Nov. 20, 2008.
Bray, "The JavaScript Object Notation (JSON) Data Interchange Format," Mar. 2014, retrieved from the Internet Feb. 15, 2015; https://tools.iett.org/html/rfc7159.
Brouzes, E et al., "Droplet microfluidic technology for single-cell high-throughput screening" PNAS (2009) 106 (34):14195-14200.
Browning, S.R. et al. "Haplotype Phasing: Existing Methods and New Developments" NaRevGenet (Sep. 16, 2011) 12(10):703-714.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Chaudhary "A rapid method of cloning functional variable-region antibody genes in *Escherichia coli* as single-chain Immunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;I8(1):83-101.
Chen et al. "BreakDancer: an algorithm for high-resolution mapping of genomic structural variation," Nature Methods (2009) 6(9):677-681.
Chen, F. et al. "Chemical transfection of cells in picoliter aqueous droplets in fluorocarbon oil" Anal Chem (2011) 83(22):8816-8820.
Choi et al. "Identification of novel isoforms of the EML4-ALK transforming gene in non-small cell lung cancer," Cancer Res (2008) 68:4971-4976.
Chokkalingam, V et al., "Probing cellular heterogeneity in cytokine-secreting immune cells using droplet-based microfluidics" Lab Chip (2013) 13:4740-4744.
Chou, H-P. et al. "Disposable Microdevices for DNA Analysis and Cell Sorting" Proc. Solid-State Sensor and Actuator Workshop Hilton Head, SC Jun. 8-11, 1998, pp. 11-14.
Chu, L-Y. et al., "Controllable monodisperse multiple emulsions" Angew. Chem. Int. Ed. (2007) 46:8970-8974.
Clausell-Tormos et al., "Droplet-based microfluidic platforms for the encapsulation and screening of mammalian cells and multicellular organisms", Chem. Biol. 15:427-437 (2008).
Cleary et al. "Joint variant and de novo mutation identification on pedigrees from highthroughput sequencing data," J Comput Biol (2014) 21:405-419.
Cook, et al. Copy-number variations associated with neuropsychiatric conditions. Nature. Oct. 16, 2008;455 (7215):919-23. doi: 101038/nature07458.
De Bruin et al., UBS Investment Research. Q-Series?: DNa Sequencing. UBS Securities LLC. Jul. 12, 2007. 15 pages.
Demirci, et al. "Single cell epitaxy by acoustic picolitre droplets" Lab Chip. Sep. 2007;7(9):1139-45. Epub Jul. 10, 2007.
Doerr, "The smallest bioreactor", Nature Methods, 2:5 326 (2005).
Dowding, et al. "Oil core/polymer shell microcapsules by internal phase separation from emulsion droplets. II:controlling the release profile of active molecules" Langmuir. Jun. 7, 2005;21(12):5278-84.
Draper, M.C. et al., "Compartmentalization of electrophoretically separated analytes in a multiphase microfluidic platform" Anal. Chem. (2012) 84:5801-5808.
Dressler, O.J. et al., "Droplet-based microfluidics enabling impact on drug discovery" J. Biomol. Screen (2014) 19(4):483-496.
Drmanac et al., Sequencing by hybridization (SBH): advantages, achievements, and opportunities. Adv Biochem Eng Biotechnol. 2002;77 :75-101.

(56) References Cited

OTHER PUBLICATIONS

Eastburn, D.J. et al., "Ultrahigh-throughput mammalian single-cell reverse-transcriptase polymerase chain reaction in microfluidic droplets" Anal. Chem. (2013) 85:8016-8021.

Eid et al. "Real-time sequencing form single polymerase molecules," Science (2009) 323:133-138.

Ekblom, R. et al. "A field guide to whole-genome sequencing, assembly and annotation" Evolutionary Apps (Jun. 24, 2014) 7(9):1026-1042.

Esser-Kahn, et al. Triggered release from polymer capsules. Macromolecules. 2011; 44:5539-5553.

Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.

Fisher, S. et al. "A Scalable, fully automated process for construction of sequence-ready human exome targeted capture libraries" Genome Biology (2011) 2:R1-R15. doi: 10.1186/gb-2011-12-1-r1. Epub Jan. 4, 2011.

Marcus. Gene method offers diagnostic hope. The Wall Street Journal. Jul. 11, 2012.

Margulies et al. "Genome sequencing in microfabricated high-density picoliter reactors," Nature (2005) 437:376-380.

Matochko, W.L. et al., "Uniform amplification of phage display libraries in monodisperse emulsions," Methods (2012) 58:18-27.

Mazutis, et al. Selective droplet coalescence using microfluidic systems. Lab Chip. Apr. 24, 2012;12(10):1800-6. doi: 10.1039/c2lc40121e. Epub Mar. 27, 2012.

McKenna et al. "The Genome Analysis Toolkit: A MapReduce framework for anaylzing nextgeneration DNA sequencing data," Genome Research (2010) pp. 1297-1303.

Merriman, et al. Progress in ion torrent semiconductor chip based sequencing. Electrophoresis. Dec. 2012;33(23):3397-3417. doi: 10.1002/elps.201200424.

Miller et al. "Assembly Algorithms for next-generation sequencing data," Genomics, 95 (2010), pp. 315-327.

Mirzabekov, "DNA Sequencing by Hybridization—a Megasequencing Method and a Diagnostic Tool?" Trends in Biotechnology 12(1): 27-32 (1994).

Moore, J.L. et al., "Behavior of capillary valves in centrifugal microfluidic devices prepared by three-dimensional printing" Microfluid Nanofluid (2011) 10:877-888.

Mouritzen et al., Single nucleotide polymorphism genotyping using locked nucleic acid (LNa). Expert Rev Mol Diagn. Jan. 2003;3(1):27-38.

Myllykangas et al. "Efficient targeted resequencing of human germline and cancer genomes by oligonucleotide-selective sequencing," Nat Biotechnol, (2011) 29:1024-1027.

Nagashima, S. et al. "Preparation of monodisperse poly(acrylamide-co-acrylic acid) hydrogel microspheres by a membrane emulsification technique and their size dependent surface properties" Colloids and Surfaces: B Biointerfaces (1998) 11:47-56.

Navin, N.E. "The first five years of single-cell cancer genomics and beyond" Genome Res. (2015) 25:1499-1507.

Nguyen, et al. In situ hybridization to chromosomes stabilized in gel microdrops. Cytometry. 1995; 21:111-119.

Novak, R. et al., "Single cell multiplex gene detection and sequencing using microfluidicallygenerated agarose emulsions" Angew. Chem. Int. Ed. Engl. (2011) 50(2):390-395.

Oberholzer, et al. Polymerase chain reaction in liposomes. Chem Biol. Oct. 1995;2(10):677-82.

Ogawa, et al. Production and characterization of O/W emulsions containing cationic droplets stabilized by lecithin-ahitosan membranes. J Agric Food Chem. Apr. 23, 2003;51(9):2806-12.

Okushima, "Controlled production of monodisperse double emulsions by two-step droplet breakup in microfluidic levices", Langmuir, 20:9905-9908 (2004).

Perez, C., et al., "Poly(lactic acid)-poly(ethylene glycol) Nanoparticles as new carriers for the delivery ofplasmid DNa," Journal of Controlled Release, vol. 75, pp. 211-224 (2001).

Peters et al., "Accurate whole-genome sequencing and haplotyping from 10 to 20 human cells," Nature, Jul. 12, 2012, vol. 487, pp. 190-195.

Pinto, et al. Functional impact of global rare copy number variation in autism spectrum disorders. Nature. Jul. 15, 2010;466(7304):368-72. doi: 10.1038/nature09146. Epub Jun. 9, 2010.

Plunkett, et al. Chymotrypsin responsive hydrogel: application of a disulfide exchange protocol for the preparation of methacrylamide containing peptides. Biomacromolecules. Mar.-Apr. 2005;6(2):632-7.

Pushkarev et al. "Single-molecule sequencing of an individual human genome," Nature Biotech (2009) 17:847-850.

Ropers. New perspectives for the elucidation of genetic disorders. Am J Hum Genet. Aug. 2007;81(2):199-207. Epub Jun. 29, 2007.

Rotem, A. et al. "Single Cell Chip-Seq Using Drop-Based Microfluidics" Abstract #50. Frontiers of Single Cell Analysis, Stanford University Sep. 5-7, 2013.

Rotem, A. et al., "High-throughput single-cell labeling (Hi-SCL) for RNA-seq using drop-based microfluidics" PLOS One (May 22, 2015) 0116328 (14 pages).

Ryan, et al. Rapid assay for mycobacterial growth and antibiotic susceptibility using gel microdrop encapsulation. J Clin Microbiol. Jul. 1995;33(7):1720-6.

Schirinzi et al., Combinatorial sequencing-by-hybridization: analysis of the NF1 gene. Genet Test. 2006 Spring;10(1):8-17.

Schmitt, "Bead-based multiplex genotyping of human papillomaviruses", J. Clinical Microbiol., 44:2 504-512 (2006).

Sebat, et al. Strong association of de novo copy number mutations with autism. Science. Apr. 20, 2007;316(5823):445-9. Epub Mar. 15, 2007.

Seiffert, S. et al., "Smart microgel capsules from macromolecular precursors" J. Am. Chem. Soc. (2010)132:6606-6609.

Shah, "Fabrication of mono disperse thermosensitive microgels and gel capsules in micro fluidic devices", Soft Matter, 4:2303-2309 (2008).

Shendure et al. "Accurate Multiplex Polony Sequencing of an Evolved bacterial Genome" Science (2005) 309:1728-1732.

Shimkus et al. "A chemically cleavable biotinylated nucleotide: Usefulness in the recovery of protein-DNA complexes from avidin affinity columns" PNAS (1985) 82:2593-2597.

Shlien, et al. Copy number variations and cancer. Genome Med. Jun. 16, 2009;1(6):62. doi: 10.1186/gm62.

Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.

Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.

Sorokin et al., Discrimination between perfect and mismatched duplexes with oligonucleotide gel microchips: role of thermodyNamic and kinetic effects during hybridization. J Biomol Struct Dyn. Jun. 2005;22(6):725-34.

Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).

Sun et al., Progress in research and application of liquid-phase chip technology. Chinese Journal Experimental Surgery. May 2005;22(5):639-40.

Tawfik, D.S. et al. "Man-made cell-like compartments for molecular evolution" Nature Biotech (Jul. 1998) 16:652-656.

Tewhey et al. "The importance of phase information for human genomics," Nat Rev Genet (2011) 12:215-223.

Tewhey, R. et al., "Microdroplet-based PCR enrichment for large-scale targeted sequencing" Nature Biotech. (2009) 27(11)1025-1031 and Online Methods (11 pages).

Theberge, A.B, et al. Microdropelts in microfluidics: an evolving platform for discoveries in chemsitry and biology. Angew Chem Int Ed Engl. Aug. 9, 2010;49(34):5846-68. doi: 10.1002/anie.200906653.

(56) References Cited

OTHER PUBLICATIONS

Tonelli, C. et al., "Perfluoropolyether functional oligomers: unusual reactivity in organic chemistry" J. Fluorine Chem. (2002)118:107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. "Methods for genomic partitioning" Annu Rev Genomics Human Genet. (2009) 10:263-284. doi: 10.1146/annurev-genom-082908-150112. Review.
Jarosz, M. et al. "Using 1ng of DNA to detect haplotype phasing and gene fusions from whole exome sequencing of cancer cell lines" Cancer Res (2015) 75(suppl5):4742.
McCoy, R. et al. "Illumina TruSeq Synthetic Long-Reads Empower De Novo Assembly and Resolve Complex, Highly-Repetitive Transposable Elements" PLOS (2014) 9(9):e1016689.
Ritz, A. et al. "Characterization of structural variants with single molecule and hybrid sequencing approaches" Bioinformatics (2014) 30(24):3458-3466.
Voskoboynik, A. et al. "The genome sequence of the colonial chordate, Botryllus schlosseri." eLife Jul. 2, 2013, 2:e00569.
Wagner, O et al., "Biocompatible fluorinated polyglycerols for droplet microfluidics as an alternative to PEG-based copolymer surfactants" Lab Chip DOI:10.1039/C5LC00823A. (2015).
Wang et al., Single nucleotide polymorphism discrimination assisted by improved base stacking hybridization using oligonucleotide microarrays. Biotechniques. 2003;35:300-08.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Weaver, J.C. et al. "Rapid clonal growth measurements at the single-cell level: gel microdroplets and flow cytometry", Biotechnology, 9:873-877 (1991).
Wheeler et al., "Database resources of the National Center for Biotechnology Information," Nucleic Acids Res. (2007) 35 (Database issue): D5-12.
Whitesides, "Soft lithography in biology and biochemistry", Annual Review of Biomedical Engineering, 3:335-373 (2001).
Williams, R. et al. "Amplification of complex gene libraries by emulsion PCR" Nature Methods (Jul. 2006) 3(7):545-550.
Woo, et al. G/C-modified oligodeoxynucleotides with selective complementarity: synthesis and hybridization properties. Nucleic Acids Res. Jul. 1, 1996;24(13):2470-5.
Xia, "Soft lithography", Annual Review of Material Science, 28: 153-184 (1998).
Yamamoto, et al. Chemical modification of Ce(IV)/EDTA-base artificial restriction DNa cutter for versatile manipulation of doulbe-stranded DNa. Nucleic Acids Research. 2007; 35(7):e53.
Zerbino et al. "Velvet: Algorithms for de novo short read assembly using de Bruijn graphs," Genome Research (2008) 18:821-829.
Zerbino, D.R. "Using the Velvet de novo assembler for short-read sequencing technologies" Curr Protoc Bioinformatics (Sep. 1, 2010) 31:11.5:11.5.1-11.5.12.
Zerbino, Daniel, "Velvet Manual—version 1.1," Aug. 15, 2008, pp. 1-22.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhao, J., et al., "Preparation of hemoglobin-loaded Nano-sized particles with porous structure as oxygen carriers," Biomaterials, vol. 28, pp. 1414-1422 (2007).
Zheng, X.Y. et al. "Haplotyping germline and cancer genomes with high-throughput linked-read sequencing" Nature Biotech (Feb. 1, 2016) 34(3):303-311.
Zhu, S. et al., "Synthesis and self-assembly of highly incompatible polybutadienepoly(hexafluoropropoylene oxide) diblock copolymers" J. Polym. Sci. (2005) 43:3685-3694.
Zimmermann et at., Microscale production of hybridomas by hypo-osmolar electrofusion. Human Antibodies Hybridomas. Jan. 1992;3(1): 14-8.
Zong, C. et al."Genome-wide detection of single-nucleotide and copy-number variations of a single human cell" Science. Dec. 21, 2012;338(6114):1622-6. doi: 10.1126/science.1229164.
Zheng, X. SeqArray: an R/Bioconductor Package for Big Data Management of Genome-Wide Sequencing Variants, Department of Biostatistics, University of Washington, Dec. 28, 2014.

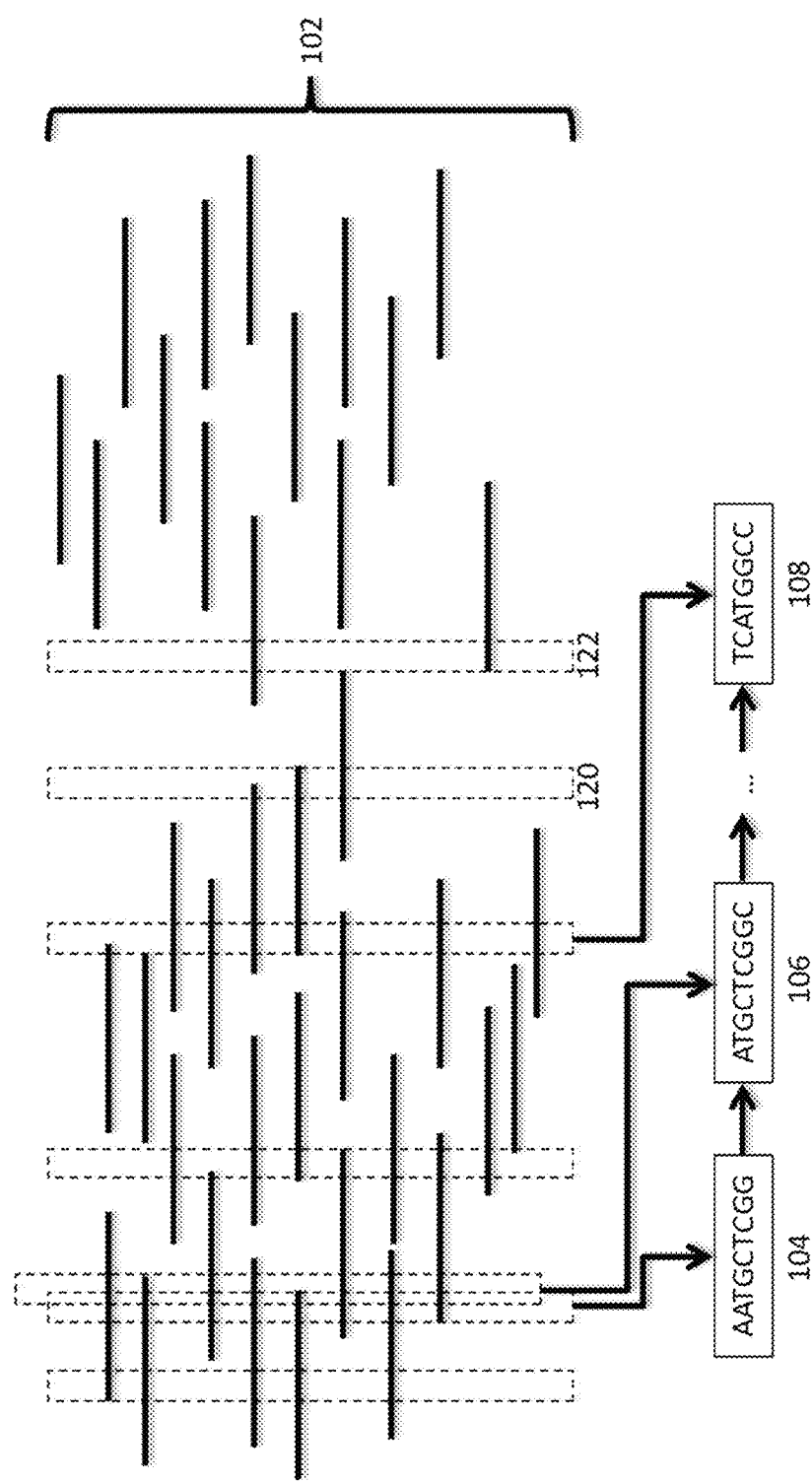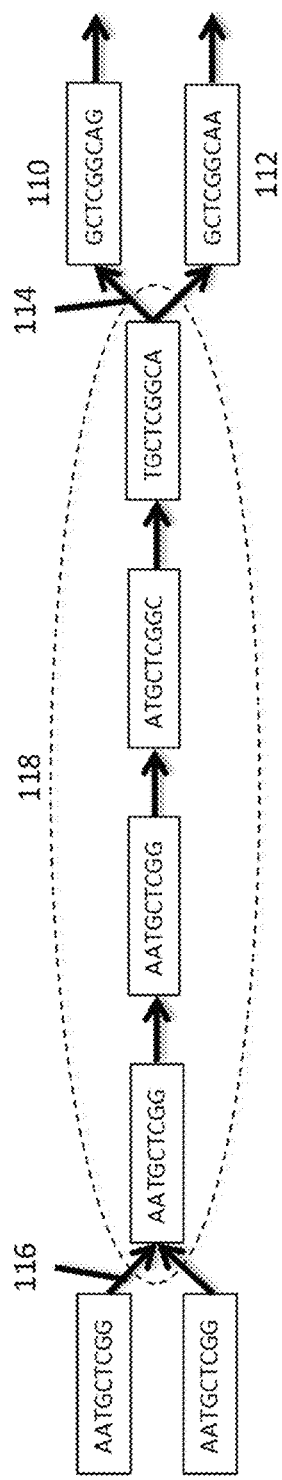
Figure 1A
Figure 1B

| h(W) | 3-mer W | | | | | | | |
|---|---|---|---|---|---|---|---|---|
| 0 | AAA | 16 | CAA | 32 | GAA | 48 | TAA |
| 1 | AAC | 17 | CAC | 33 | GAC | 49 | TAC |
| 2 | AAG | 18 | CAG | 34 | GAG | 50 | TAG |
| 3 | AAT | 19 | CAT | 35 | GAT | 51 | TAT |
| 4 | ACA | 20 | CCA | 36 | GCA | 52 | TCA |
| 5 | ACC | 21 | CCC | 37 | GCC | 53 | TCC |
| 6 | ACG | 22 | CCG | 38 | GCG | 54 | TCG |
| 7 | ACT | 23 | CCT | 39 | GCT | 55 | TCT |
| 8 | AGA | 24 | CGA | 40 | GGA | 56 | TGA |
| 9 | AGC | 25 | CGC | 41 | GGC | 57 | TGC |
| 10 | AGG | 26 | CGG | 42 | GGG | 58 | TGG |
| 11 | AGT | 27 | CGT | 43 | GGT | 59 | TGT |
| 12 | ATA | 28 | CTA | 44 | GTA | 60 | TTA |
| 13 | ATC | 29 | CTC | 45 | GTC | 61 | TTC |
| 14 | ATG | 30 | CTG | 46 | GTG | 62 | TTG |
| 15 | ATT | 31 | CTT | 47 | GTT | 63 | TTT |

Figure 9

(SEQ ID NO:1)

> The one or more fragments 804 of the larger contiguous nucleic acid 802 in a partition in the plurality of partitions consists of between 1 and 500 different fragments 804 of the larger contiguous nucleic acid 802.  —1118

> The one or more fragments 804 of the larger contiguous nucleic acid 802 in a partition in the plurality of partitions consists of between 5 and 100 fragments 804 of the larger contiguous nucleic acid 802.  —1120

> The plurality of sequence reads is obtained from less than 5 nanograms of nucleic or ribonucleic acid.  —1122

> The identifier in the second portion of each respective sequence read in the set of sequence reads encodes a common value selected from the set {1, ..., 1024}, the set {1, ..., 4096}, the set {1, ..., 16384}, the set {1, ..., 65536}, the set {1, ..., 262144}, the set {1, ..., 1048576}, the set {1, ..., 4194304}, the set {1, ..., 16777216}, the set {1, ..., 67108864}, or the set {1, ..., 1 x $10^{12}$}.  —1124

> The identifier is an N-mer, and N is an integer selected from the set {4, ..., 20}.  —1126

> An average sequence read 728 length of the plurality of sequence reads is between 40 bases and 200 bases.  —1128

> An average sequence read 728 length of the plurality of sequence reads is between 60 bases and 140 bases.  —1130

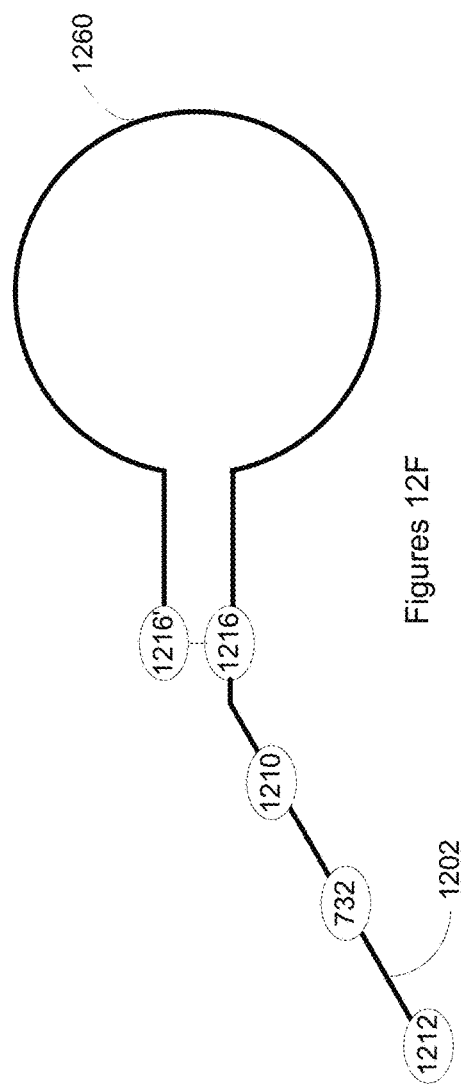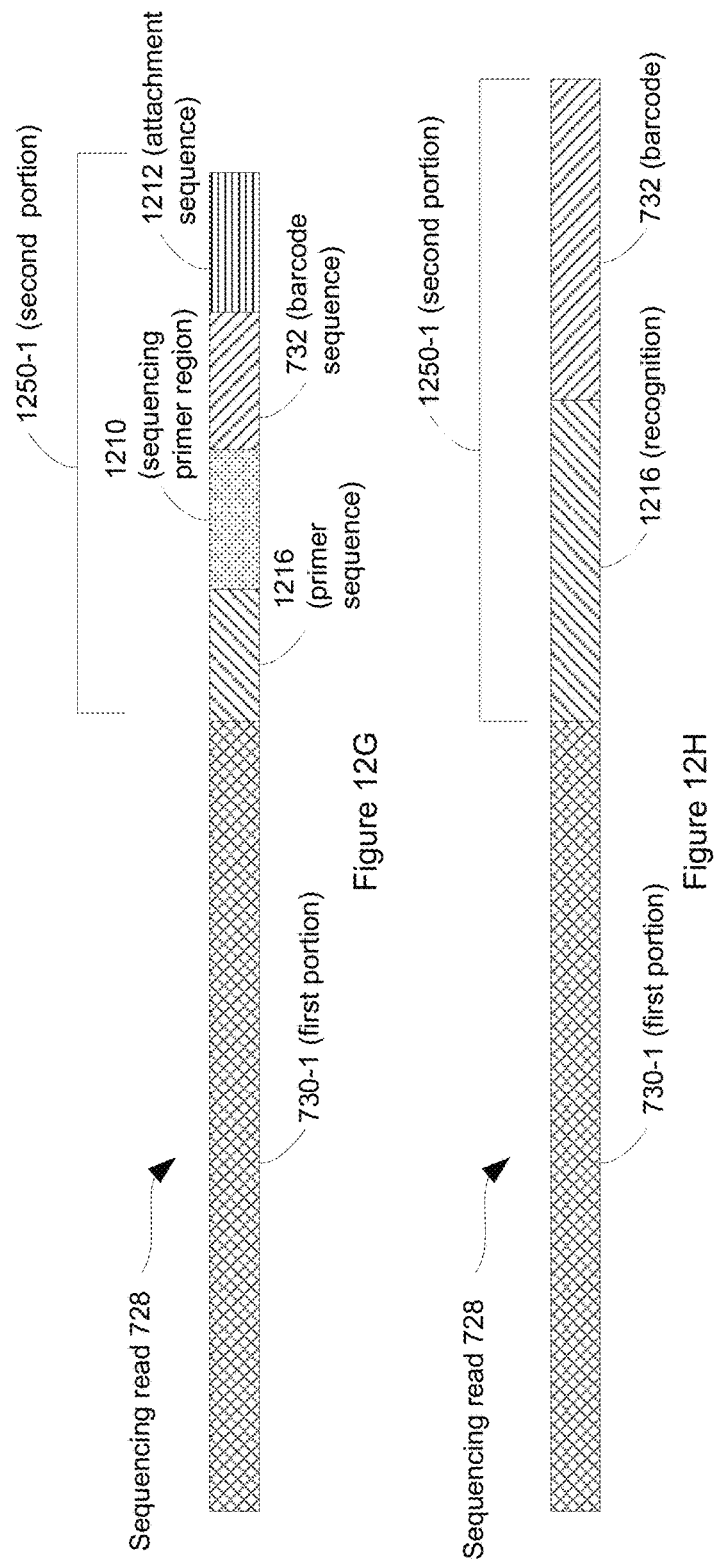

SYSTEMS AND METHODS FOR NUCLEIC ACID SEQUENCE ASSEMBLY

CROSS REFERENCE TO RELATED APPLICATIONS

This application claims priority to U.S. Pat. No. 10,839, 939, entitled "PROCESSES AND SYSTEMS FOR NUCLEIC ACID SEQUENCE ASSEMBLY," filed Jun. 26, 2015, which claims priority to U.S. Provisional Patent Application No. 62/017,589, filed Jun. 26, 2014, entitled "Processes and Systems for Nucleic Acid Sequence Assembly," both of which are hereby incorporated by reference.

TECHNICAL FIELD

The embodiments disclosed herein relate generally to assembling fragmented information.

BACKGROUND

One of the significant challenges associated with high throughput next generation sequencing technologies is in assembling relatively short sequence reads into much longer contiguous sequences. Genomic sequence assembly processes are often analogized to having a novel that is cut into small pieces, which must then be reassembled into the complete novel. In sequence assembly, this is generally accomplished by piecing together overlapping sub-segments of the whole sequence that is to be assembled. As will be appreciated, that assembly process becomes easier when the pieces are larger and less ambiguous. For example, it would be easier to assemble a novel based upon full paragraphs, pages or chapters than it would from individual sentences, sentence fragments or random words or parts of words. Likewise, with nucleic acid sequencing, the shorter the individual sequence read, the more difficult it becomes to assemble multiple reads into a longer contiguous sequence.

While next generation sequencing technologies are capable of generating vast amounts of sequence data, e.g., generating 1 terabase of sequence data within a single run, they are plagued by the difficulties of producing only short sequence read lengths. In particular, these sequencing technologies generally acquire sequence data in reads of 100 contiguous bases or less (or when sequenced as paired end sequencing, up to approximately 200 bases). These reads then must be assembled into longer contiguous sequences. While certain sequencing technologies provide longer sequence reads of 800, 1000, 5000, or even 20,000 bases in length, this often comes at the price of system throughput, yielding only hundreds of megabases of sequence data per run.

A number of processes and algorithms have been employed in assembling relatively short sequence reads into longer contiguous sequences. In general, these short sequence reads typically overlap with a number of other short sequence reads to provide redundant coverage over different parts of the overall longer sequence (referred to as "coverage" or "fold coverage"). At a high level, the overlapping sequences from numerous reads are used to piece together the longer sequence information. In many cases, existing known reference sequences, e.g., from the same species, are available. These reference sequences may be used as a scaffold for mapping the shorter sequence reads onto a larger genome or genome fragment. The multifold sequence coverage is then layered on top of the scaffold to provide a relatively high confidence sequence.

In many cases, however, reference sequences may not be available, requiring de novo assembly of the genome or genomic fragment being sequenced. Moreover, in many cases, such reference sequences are not helpful because the target of the sequencing efforts it to detect mutations in the target sequence. For instance, in the case where the target sequence is from a cancer, it is import to ascertain which mutations, insertions, and deletions are in the target sequence as a way of diagnosing cancer stage or some other attribute of the cancer. As such, making use of references sequences is not always useful in sequencing efforts.

Accordingly, described herein are improved methods, processes and systems for the assembly of sequence reads into larger genome or genome fragment sequences, and particularly, for de novo assembly of sequence information into larger sequence contexts, including for example, whole chromosome or even whole genome contexts.

SUMMARY

Described herein are improved genetic sequence assembly processes used for assembly of sequence reads from a variety of different sequencing systems, including e.g., both short and long read sequencing systems. The processes described herein may be used in both de novo assembly processes and in re-sequencing assembly processes or assembly processes against known reference sequences.

The methods, processes and systems described herein employ sequence reads with associated barcode sequences to assist in the overall assembly process at one or more different assembly steps.

In certain aspects, provided are methods of assembling nucleic acid sequence reads into larger contiguous sequences. The methods comprise identifying a first subset of sequence reads that comprise both overlapping sequences and a common barcode sequence in a computer implemented system comprising a first data structure comprising a plurality of sequence reads derived from a larger contiguous nucleic acid. Sequence reads derived from a common fragment of the larger contiguous nucleic acid comprise a common barcode sequence. The first subset of sequence reads is aligned to provide a contiguous linear nucleic acid sequence Also provided are methods of assembling nucleic acid sequence reads into larger contiguous sequences. Such methods identify a first subsequence from a set of overlapping sequence reads in a computer implemented system comprising a first data structure comprising a plurality of sequence reads derived from a larger contiguous nucleic acid. The first subsequence is then extended to one or more adjacent or overlapping sequences based upon the presence of a barcode sequence on the adjacent sequence that is common to the first subsequence. A linear nucleic acid sequence is then provided that comprises the first subsequence and the one or more adjacent sequences.

One aspect of the present disclosure provides a sequencing method comprising, at a computer system having one or more processors, and memory storing one or more programs for execution by the one or more processors, implementing a method in which a plurality of sequence reads is obtained. The plurality of sequence reads comprises a plurality of sets of sequence reads. Each respective sequence read in a set of sequence reads includes (i) a first portion that corresponds to a subset of a larger contiguous nucleic acid and (ii) a common second portion that forms an identifier that is independent of the sequence of the larger contiguous nucleic acid and that identifies a partition, in a plurality of partitions, in which the respective sequence read was formed. Each respective set of sequence reads in the plurality of sets of sequence reads is formed in a partition in the plurality of partitions and each partition includes one or more fragments (e.g., two or more, three or more, ten or more) of the larger contiguous nucleic acid that is used as the template for each respective sequence read in the partition.

In the method, a respective set of k-mers is created for each sequence read in the plurality of sequence reads. The sets of k-mers collectively comprise a plurality of k-mers. The identifier of the sequence read for each k-mer in the plurality of k-mers is retained. In many instances, there are multiple such sequencing read identifiers for at least some of the k-mers. The value k is less than the average length of the sequence reads in the plurality of sequence reads. Each respective set of k-mers includes some (e.g., at least eighty percent) of the possible k-mers of length k of the first portion of the corresponding sequence read.

In the method, there is tracked, for each respective k-mer in the plurality of k-mers, an identity of each sequence read in the plurality of sequence reads that contains the respective k-mer and the identifier of the set of sequence reads that contains the sequence read.

In the method, all or a portion (e.g., at least 1 percent, at least 5 percent, at least fifty percent) of the plurality k-mers are graphed as a graph comprising a plurality of nodes connected by a plurality of directed arcs. Each node comprises an uninterrupted set of k-mers in the plurality of k-mers of length k with k−1 overlap. Each arc connects an origin node to a destination node in the plurality of nodes. A final k-mer of an origin node has k−1 overlap with an initial k-mer of a destination node. A first origin node has a first directed arc with both a first destination node and a second destination node in the plurality of nodes.

In the method, a determination is made as to whether to merge the origin node with the first destination node or the second destination node in order to derive a contig sequence that is more likely to be representative of a portion of the larger contiguous nucleic acid. The contig sequence comprises (i) the origin node and (ii) one of the first destination node and the second destination node. The determining uses at least the identifiers of the sequence reads for k-mers in the first origin node, the first destination node, and the second destination node.

Another aspect provides a computing system, comprising one or more processors, memory storing one or more programs to be executed by the one or more processors, the one or more programs comprising instructions for executing the method described above.

Another aspect of the present disclosure provides a sequencing method comprising, at a computer system having one or more processors, and memory storing one or more programs for execution by the one or more processors, obtaining a plurality of sequence reads. The plurality of sequence reads comprises a plurality of sets of sequence reads. Each respective sequence read in a set of sequence reads includes (i) a unique first portion that corresponds to a subset of a larger contiguous nucleic acid and (ii) a common second portion that forms an identifier that is independent of the sequence of the larger contiguous nucleic acid and that identifies a partition, in a plurality of partitions, in which the respective sequence read was formed. Each respective set of sequence reads in the plurality of sets of sequence reads is formed in a partition in the plurality of partitions. Each such partition includes one or more fragments of the larger contiguous nucleic acid that is used as the template for each respective sequence read in the partition.

In the method, a respective set of k-mers is created for each sequence read in the plurality of sequence reads. The sets of k-mers collectively comprise a plurality of k-mers. The identifier of the sequence read for each k-mer in the plurality of k-mers is retained. The value k is less than the average length of the sequence reads in the plurality of sequence reads. Each respective set of k-mers includes at least some of (e.g., at least eighty percent of) the possible k-mers of the first portion of the corresponding sequence read.

In the method, there is tracked, for each respective k-mer in the plurality of k-mers, an identity of the each sequence read in the plurality of sequence reads that contains the respective k-mer. A first path is identified. The first path comprises a first set of k-mers with k−1 overlap in the plurality of k-mers. A second path is identified. The second path comprises a second set of k-mers with k−1 overlap in the plurality of k-mers. The first path intersects the second path (e.g., as illustrated in FIG. 15), thereby forming the set of branch segments comprising: a left portion of the first path, a right portion of the first path, a left portion of the second path and a right portion of the second path. The identifiers associated with the k-mers of the set of branch segments are used to verify the connectivity of the branch segments. In some embodiments, this comprises evaluating a number of identifiers shared between each possible branch segment pair in the set of branch segments.

In some embodiments, a partition in the plurality of partitions comprises at least 1000 molecules with the common second portion, and each molecule in the at least 1000 molecules includes a primer sequence complementary to at least a portion of the larger contiguous nucleic acid.

In some embodiments, the identifier in the second portion of each respective sequence read in the set of sequence reads encodes a common value selected from the set $\{1, \ldots, 1024\}$, the set $\{1, \ldots, 4096\}$, the set $\{1, \ldots, 16384\}$, the set $\{1, \ldots, 65536\}$, the set $\{1, \ldots, 262144\}$, the set $\{1, \ldots, 1048576\}$, the set $\{1, \ldots, 4194304\}$, the set $\{1, \ldots, 16777216\}$, the set $\{1, \ldots, 67108864\}$, or the set $\{1, \ldots, 1\times10^{12}\}$.

In some embodiments, the identifier is an N-mer, where N is an integer selected from the set $\{4, \ldots, 20\}$.

In some embodiments, an average sequence read length of the plurality of sequence reads is between 40 bases and 200 bases or between 60 bases and 140 bases.

In some embodiments, the plurality of sequence reads collectively provide at least 15× coverage for the larger contiguous nucleic acid, more than ten percent of the k-mers in the plurality of k-mers are from more than one source sequence read in the plurality sequence reads, and the identifier of each such source sequence read for each k-mer represented by more than one source sequence read is retained.

In some embodiments, the plurality of sequence reads collectively provide at least 25× coverage for the larger contiguous nucleic acid, more than thirty percent of the plurality of k-mers are from more than one source sequence read in the plurality sequence reads, and the identifier of each such source sequence read for each k-mer represented by more than one source sequence read is retained.

In some embodiments, the sequence reads in the plurality of sequence reads encode between 75 and 125 bases of the larger contiguous nucleic acid and k is an odd integer between 5 and 73.

In some embodiments, a set of sequence reads in the plurality of sequence reads comprises more than 100 sequence reads, each with the same common second portion.

In some embodiments, the larger contiguous nucleic acid is a chromosome and/or is greater than 40 million base pairs in length.

BRIEF DESCRIPTION OF THE DRAWINGS

FIG. 1A provides a schematic illustration of alignment of overlapping sequence reads.

FIG. 1B shows a sample de Bruijn initial assembly graph based upon the sequence reads, with primary path identification.

FIG. 9 illustrates the possible values of h(W) for the sixty-four possible k-mers of length three in accordance with some embodiments.

FIG. 10 illustrates the possible k-mers of length three generated from the sequence GATCCATCTT (SEQ ID NO: 1) in accordance with some embodiments.

FIGS. 11A, 11B, 11C, 11D, and 11E collectively illustrate process flows for sequencing in accordance with some embodiments.

FIGS. 12A, 12B, 12C, 12D, 12E, 12F, 12G and 12H collectively illustrate a method for obtaining a plurality of sequence reads, where the plurality of sequence reads comprises a plurality of sets of sequence reads, where each respective sequence read in a set of sequence reads includes (i) a first portion that corresponds to a subset of a larger contiguous nucleic acid and (ii) a common second portion that forms an identifier that is independent of the sequence of the larger contiguous nucleic acid and that identifies a partition, in a plurality of partitions, in which the respective sequence read was formed, in accordance with some embodiments.

Like reference numerals refer to corresponding parts throughout the present disclosure.

DETAILED DESCRIPTION

Figure 2:
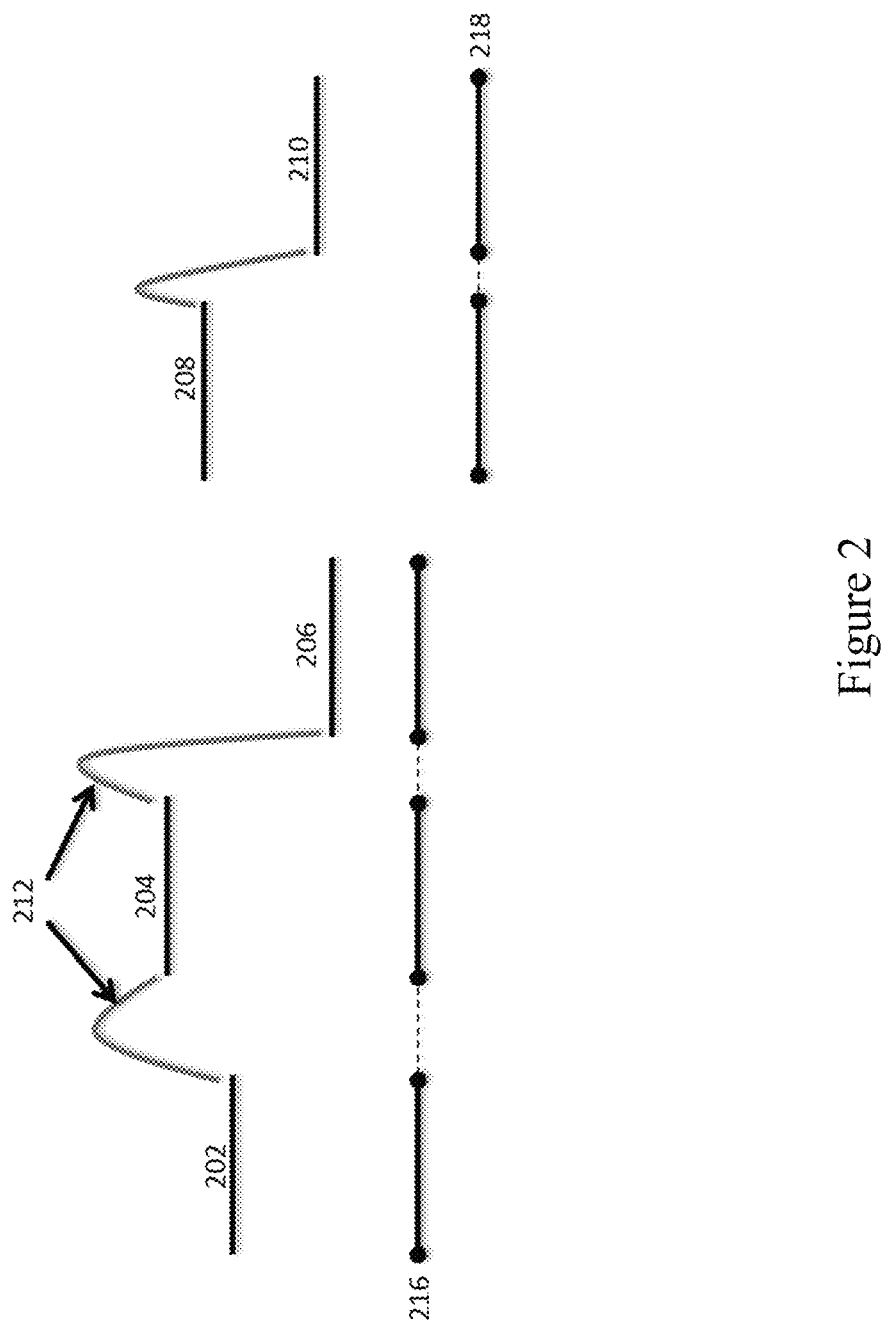
FIG. 2 shows a high level linkage map connecting primary paths in an overall assembly process in accordance with some embodiments.

The invention and various specific aspects and embodiments will be understood with reference to the following drawings and detailed descriptions. In some of the drawings and detailed descriptions below, the present invention is described in terms of an important independent embodiment of a system operating on a logic processing device, such as a computer system. This should not be taken to limit the invention, which, using the teachings provided herein, can be applied to any number of logic processors working together, whether incorporated into a standalone computer system, an instrument system, or other information enabled devices or logic components incorporated into laboratory or diagnostic equipment or in functional communication therewith. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. The functional aspects of the invention that are implemented on a computer or other logic processing systems or circuits, as will be understood from the teachings herein, may be implemented or accomplished using any appropriate implementation environment or programming language, such as C, C++, Cobol, Pascal, Java, Java-script, HTML, XML, dHTML, assembly or machine code programming, RTL, Python, etc. All references, publications, patents, and patent applications cited herein are hereby incorporated by reference in their entirety for all purposes.

As used herein, the terms "sequence read" and "entity" are used interchangeably.

As used herein, the terms "source entity" and "contiguous nucleic acid" are used interchangeably.

As used herein, the terms "partition" and "unit" are used interchangeably.

As used herein, the terms "k-mer" and "piece" are used interchangeably.

As used herein, the terms "origin node" and "first node" are used interchangeably.

As used herein, the terms "first destination node" and "second node" are used interchangeably.

As used herein, the terms "second destination node" and "third node" are used interchangeably.

I. General

In general, assembly of nucleic acid sequence information into longer stretches of contiguous sequence typically involves the identification of overlapping sequences in different reads, and using those overlapping sequences to map these sequences against each other. Because genomic sequences are very large, the identification of overlapping sequences only allows for an inference of linkage between the two sequences. This inference is substantially strengthened with larger numbers of overlapping sequences in a given region of the overall sequence, e.g., higher coverage.

In some embodiments, this inference may be further strengthened when the sequences are mapped against a reference sequence. In particular, for a number of organisms, a reference sequence, e.g., a complete or nearly complete sequence of one individual's genome or a consensus of the organism's genome from multiple individuals, has been elucidated that provides a general framework of that organism's genomic sequence. Groups of overlapping sequences may then generally be mapped against a reference sequence for the given organism from which the DNA is being sequenced in order to provide greater confidence in the identified sequence linkage, as well as place the different sequence segments into the larger genomic context. However, in some embodiments of the present disclosure, reference sequences are not used.

In assembling the larger overall sequence, areas in the sequence that have insufficient information (e.g., insufficient coverage, lack of an unambiguous match to a reference sequence, etc.) can result in breaks in the overall inferred sequence. These breaks result in a number of separate contiguous sequence segments (or contigs) that can require substantial additional processing before they are eventually linked in a single contiguous sequence. These challenges, while significant in sequencing processes where reference sequences are available, are even more significant in de novo sequence assembly. By definition, de novo assemblies do not have the benefit of the secondary level of confirmation of sequence linkage that comes from a reference sequence. Instead, these sequences must be assembled from the bottom up, e.g., de novo.

In an example process, an aggregation of short sequence reads are obtained from any of a variety of different sequencing processes. The sequence reads are optionally stored in an appropriate data structure for further evaluation. A computer algorithm analyzes these sequences to identify common sequence segments (k-mers) among subsets of the different sequence reads. Identification of k-mer subsequences is typically based upon the level of redundancy or coverage of the k-mer sequence of a desired length, which may generally be dependent upon the complexity of the genome being sequenced, the depth of sequencing coverage, and tolerances for varying error types. In many cases, k-mer length may be selected that are anywhere from about 7 to about 31 bases in length, or from about 15 to about 25 bases in length. For example, where a given k-mer is only represented less than 3, 4, 5, 10, 20 or more times, in the aggregated sequence database, it may be deemed insufficiently covered to meaningfully be used, depending upon the complexity of the sequence being analyzed, etc.

Sequence fragments that include an identified k-mer sequence are then aligned along that sequence of overlap between the sequences. Additional k-mer sequence or sequences may then be identified in these overlapping sequences to compile an aggregation of additional sequence segments to extend the contiguous sequence in an initial assembly graph using an additional assembly algorithm that extends from this k-mer to an overlapping k-mer to produce a full contig sequence, e.g., using a DeBruijn graph assembler such as Velvet, Euler or the like. In particular, the first set of reads having a first k-mer sequence may be used as an anchor for a repeated alignment exercise in which a second k-mer sequence common to one or more members of the first set, is used to extend the inferred sequence, i.e., to establish a connection between the first set of short sequences and a second set of short sequences. This is repeated so long as the sequence is able to be extended, unambiguously.

In genomic samples, however, k-mer sequences may be common to multiple disparate portions of the overall sequence, such that the identification of a subsequent k-mer sequence can implicate two or more different sets of sequence reads as extensions of a given sequence, where those two sequences are not actually related, e.g., one or more of those sequences is not the correct extension of the sequence. This results in a branch in the inferred connection between sequences, e.g., one of two or more sequences may constitute the continued sequence at this branch point. The maximal unbranched inferred sequence is generally termed a 'primary path'. Multiple primary paths are identified for a short read sequence dataset. Different primary paths may then be linked to each other through other processes, e.g., using paired end sequence data, overlaying long read sequence data, or the like.

FIGS. 1A and 1B provide a schematic illustration of the de novo assembly process described above. As shown, sequence fragments 102 are aligned according to included k-mer sequences that are represented at sufficiently high levels of coverage, e.g., k-mers 104, 106 and 108, as compared to the other k-mers that are represented at lower coverage, e.g., k-mers in alignments 120 and 122 k-mers. For example, in some cases, k-mers representing coverages of at least 3-4× would be used for alignment. Although illustrated as k-mers that are only eight bases in length, this is done for ease of illustration, and actual k-mer lengths may vary and may be longer, e.g., 10 mer or longer, 20mer or longer, 30mer or longer, 40mer or longer, 50mer or longer, 60mer or longer, 70mer or longer, 80mer or longer, 90mer or longer, 100mer or longer.

A series of overlapping k-mer sequences is identified, e.g., k-mers 104 and 106, to walk along the aggregate overlapping fragments and assemble a longer contiguous sequence. As shown in FIG. 1B, where a given step leads to two or more overlapping k-mers, e.g., k-mers 110 and 112, it creates a branch point 114 in the contiguous sequence. Element 116 of FIG. 1B illustrates another break point in the contiguous sequence. The stretch of unbranched sequence between the two branch points is defined as a primary path 118. Although illustrated as a relatively short primary path, it will be appreciated that longer primary paths are generally generated, e.g., comprising 500 bases, 1 kb, 2 kb, 5 kb, or more in length.

Seed primary paths are then identified from the data. Seed primary paths, also referred to as seed paths, typically represent primary paths that are more likely to have a low copy number within the genome or other large sample nucleic acid (e.g., n approaching 1). This copy number may be inferred from the length of the sequence in the primary path, or from the overall read coverage of the primary paths, or both. From each seed path, neighboring or linked primary paths are then identified, either through an unambiguous overlap with the seed path, or through the use of other linkage information, e.g., long read sequencing data, or paired end sequence reads that can bridge two primary paths, e.g., one is represented in one primary path while the other end is represented in a different primary path. The linkage between two primary paths may be expressly determined, e.g., through sequencing of the intervening sequence, or it may be an inferred structural linkage where the relative position and connection of the two primary paths is inferred, e.g., from paired end sequence reads.

This is shown in FIG. 2, which schematically illustrates a number of separate primary paths 202-210, where a structural linkage (shown as linkages 212) is determined as between the primary paths. As shown, in some cases, linkages will not be determinable.

The longest assembled contiguous sequence segments are then compiled (shown in FIG. 2 as contigs 216 and 218). Typically, lengthy genome finishing processes, e.g., using laborious Sanger sequencing or other long read sequencing processes, e.g., SMRT® sequencing from Pacific Biosciences), are then used to close remaining gaps in the overall sequence, e.g., the gap between contigs 206 and 208.

As is clear from the above example, merely assembling a reasonable finished genome or reasonable number of contigs for a given genome, can involve multiple different sequencing processes, e.g., high throughput, short-read shotgun sequencing, paired-end long fragment sequencing and/or low throughput long-read DNA sequencing processes. Each of these processes can be costly and time consuming.

As described herein, however, an improved sequencing and assembly process allows one to obtain substantially more complete assembly from fewer or even a single, more efficient sequencing processes. In particular, in accordance with the processes described herein, structurally linked oligonucleotides that are sequencable using, e.g., short read sequencing techniques, are provided with common unique identifiers, e.g., barcodes, that may be used in the assembly process to infer linkage between different sequence segments and/or different primary paths, in the assembly process.

II. Linked-Read Sequencing

Barcoding of structurally linked short sequences and resulting sequence reads may be carried out by a number of methods. An exemplary process is described in detail in, for example, U.S. provisional Patent Application No. 61/940, 318, filed Feb. 7, 2014, U.S. provisional Patent Application No. 61/991,018, filed May 9, 2014, U.S. patent application Ser. No. 14/316,383, filed on Jun. 26, 2014, as well as U.S. patent application Ser. No. 14/175,935, filed Feb. 7, 2014, the full disclosures of which is hereby incorporated by reference in their entireties.

In brief, sequencing libraries with incorporated barcode sequences are prepared from one or more large nucleic acid sequences, e.g., a genome, chromosome or fragment thereof. This large sample nucleic acid(s) is segmented into first fragments that will typically be on the order of 1 to about 100 kb or more in length. These long first fragments are then partitioned into separate reaction volumes. While these reaction volumes may be any of variety of different types of reaction vessels, e.g., tubes, wells, microwells, nanowells, or the like, in preferred aspects, the reaction volumes (also referred to as partitions), are comprised of droplets in an emulsion, e.g., a water-in-oil emulsion).

This partitioning may be carried out so as to ensure that at most, only a single first fragment is contained in any partition. However, such processes tend to have reduced throughput and higher costs, as the partitions are inefficiently used where most partitions would remain empty. As such, in preferred aspects, the partitioning is carried out under conditions in which there are multiple first fragments contained in individual partitions, but where there is a high probability that while multiple first fragments may be present within a given partition, such fragments will be structurally unique, e.g., representing structurally discrete and disparate regions of the larger sample nucleic acid. Typically, this is accomplished by providing the first fragments at a concentration that, based upon the size of the sample nucleic acid, the size of the first fragments, and the reaction volume, will statistically allocate structurally unique first fragments into each separate reaction volume. In particular, such partitioning will result in fewer than 10% of the partitions having structurally linked separate first fragments (overlapping, non-overlapping but immediately adjacent, or adjacent within 0.1 to 5 kb), fewer than 5% of the first fragments in a given partition being structurally linked, fewer than 1% of the first fragments in a given partition being structurally linked, and in some cases, fewer than 0.5%, 0.2%, or even fewer than 0.1% of the first fragments in a given partition being structurally linked.

Co-partitioned with the first fragments, e.g., within the same droplet, are collections of oligonucleotides that comprise a common barcode sequence within a given partition. The collection of oligonucleotides is taken from a vast and diverse library of different barcode sequences, such that different partitions have different barcode sequences contained therein. In preferred aspects, the oligonucleotides comprising the barcode sequences are provided into the individual partitions releasably attached to a bead or microcapsule, where the barcode sequences included within the oligonucleotides attached to a given bead are all substantially identical. Further, each bead will typically comprises more than 100,000, more than 1,000,000, more than 10,000, 000 and in many cases, more than 50,000,000 individual oligonucleotide molecules. The oligonucleotides may be drawn from a barcode library that includes greater than 1000, greater than 10,000, greater than 100,000, greater than 500,000, greater than 1 million, or even greater than 2 million different barcode sequences.

In preferred aspects, these oligonucleotides also include functional sequences, e.g., amplification primer sequences (which may be targeted to specific sequences, universal priming sequences or random priming sequences), or primer annealing sites, sequencing primer sequences or primer annealing sites, or the like. In preferred cases, universal or random primer sequences are included as at least one of the functional sequences within the oligonucleotides. These and other functional sequences are described in, for example, U.S. provisional Patent Application No. 61/940,318, filed Feb. 7, 2014, U.S. provisional Patent Application No. 61/991,018, filed May 9, 2014, U.S. patent application Ser. No. 14/316,383, filed on Jun. 26, 2014, as well as U.S. patent application Ser. No. 14/175,935, filed Feb. 7, 2014, the full disclosures of which is hereby incorporated by reference in their entireties.

A population of second, sequencable shorter fragments, that constitute overlapping fragments of the first fragment, are then generated within the reaction volume, where the second short fragments include the common barcode sequence segment. In one exemplary process, this is carried out by releasing the oligonucleotides comprising the barcode sequences from the beads into the partitions. While the release of the oligonucleotides may be carried out using a variety of mechanisms to release the oligonucleotides from the beads, e.g., thermal cleavage, chemical cleavage, or photo-induced cleavage, in many cases, the release will be carried out by introducing a chemical cleaving agent into the partitions during the co-partitioning step that will either cleave a linkage between the oligonucleotide and the bead, or degrade the bead such that the oligonucleotide is released, or both.

Also co-partitioned with the first fragments and oligonucleotides are reagents for carrying out the amplification of different portions of the first fragments, including, for example, DNA polymerase enzyme, nucleoside triphosphates, divalent metal ions, e.g., $Mn'$ or $Mg'$. Portions of the first fragments in a given partition are then replicated using the oligonucleotides, e.g., including a universal or random primer sequence, as primers for that replication, such that different portions of the first fragment are primed and replicated. In some cases, these first replicate fragments may be additionally primed by the oligonucleotides and replicated. As a result of these replications, a collection of overlapping fragments of the first fragments in a given partition is created, where each includes a barcode sequence common to that partition.

In different partitions, different second fragments are generated from different first fragments in a similar fashion, with different barcode sequences appended to those second fragments. Across the collection of different partitions is then created a substantial sequencing library, where elements of that library that are created in the same partition, and thus may be derived from the same first fragment, will include the same barcode sequence.

The different partitions, representing the sequencing library, are then pooled and the fragments included therein are sequenced to identify the short second fragment sequences along with their appended barcode sequences. Because second fragments derived from a given first fragment will include a common barcode sequence, the presence of that barcode sequence in a given read, or set of reads provides additional linkage inferences that may be applied throughout the assembly process.

III. Application to Assembly

A. Generally

As described previously, a number of different parameters are used in assembly of shorter sequence reads into longer contiguous linked sequences. These include the presence of overlapping sequence segments between and among sequence reads that provide an inference that the sequence reads represent overlapping segments of a larger sequence context. The ability to provide longer linked shorter sequences, as well as the ability to provide linkage inferences as between larger sequence fragments from a given nucleic acid, e.g., the ability to provide fewer contigs or even a single unified sequence for the larger molecule, will depend to some extent upon the level and uniformity of sequencing coverage for the entire target nucleic acid, where regions with lower levels of sequencing coverage may result in gaps between contigs. As a result, sequencing processes that have more low coverage areas often result in more discontinuous sequence data, e.g., a larger number of contigs. While some of the coverage deficiencies can be overcome by brute force, e.g., sequencing a genome to much greater depth, that solution comes at a potentially large cost, in terms of sequencing process costs. However, in many cases, coverage deficiencies are systematic, e.g., resulting in part from the sequence itself.

By contrast, the assembly of barcoded sequencing libraries, as described herein, can provide enhanced linkage information both at the short sequence read level as well as in the higher level assembly, without necessarily requiring significant increases in coverage, or the use of ancillary additional sequencing processes.

In particular, in typical short sequence read assembly processes, short sequence reads that include overlapping sequence segments are aligned with each other to provide a larger contiguous sequence context, or contig. These contigs may then be subjected to further assembly with other contigs de novo, or by being mapped against a reference sequence. However, because these sequence reads are extremely short, e.g., 100-200 bases in length, in the context of genomes that are in the millions to billions of bases, the potential for any given read to map uniquely to a single locus within the genome is relatively low, and this can introduce significant ambiguity in the assembly process. This ambiguity may be lessened by sequencing large numbers of overlapping fragments to provide greater sequencing coverage at a give locus. However, low coverage areas of a genome will still provide difficulties in any assembly process, often leaving gaps between contigs. While lower coverage areas may be bridged by other methods as described elsewhere herein, e.g., long read sequencing, such methods add to the cost and inefficiency of the processes.

In the context of the methods described herein, however, short read sequences are provided with barcode sequences that provide additional inferences of structural relationship between two or more sequence reads without the requirement of as much sequencing coverage. In particular, aligned short read sequences may be assigned to an aligned contig based upon both an overlapping sequence with other sequences, as well as based upon their inclusion of a common barcode sequence. Using the additional structural linkage information of an associated common barcode sequence results in the identification of much longer contigs.

Likewise, bridging between two contigs may additionally be aided by the presence of barcode sequences. For example, where adjacent identified contigs include sequence reads that share overlapping barcode sequences, but are otherwise non-overlapping or insufficiently overlapping to align together, one may infer a structural linkage as between those two contigs. Briefly, the inclusion in two sequence reads provides a reasonably strong inference that the two reads were generated from fragments created within a single partition. When combined with additional linkage information, e.g., alignment of the sequence read to two or more contigs, or where two barcodes straddle the same two contigs, it gives a significant indication of the linkage of those two contigs.

In terms of an exemplary computer implemented process, a collection of short read sequences that include associated barcode sequences, are provided within a data structure. Subsets of the sequences are aligned with each other based upon overlapping sequences within those sequences, and also based upon the association of such sequences with the same barcode sequence. Alignable sequences that do not include the same barcode sequence, or sequences that include the same barcode sequences but that are not alignable are not included, and may be aligned against different subsets of sequences. Based upon a set of aligned, commonly barcoded sequences, a linear contiguous sequence, or contig is generated. This is repeated with multiple different subsets of sequences, to provide multiple different contigs. As will be appreciated, the contigs may be longer than what would be achieved based upon sequence alignment alone, or may be provided with higher levels of confidence, despite being based upon lower sequencing coverage.

The generated contigs are then processed further to provide relative orientation and genomic context with respect to each other to establish a scaffold for the overall genomic (or other genomic component) sequence. In some cases, this may be achieved through mapping of the discrete contigs against a reference sequence. In many cases, however, mapping against a reference may not be unambiguous, e.g., based upon the presence of multiple duplicate sequence regions within the genome, or because a suitable reference sequence does not exist.

In such cases, barcoded sequences may additionally be used to provide linkage information as between contigs. For example, as noted above, in some cases, sequences that align to a first subset of sequences, but that do not share a common first barcode sequence, e.g., they include a second barcode sequence, would not be used in creating the first contig. However, such sequences may be aligned in creating a second contig. Likewise, sequences that include a first barcode, but that align to the second contig sequences may not have been used to generate the second contig. However, based upon such sequences being present in the data structure, one can ascertain a linkage between the first and second contig. In the context of the processes, contig linkage may be identified based upon the presence of a threshold level of shared barcodes as between sequences that align to different contigs, and/or based upon the presence of a threshold level of sequences that that align to the first contig but include barcodes associated with the second contig. As used herein, such threshold level may include a single sequence or, 2 sequences or more, 3 sequences or more, 4 sequences or more, 5 sequences or more, 10 sequences or more, or 20 sequences or more.

B. Application to De Novo Assembly Processes

The barcoded sequencing libraries described above have particular advantages in de novo assembly. In particular, as noted above, the presence of a common barcode in two sequence reads can provide an inference of structural linkage between the two sequences, as there is an increased probability that these sequences were created within the same partition, and from the same first fragment. While this may not be definitive, as the same barcode sequence may be present in other partitions and in fragments of structurally unrelated first fragments, when combined with other indicators of structural relation, e.g., overlapping sequences, it becomes a powerful inference of structural linkage. By way of example, and with reference to the assembly process described above, FIG. 3 schematically illustrates a potential impact of barcoded sequences on the assembly processes.

In one aspect, the barcodes included within the sequence reads may be used to provide a structural relationship between and among paths in an initial assembly in order to provide high level scaffolding of a sequence, e.g., providing a high confidence primary path scaffold in which the relative order of primary paths, and preferably, high confidence primary paths is identified and mapped, and against which final genomic assembly may be mapped. As will be appreciated, a high confidence primary path will generally refer to a primary path that, based upon its length and complexity, will be expected to have a low probability of duplication or multiple duplication within a genome, allowing a higher level of confidence that sequences or primary paths that connect to that primary path are, in fact, actually linked in the genome, as opposed to being linked to primary paths having a duplicate sequence. In preferred aspects, the high confidence primary paths are primary paths that will have a predicted copy number in the relevant genome approaching 1, e.g., less than 2, or equal to about 1.

In brief, a set of primary paths will have been identified from the initial assembly graph as described above, including high confidence primary paths (also referred to herein as "single copy number", "low copy number", or "CN1" paths). Each sequence read included within a given primary path will include an associated barcode sequence, as also described above. A list of barcodes associated with each primary path may then be generated for each primary path. Using the associated barcoded sequences, an initial sequence path may be plotted between adjacent CN1 primary paths, using those primary paths (both CN1 and otherwise) that share common barcode sequences. The path is then extended to the next adjacent CN1 path, providing ordering of the CN1 paths relative to each other. As will be appreciated, in many cases, duplicate barcode sequences may exist within the overall sequencing process and be attached to structurally distinct portions of a larger nucleic acid, e.g., chromosomal fragment, or genome fragment. However, because the assembly process focuses on low copy number or CN1 paths, utilizes highly diverse barcode libraries (e.g., greater than 1000, 5000, 10,000, 100,000 or even 1 million different barcode sequences), and is addressing very large genetic samples, it would be expected that the probability of the same barcode sequence being attached to similar or overlapping sequences that derive from structurally distinct, e.g., not structurally linked, parts of the genome or genomic fragment, would be extremely low, e.g., in many cases, less than 0.0001%.

This connection process is repeated among the CN1 paths until the order of all of the CN1 paths is established. The CN1 paths may then be used as a scaffold for completing assembly of the sequence between the paths. This is generally accomplished in a similar fashion, by using the sequence reads that include barcodes common to the CN1 paths to create a local sequence assembly graph between adjacent CN1 paths.

Figure 3:
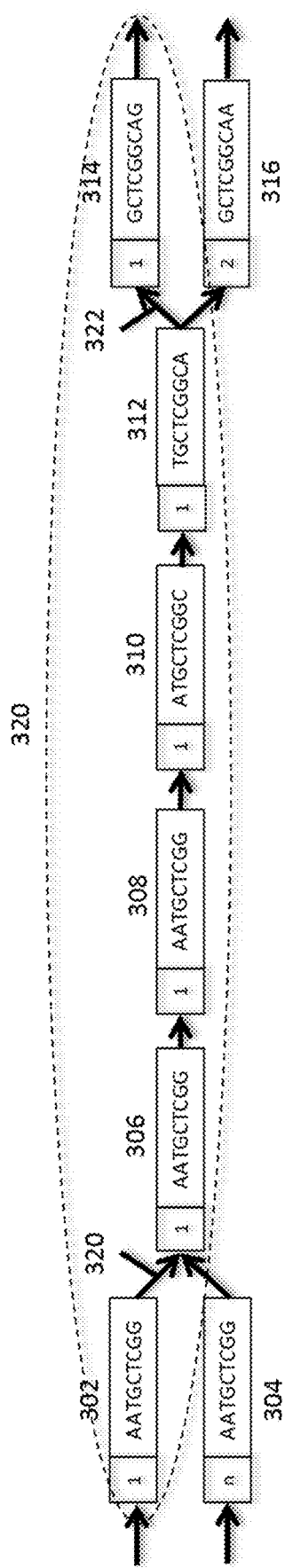
FIG. 3 schematically illustrates a barcode assisted assembly process in accordance with some embodiments.

In particular, sequence reads including the same barcode sequences as a given primary path are used to stitch together a local sequence assembly graph between two adjacent primary paths in the scaffold, in the same fashion as described above for assembly of the initial assembly graph. This assembly map provides the sequence for the space between the two primary paths, closing the sequence gap. By utilizing barcode information associated with each sequence in which the k-mer exists, in addition to the overlapping sequence data in the k-mers, one can unambiguously identify the sequence extending between two primary paths. This is schematically illustrated in FIG. 3. As shown, a series of k-mer sequences 302-316, similar to those schematically illustrated for the global assembly graph in FIG. 1A are illustrated, except where each k-mer is coupled to an incorporated barcode sequence 318, e.g., barcode sequence "1", barcode sequence "2" or barcode sequence "n". As with the initial assembly graph, the presence of diverging kmer sequences at a given point or points could give rise to branch points within the sequence, e.g., branch points 320 and 322. However, by relying in part on the barcode information associated with each k-mer sequence, one can effectively identify the correct sequence path, eliminating the branch point. In particular, with reference to branch point 322, while both of k-mers 314 and 316 represent possible next sequence steps, because only the path associated with k-mer 314 includes the common barcode "1", it is identified as the next sequence step.

C. Exemplary Embodiments

Figure 7:
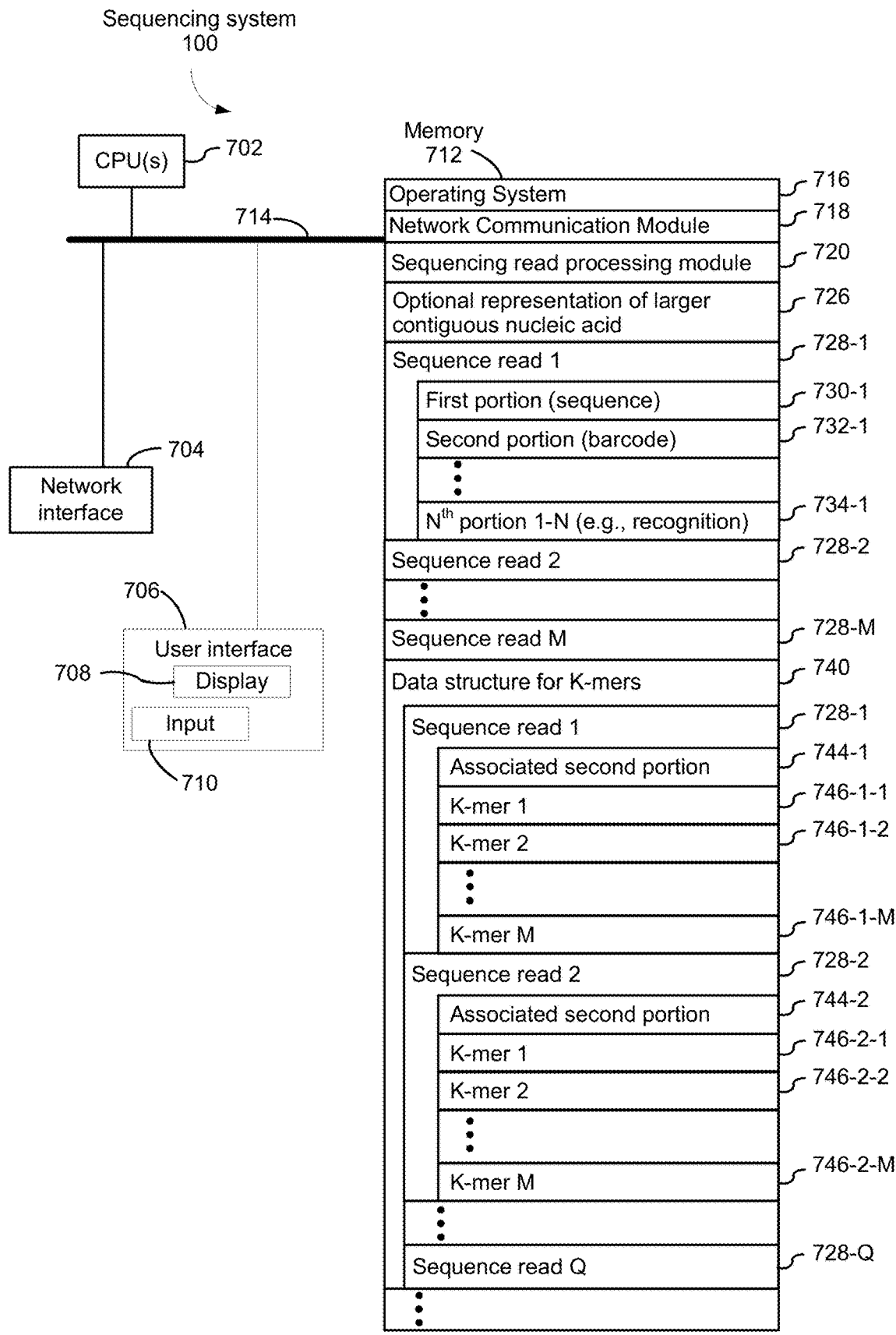
FIG. 7 is an example block diagram illustrating a computing device in accordance with some embodiments.

FIG. 7 is a block diagram illustrating a sequencing system 100 in accordance with some implementations. The device 100 in some implementations includes one or more processing units CPU(s) 702 (also referred to as processors), one or more network interfaces 704, a user interface 706, a memory 712, and one or more communication buses 714 for interconnecting these components. The communication buses 714 optionally include circuitry (sometimes called a chipset) that interconnects and controls communications between system components. The memory 712 typically includes high-speed random access memory, such as DRAM, SRAM, DDR RAM, ROM, EEPROM, flash memory, CD-ROM, digital versatile disks (DVD) or other optical storage, magnetic cassettes, magnetic tape, magnetic disk storage or other magnetic storage devices, other random access solid state memory devices, or any other medium which can be used to store desired information; and optionally includes non-volatile memory, such as one or more magnetic disk storage devices, optical disk storage devices, flash memory devices, or other non-volatile solid state storage devices. The memory 712 optionally includes one or more storage devices remotely located from the CPU(s) 702. The memory 712, or alternatively the non-volatile memory device(s) within the memory 712, comprises a non-transitory computer readable storage medium. In some implementations, the memory 712 or alternatively the non-transitory computer readable storage medium stores the following programs, modules and data structures, or a subset thereof:

- an operating system 716, which includes procedures for handling various basic system services and for performing hardware dependent tasks;
- a network communication module (or instructions) 718 for connecting the device 700 with other devices, or a communication network;
- a sequence read processing module 720 for processing sequence reads;
- an optional representation of a larger contiguous nucleic acid 726 obtained from a biological sample;
- a plurality of sequence reads 728, each respective sequence read in the plurality of sequence reads comprising at least a first portion 730 that corresponds to a subset of the larger contiguous nucleic acid and a common second portion 732 that forms an identifier that is independent of the sequence of the larger contiguous nucleic acid and that identifies a partition, in a plurality of partitions, in which the respective sequence read was formed; and
- a hash table 740 comprising, for each respective sequence read 728, the associated second portion 744 (bar code) and k-mers obtained by a hash of the respective sequence read 728 according to a predetermined k-mer length L In some implementations, the user interface 706 includes an input device (e.g., a keyboard, a mouse, a touchpad, a track pad, and/or a touch screen) 710 for a user to interact with the system 700 and a display 708.

In some implementations, one or more of the above identified elements are stored in one or more of the previously mentioned memory devices, and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory 712 optionally stores a subset of the modules and data structures identified above. Furthermore, in some embodiments, the memory stores additional modules and data structures not described above.

Although FIG. 7 shows a "sequence system 700," FIG. 7 is intended more as functional description of the various features which may be present in computer systems than as a structural schematic of the implementations described herein. In practice, and as recognized by those of ordinary skill in the art, items shown separately could be combined and some items could be separated.

Figure 8:
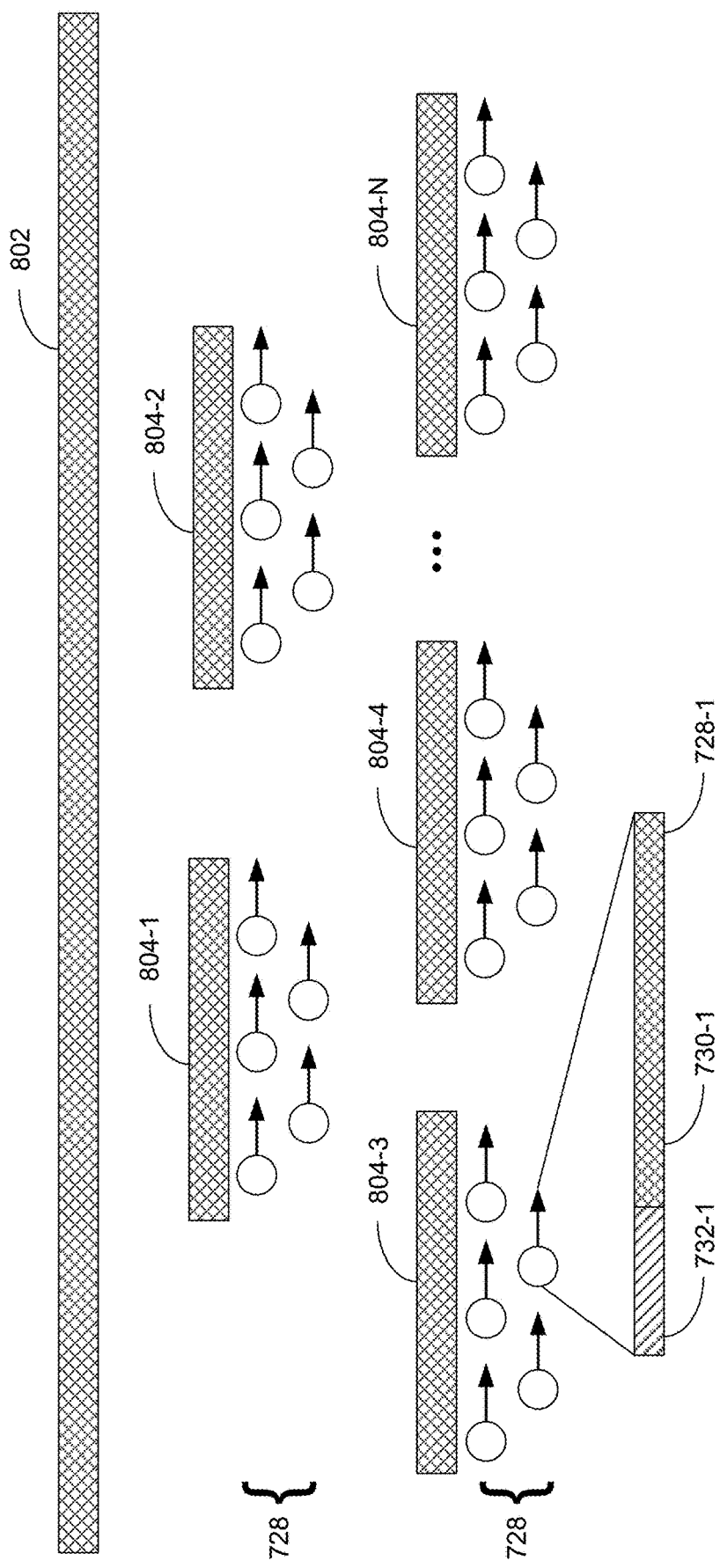
FIG. 8 illustrates the relationship between the larger contiguous nucleic acid, the different fragments of the larger contiguous nucleic acid, and sequence reads of fragments in accordance with some embodiments.

FIG. 8 illustrates the relationship between the larger contiguous nucleic acid 802, the different fragments 804 of the larger contiguous nucleic acid, and sequence reads 728 of fragments. Typically, between 1 and 250 fragments 804, between 5 and 500 fragments 804 or between 10 and 1000 fragments 804 are partitioned into a separate partition. In any event, sufficiently few of the fragments 804 are partitioned into the same partition such that the chance that the fragments 804 in a single partition have any appreciable overlapping sequences is unlikely. Sequence reads 728 of each fragment 804 are made. In typical embodiments, sequence reads 728 are short in length (e.g., less than 1000 bases) so that they can be sequenced in automated sequencers. Each sequence read 728 in a partition includes a common second portion 732 that forms an identifier that is independent of the sequence of the larger contiguous nucleic 802 acid nucleic acid and that identifies the partition, in a plurality of partitions, in which the respective sequence read was formed.

In some embodiments, a respective set of k-mers for each sequence read 728 in the plurality of sequence reads is constructed. In such embodiments the identifier (barcode 732) of the set of sequence reads that includes the sequence read is retained for each k-mer in the plurality of k-mers. K-mers are shorter than sequence reads. In some embodiments a sequence read is between 50 and 250 bases whereas a k-mer has a value of k (meaning that it has a nucleic acid length of k) that is between 7 and 51. Each respective set of k-mers includes at least eighty percent, at least eight-five percent, at least ninety percent, at least ninety-five percent of the possible k-mers of the corresponding sequence read.

FIG. 11 is a flow chart illustrating a method (1100) of sequencing a larger contiguous nucleic acid (e.g., obtained from a biological sample) (1102), in accordance with some embodiments. The method is performed at a computer system having one or more processors, and memory storing one or more programs for execution by the one or more processors (1104).

Obtaining a plurality of sequence reads. In accordance with the disclosed systems and methods, a plurality of sequence reads 728 is obtained (1106). The plurality of sequence reads comprises a plurality of sets of sequence reads. Each respective sequence read 728 in a set of sequence reads comprises a first portion (130) that corresponds to a subset of the larger contiguous nucleic acid and a common second portion (732) that forms an identifier that is independent of the sequence of the larger contiguous nucleic acid and that identifies a partition, in a plurality of partitions, in which the respective sequence read was formed. In other words, the identifier is not derived from, or a function of the sequencing data of the larger contiguous nucleic acid.

In some embodiments, as illustrated in FIG. 8, to obtain the plurality of sequence reads 728, a larger contiguous nucleic acid 802 is fragmented to form fragments 804 and these fragments are compartmentalized, or partitioned into discrete compartments or partitions (referred to interchangeably herein as partitions). In some embodiments, more than 10, more than 100, more than 1000, more than 10,000, more than 100,000, more than $1 \times 10^6$, or more than $5 \times 10^6$ sets of sequence reads are obtained, corresponding more than 10, more than 100, more than 1000, more than 10,000, more than 100,000, more than $1 \times 10^6$, or more than $5 \times 10^6$ partitions.

Each partition maintains separation of its own contents from the contents of other partitions. As used herein, the partitions refer to containers or vessels that may include a variety of different forms, e.g., wells, tubes, micro or nanowells, through holes, or the like. In preferred aspects, however, the partitions are flowable within fluid streams. In some embodiments, these vessels are comprised of, e.g., microcapsules or micro-vesicles that have an outer barrier surrounding an inner fluid center or core, or have a porous matrix that is capable of entraining and/or retaining materials within its matrix. In a preferred aspect, however, these partitions comprise droplets of aqueous fluid within a non-aqueous continuous phase, e.g., an oil phase. A variety of different suitable vessels are described in, for example, U.S. patent application Ser. No. 13/966,150, filed Aug. 13, 2013, which is hereby incorporated by reference herein in its entirety. Likewise, emulsion systems for creating stable droplets in non-aqueous or oil continuous phases are described in detail in, e.g., Published U.S. Patent Application No. 2010-0105112, which is hereby incorporated by reference herein in its entirety. In certain embodiments, microfluidic channel networks are particularly suited for generating partitions. Examples of such microfluidic devices include those described in detail in Provisional U.S. Patent Application No. 61/977,804, filed Apr. 4, 2014, the full disclosure of which is incorporated herein by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

In the case of droplets in an emulsion, partitioning the fragments 802 into discrete partitions may generally be accomplished by flowing an aqueous, sample containing stream, into a junction into which is also flowing a non-aqueous stream of partitioning fluid, e.g., a fluorinated oil, such that aqueous droplets are created within the flowing stream partitioning fluid, where such droplets include the sample materials. As described below, the partitions, e.g., droplets, also typically include co-partitioned barcode oligonucleotides.

The relative amount of sample materials within any particular partition may be adjusted by controlling a variety of different parameters of the system, including, for example, the concentration of fragments 804 in the aqueous stream, the flow rate of the aqueous stream and/or the non-aqueous stream, and the like. The partitions described herein are often characterized by having overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% of the above described volumes. In some cases, the use of low reaction volume partitions is particularly advantageous in performing reactions with small amounts of starting reagents, e.g., input larger contiguous nucleic acid fragments. Methods and systems for analyzing samples with low input nucleic acids are presented in U.S. Provisional Patent Application No. 62/017,580 Jun. 26, 2014, the full disclosure of which is hereby incorporated by reference in its entirety.

Once the fragments 804 are introduced into their respective partitions, the fragments 804 within partitions are generally provided with unique identifiers such that, upon characterization of those fragments 804, they may be attributed as having been derived from their respective partitions. In some embodiments, such unique identifiers are previously, subsequently or concurrently delivered to the partitions that hold the compartmentalized or partitioned fragments 804, in order to allow for the later attribution of the characteristics, e.g., nucleic acid sequence information, to the sample nucleic acids included within a particular compartment, and particularly to relatively long stretches of contiguous sample nucleic acids that may be originally deposited into the partitions.

Accordingly, the fragments 804 are typically co-partitioned with the unique identifiers 732 (e.g., barcode sequences). In particularly preferred aspects, the unique identifiers 732 are provided in the form of oligonucleotides that comprise nucleic acid barcode sequences 732. The oligonucleotides 732 are partitioned such that as between oligonucleotides in a given partition, the nucleic acid barcode sequences 732 contained therein are the same, but as between different partitions, the oligonucleotides can, and preferably have differing barcode sequences. In preferred embodiments, only one nucleic acid barcode sequence 732 is associated with a given partition, although in some embodiments, two or more different barcode sequences are present in a given partition.

The larger contiguous nucleic acid 802 is typically fragmented and partitioned such that the fragments 804 of the larger contiguous nucleic acid 802 in the partitions are long fragments or stretches of contiguous nucleic acid molecules. As illustrated in FIG. 8, these fragments 804 typically represent a number of overlapping fragments of the overall larger contiguous nucleic acid to be analyzed, e.g., an entire chromosome, exome, or other large genomic fragment.

The larger contiguous nucleic acid 802 is also typically fragmented and partitioned at a level whereby a given partition has a very low probability of including two overlapping fragments 804 of the starting larger contiguous nucleic acid 802. This is typically accomplished by providing the larger contiguous nucleic acid 802 at a low input amount and/or concentration during the partitioning process. As a result, in preferred cases, a given partition includes a number of long, but non-overlapping fragments 804 of the starting larger contiguous nucleic acid. The nucleic acid fragments in the different partitions are then associated with unique identifiers 732 where, for any given partition, fragments 804 contained therein possess the same unique identifier, but where different partitions include different unique identifiers. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multiwell plate. Further, because the systems described herein employ such high levels of barcode diversity, one can allocate diverse barcodes among higher numbers of genomic equivalents, as provided above. In some embodiments, in excess of 10,000, 100,000, 500,000, etc. diverse barcode types are used to achieve genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome. Here, each such genome is an example of a larger contiguous nucleic acid.

Figure 12A:
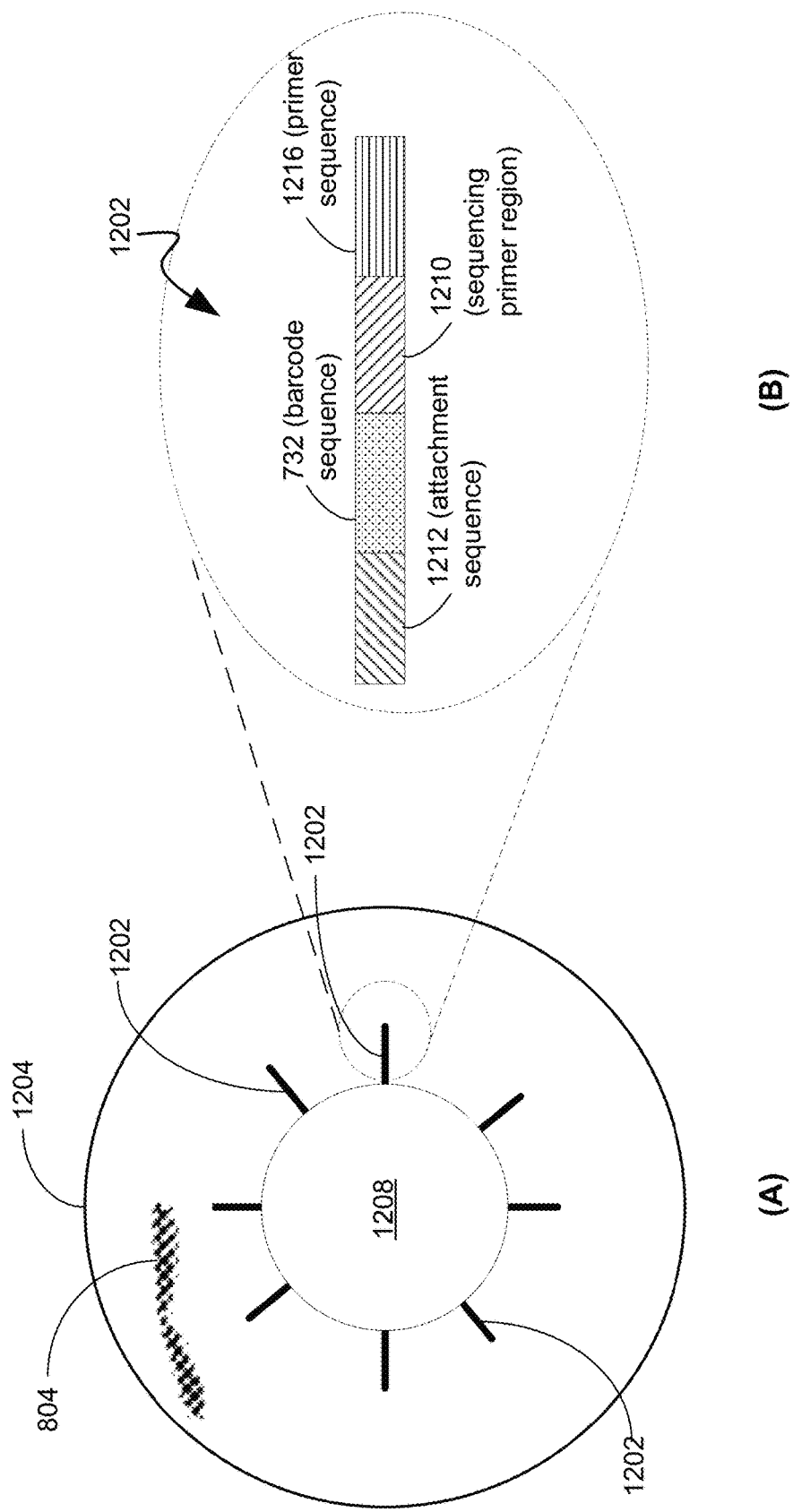

Referring to FIG. 12A, panel B, often the above-described partitioning is performed by combining the sample containing the larger contiguous nucleic acid 802 with a set of oligonucleotide tags 1202 (containing the barcodes 732) that are releasably-attached to beads prior to the partitioning step. The oligonucleotides 1202 may comprise at least a primer region 1210 and a barcode 732 region. Between oligonucleotides 1202 within a given partition, the barcode region 732 is substantially the same barcode sequence, but as between different partitions, the barcode region 732 in most cases is a different barcode sequence. In some embodiments, the primer region includes (or further comprises) an N-mer 1216 (either a random N-mer or an N-mer designed to target a particular sequence) that is used to prime the fragments 804 within the partitions. In some cases, where the N-mer is designed to target a particular nucleic acid sequence, the primer region 1210 is designed to target a particular chromosome (e.g., human chromosome 1, 2, 3, 4, 5, 6, 7, 8, 9, 10, 11, 12, 13, 14, 15, 16, 17, 18, 19, 20, 21, 22, X, or Y), or region of a chromosome, e.g., an exome or other targeted region. In some cases, the N-mer is designed to target a particular gene or genetic region, such as a gene or region associated with a disease or disorder (e.g., cancer). In some cases, the N-mer is designed to target a particular structural variation. Within the partitions, an amplification reaction is conducted using the primer sequence 1210/1216 (e.g. N-mer) to prime the fragments 804 at different places along their lengths. As a result of the amplification, each partition contains amplified products of the fragments 804, termed sequence reads 728, that comprise an identical or near-identical (common) barcode 732, and that represent overlapping, smaller fragments of the fragments 804 in each partition. The barcode 732 therefore serves as a marker that signifies that a set of sequence reads 728 originated from the same partition, and thus potentially also originated from the same fragment 804. It will be appreciated that there are typically several fragments 804 in any given partition. Nevertheless, in typical embodiments, fragments 804 that are in the same partition typically do not have any significant overlap and so it is possible to localize the amplified sequence reads 728 to the correct fragment 804 in any given partition. Following amplification, the sequence reads 728 are pooled, sequenced, and aligned using a sequencing algorithm. Because shorter sequence reads 728 may, by virtue of their associated barcode sequences 732, be aligned and attributed to a single, long fragment 804 of the larger contiguous nucleic acid 802, all of the identified variants on that sequence can be attributed to a single originating fragment 802 and single originating chromosome of the larger contiguous nucleic acid. Further, by aligning multiple co-located variants across multiple fragments 804, one can further characterize that chromosomal contribution. Accordingly, conclusions regarding the phasing of particular genetic variants may then be drawn. Such information may be useful for identifying haplotypes, which are generally a specified set of genetic variants that reside on the same nucleic acid strand or on different nucleic acid strands. Moreover, additionally or alternatively, structural variants are identified.

In some embodiments, referring to FIG. 12A, the co-partitioned oligonucleotides 1202 also comprise functional sequences in addition to the barcode sequence 732 and the primer region sequence 1210/1216. For instance, in some embodiments, the co-partitioned oligonucleotides 1202 also comprise other functional sequences useful in the processing of the partitioned nucleic acids such as targeted or random/universal amplification primer sequences for amplifying the fragments 804 within the partitions while attaching the associated barcode sequences, sequencing primers, hybridization or probing sequences, e.g., for identification of presence of the sequences, or for pulling down barcoded nucleic acids, or any of a number of other potential functional sequences. See, for example, the disclosure on co-partitioning of oligonucleotides and associated barcodes and other functional sequences, along with sample materials as described in, for example, U.S. Patent Application Nos. 61/940,318, filed Feb. 7, 2014, 61/991,018, Filed May 9, 2014, and U.S. patent application Ser. No. 14/316,383, filed on Jun. 26, 2014, as well as U.S. patent application Ser. No. 14/175,935, filed Feb. 7, 2014, the full disclosures of which is hereby incorporated by reference in their entireties.

In one exemplary process, beads are provided that each includes large numbers of the above described oligonucleotides 1202 releasably attached to the beads, where all of the oligonucleotides attached to a particular bead include the same nucleic acid barcode sequence 732, but where a large number of diverse barcode sequences are represented across the population of beads used. Typically, the population of beads provides a diverse barcode sequence library that includes at least 1000 different barcode sequences, at least 10,000 different barcode sequences, at least 100,000 different barcode sequences, or in some cases, at least 1,000,000 different barcode sequences. Additionally, each bead typically is provided with large numbers of oligonucleotide molecules 1202 attached. In particular, the number of molecules of oligonucleotides 1202 including the barcode sequence 732 on an individual bead may be at least about 10,000 oligonucleotides, at least 100,000 oligonucleotide molecules, at least 1,000,000 oligonucleotide molecules, at least 100,000,000 oligonucleotide molecules, and in some cases at least 1 billion oligonucleotide molecules.

In some embodiments, the oligonucleotides are releasable from the beads upon the application of a particular stimulus to the beads. In some cases, the stimulus is a photo-stimulus, e.g., through cleavage of a photo-labile linkage that may release the oligonucleotides. In some cases, a thermal stimulus is used, where elevation of the temperature of the beads environment results in cleavage of a linkage or other release of the oligonucleotides form the beads. In some cases, a chemical stimulus is used that cleaves a linkage of the oligonucleotides to the beads, or otherwise results in release of the oligonucleotides from the beads.

In some embodiments, the beads including the attached oligonucleotides 1202 are co-partitioned with the individual samples, such that a single bead and a single sample are contained within an individual partition. In some cases, where single bead partitions are desired, it may be desirable to control the relative flow rates of the fluids such that, on average, the partitions contain less than one bead per partition, in order to ensure that those partitions that are occupied, are primarily singly occupied. Likewise, in some embodiments, the flow rate is controlled to provide that a higher percentage of partitions are occupied, e.g., allowing for only a small percentage of unoccupied partitions. In preferred aspects, the flows and channel architectures are controlled as to ensure a desired number of singly occupied partitions, less than a certain level of unoccupied partitions and less than a certain level of multiply occupied partitions.

Figure 4:
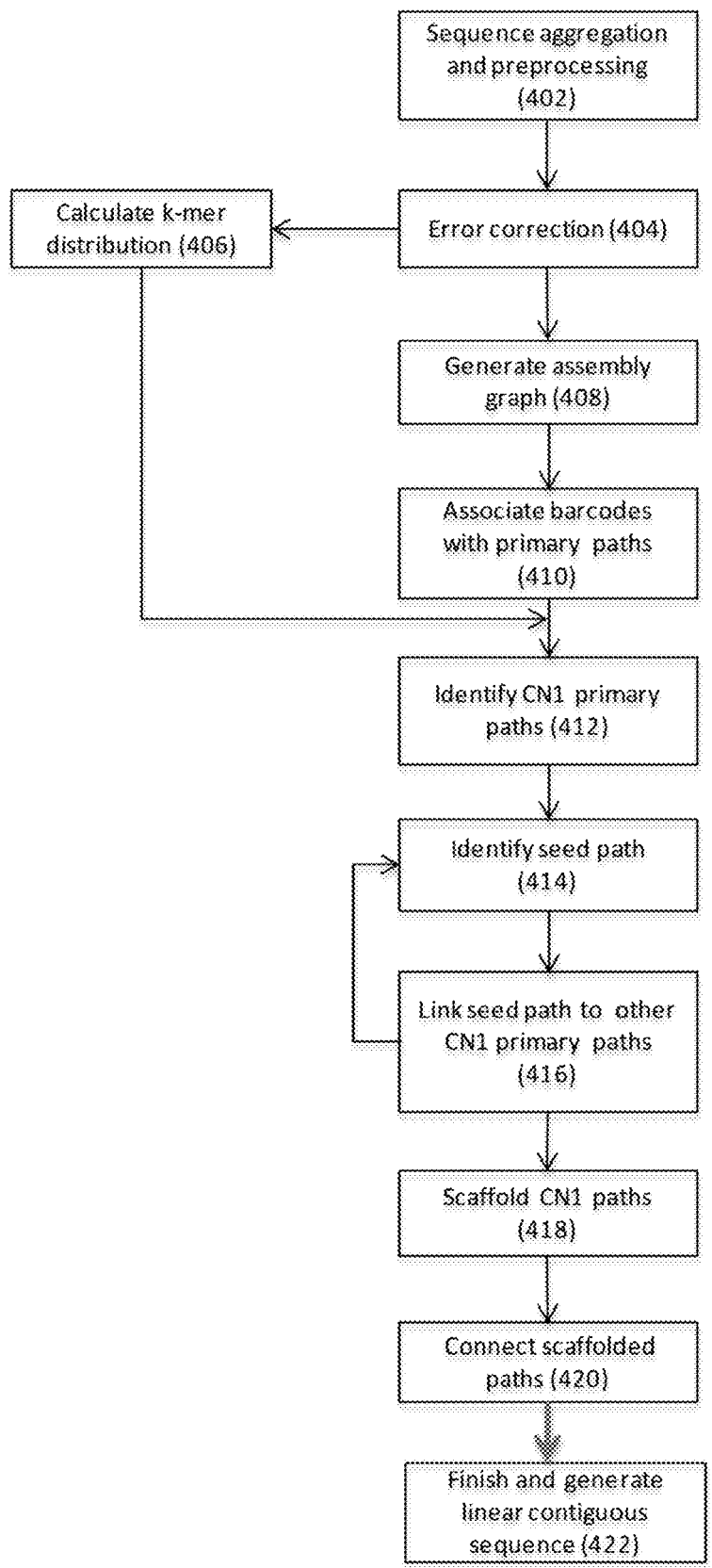
FIG. 4 schematically illustrates a process for genome assembly in accordance with some embodiments.

FIG. 3 of U.S. Patent Application No. 62/072,214, filed Oct. 29, 2014, entitled "Analysis of Nucleic Acid Sequences," which is hereby incorporated by reference and the portions of the specification describing FIG. 3 provide a detailed example of one method for barcoding and subsequently sequencing a larger contiguous nucleic acid (referred to in the reference as a "sample nucleic acid") in accordance with one embodiment of the present disclosure. As noted above, while single bead occupancy may be the most desired state, it will be appreciated that multiply occupied partitions, or unoccupied partitions may often be present. FIG. 4 of U.S. Patent Application No. 62/072,214, filed Oct. 29, 2014, entitled "Analysis of Nucleic Acid Sequences," which is hereby incorporated by reference, and the portions of the specification describing FIG. 4 provide a detailed example of a microfluidic channel structure for co-partitioning samples and beads comprising barcode oligonucleotides in accordance with one embodiment of the present disclosure.

Once co-partitioned, the oligonucleotides 1202 disposed upon the bead are used to barcode and amplify the partitioned samples. One process for use of these barcoded oligonucleotides 1202 in amplifying and barcoding samples is described in detail in U.S. Patent Application Nos. 61/940, 318, filed Feb. 7, 2014, 61/991,018, filed May 9, 2014, and Ser. No. 14/316,383, filed on Jun. 26, 2014, the full disclosures of which are hereby incorporated by reference in their entireties. Briefly, in one aspect, the oligonucleotides present on the beads that are co-partitioned with the samples are released from their beads into the partition with the samples. The oligonucleotides typically include, along with the barcode sequence 732, a primer sequence at its 5' end 1216. In some embodiments, this primer sequence is a random oligonucleotide sequence intended to randomly prime numerous different regions of the samples. In some embodiments the primer sequence 1216 is a specific primer sequence targeted to prime upstream of a specific targeted region of the sample.

Once released, the primer portion 1216 of the oligonucleotide 1202 anneals to a complementary region of fragments 804 in the partition. Extension reaction reagents, e.g., DNA polymerase, nucleoside triphosphates, co-factors (e.g., $Mg^{2+}$ or $Mn^{2+}$ etc.), that are also co-partitioned with the fragments 804 and beads, extend the primer sequence using the fragments 804 as a template, to produce a complementary sequence to the strand of the fragment 804 to which the primer annealed, and this complementary sequence includes the oligonucleotide 1202 and its associated barcode sequence 732. Annealing and extension of multiple primers to different portions of the fragments 804 in the partition may result in a large pool of overlapping complementary portions of the fragments 804, each possessing its own barcode sequence 732 indicative of the partition in which it was created. In some cases, these complementary portions may themselves be used as a template primed by the oligonucleotides 1202 present in the partition to produce a complement of the complement that again, includes the barcode sequence 732. In some cases, this replication process is configured such that when the first complement is duplicated, it produces two complementary sequences at or near its termini, to allow the formation of a hairpin structure or partial hairpin structure that reduces the ability of the molecule to be the basis for producing further iterative copies. A schematic illustration of one example of this is shown in FIG. 12.

As FIG. 12A shows, oligonucleotides 1202 that include a barcode sequence 732 are co-partitioned in, e.g., a droplet 1204 in an emulsion, along with a sample fragment 306. In some embodiments, the oligonucleotides 302 are provided on a bead 1208 that is co-partitioned with the larger contiguous nucleic acid fragment 804. The oligonucleotides 1202 are preferably releasable from the bead 1208, as shown in FIG. 12A, panel (A). As shown in FIG. 12A panel (B), the oligonucleotides 1202 includes a barcode sequence 732, in addition to one or more functional sequences, e.g., sequences 1212, 732, 1210, and 1216. For example, the oligonucleotide 1202 is shown as further comprising sequence 1212 that may function as an attachment or immobilization sequence for a given sequencing system, e.g., a P5 sequence used for attachment in flow cells of an ILLUMINA, HISEQ or MISEQ system. In other words, attachment sequence 1212 is used to reversibly attach oligonucleotide 1202 to a bead 1208 in some embodiments. As shown in FIG. 12A, panel B, the oligonucleotide 1202 also includes a primer sequence 1210, which may include (or further comprise) a random or targeted N-mer 1216 (discussed above) for priming replication of portions of the fragment 804. Also included within exemplary oligonucleotide 1202 of FIG. 12A, panel B, is a sequence 1210 which may provide a sequencing priming region, such as a "read1" or R1 priming region, that is used to prime polymerase mediated, template directed sequencing by synthesis reactions in sequencing systems. In many cases, the barcode sequence 732, and immobilization sequence 1212 may be common to all of the oligonucleotides 1202 attached to a given bead. The primer sequence 1210/1216 may vary for random N-mer primers, or may be common to the oligonucleotides on a given bead for certain targeted applications.

Figure 12B:
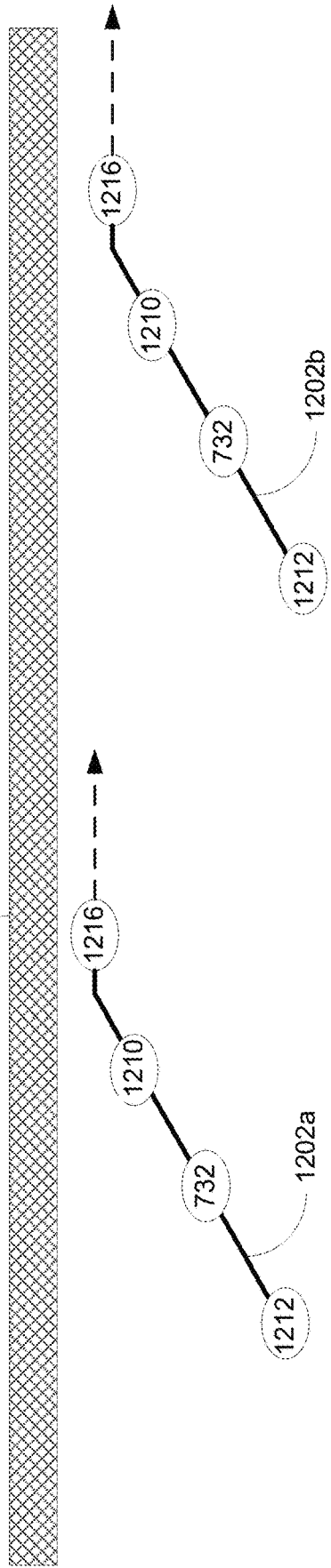

Referring to FIG. 12B, based upon the presence of primer sequence 1216, the oligonucleotides 1202a and 1202b are able to prime the fragment 804, which allows for extension of the oligonucleotides 1202a and 1202b using polymerase enzymes and other extension reagents also co-portioned with the bead 1208 and fragment 804.

Figure 12C:
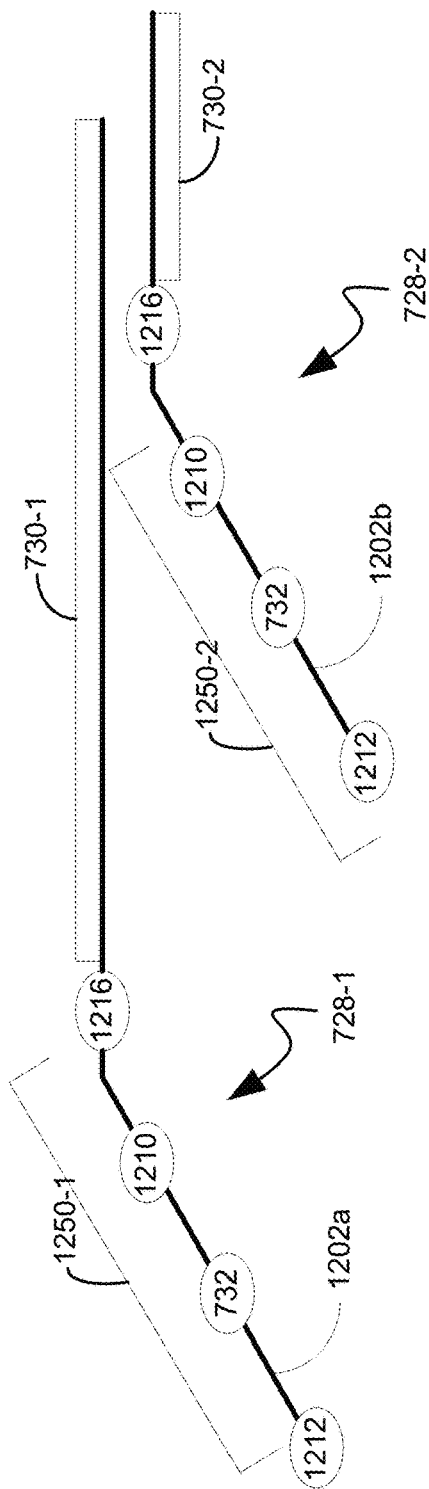

As shown in FIG. 12C, following extension of the oligonucleotides that, for random N-mer primers, would anneal to multiple different regions of the fragment 804; multiple overlapping complements of the fragment 804 are created, e.g., sequence reads 728-1 and 728-2. As such, FIG. 12C illustrates (A) obtaining a plurality of sequence reads, where each respective sequence read 728 in the plurality of sequence reads comprises a first portion 730 that corresponds to a subset of the larger contiguous nucleic acid 802 and a common second portion 1250 that that forms an identifier 732 that is independent of the sequence of the larger contiguous nucleic acid and that identifies a partition, in a plurality of partitions, in which the respective sequence read 728 was formed (e.g., bar code 732).

Figure 12D:
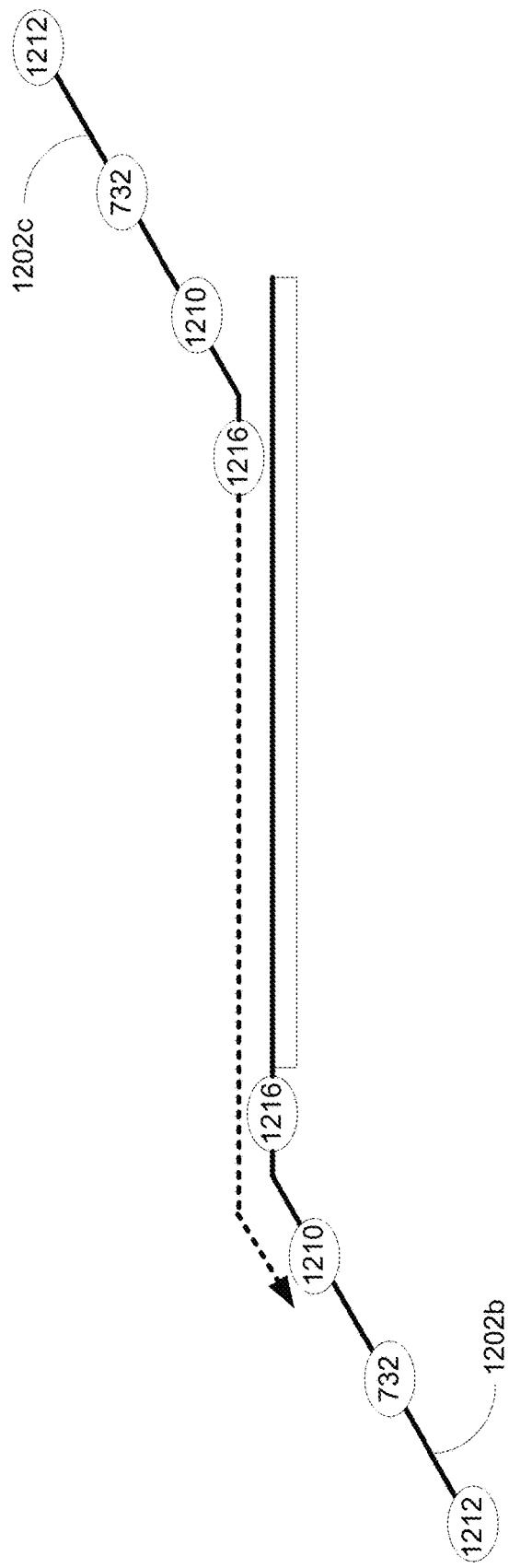
Figure 12E:
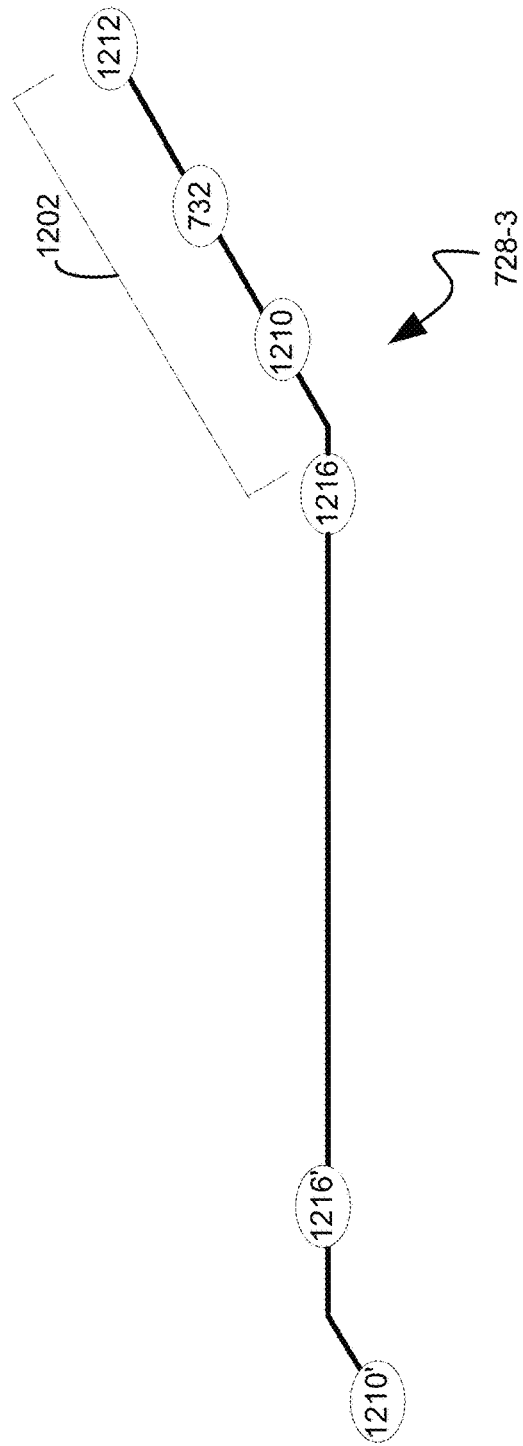

The barcoded sequence reads 728 of FIG. 12B may then be subjected to characterization, e.g., through sequence analysis, or they may be further amplified in the process, as shown in FIG. 12D. For example, additional oligonucleotides, e.g., oligonucleotide 1202c, also released from bead 1208, may prime the fragment 1202b. In particular, again, based upon the presence of the random N-mer primer 1216 in oligonucleotide 1202c (which in many cases will be different from other random N-mers in a given partition) the oligonucleotide anneals with the fragment 1202b, and is extended to create a complement 728-3 to at least a portion of fragment 1202b which comprises a duplicate of a portion of the larger contiguous nucleic acid sequence. Extension of the oligonucleotide 1202b continues until it has replicated through the oligonucleotide portion 730 of fragment 1202b. As illustrated in FIG. 12D, the oligonucleotides may be configured to promptly stop in the replication by the polymerase at a desired point, e.g., after replicating through sequences 1216 and 1210 of oligonucleotide 1202b. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 1210 to prevent a non-uracil tolerant polymerase to cease replication of that region. As a result, referring to FIG. 12E, a sequence read 728-3 is created that includes the full-length oligonucleotide 1202 at one end, including the barcode sequence 732, the attachment sequence 1212, the primer region 1210, and the random N-mer sequence 1216. At the other end of the sequence is included the complement 1216' to the random N-mer of the first oligonucleotide 1202, as well as a complement to all or a portion of the primer sequence, shown as sequence 1210'. The R1 sequence 1210 and its complement 1210' are then able to hybridize together to form a partial hairpin structure 1260. As will be appreciated, because the random N-mers differ among different oligonucleotides, these sequences and their complements would not be expected to participate in hairpin formation, e.g., sequence 1216', which is the complement to random N-mer 1216, would not be expected to be complementary to random N-mer sequence 1216b. This would not be the case for other applications, e.g., targeted primers, where the N-mers would be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 730-3.

All of the sequence reads 728 from multiple different partitions may then be pooled for sequencing on high throughput sequencers as described herein. Because each sequence read 728 is coded as to its partition of origin, the sequence of that sequence read 728 may be attributed back to its origin based upon the presence of the barcode 732.

Figure 13:
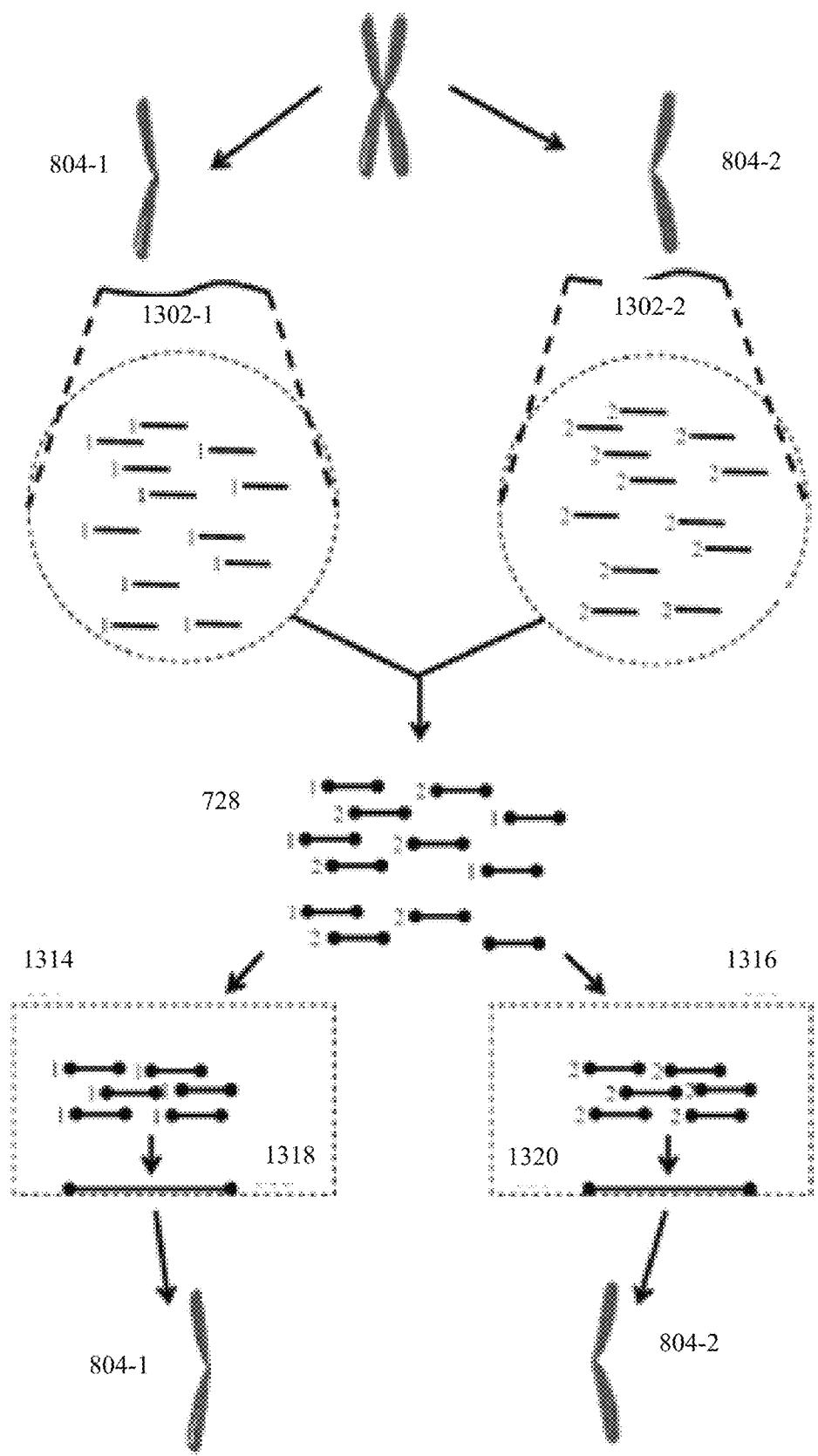
FIG. 13 illustrates a method for obtaining a plurality of sequence reads and pooling them together in accordance with some embodiments.

This is schematically illustrated in FIG. 13. As shown in one example, a fragment 804-1 and a fragment 804-2 are each partitioned along with their own sets of barcode oligonucleotides 1202 as described above. Within each partition, each fragment (804-1 and 804-2) is then processed to separately to provide overlapping sequence reads 728 of the fragments 804-1 and 804-2, to form set of sequence reads 1302-1 and 1302-2. This processing provides sequence reads 728 with a barcode sequence 732 that is the same for each of the sequence reads 728 derived from a particular first fragment 804. As shown, the set of sequence reads 1302-1 is denoted by "1" while the set of sequence reads 1302-2 is denoted by "2". A diverse library of barcodes may be used to differentially barcode large numbers of different sets of sequence reads. However, it is not necessary for every sequence read in a given partition to be barcoded with different barcode sequence. In fact, in many cases, multiple different fragments 804 may be processed concurrently in the same partition to include the same barcode sequence 732. Diverse barcode libraries are described in detail elsewhere herein.

The sets of sequence reads may then be pooled for sequencing using, for example, sequence by synthesis technologies available from Illumina or Ion Torrent division of Thermo Fisher, Inc. Once sequenced, the sequence reads 728 can be attributed to their respective fragment 804 set, e.g., as shown in aggregated reads 1314 and 1316, at least in part based upon the included barcodes, and optionally, and preferably, in part based upon the sequence of the fragment itself. The attributed sequence reads for each fragment set are then assembled to provide the assembled sequence for each sample fragment, e.g., sequences 1318 and 1320, which in turn, may be further attributed back to their respective original fragments 804. Methods and systems for assembling genomic sequences are described in, for example, U.S. Provisional Patent Application No. 62/017,589, filed Jun. 26, 2014, the full disclosure of which is hereby incorporated by reference in its entirety.

Figure 11A:
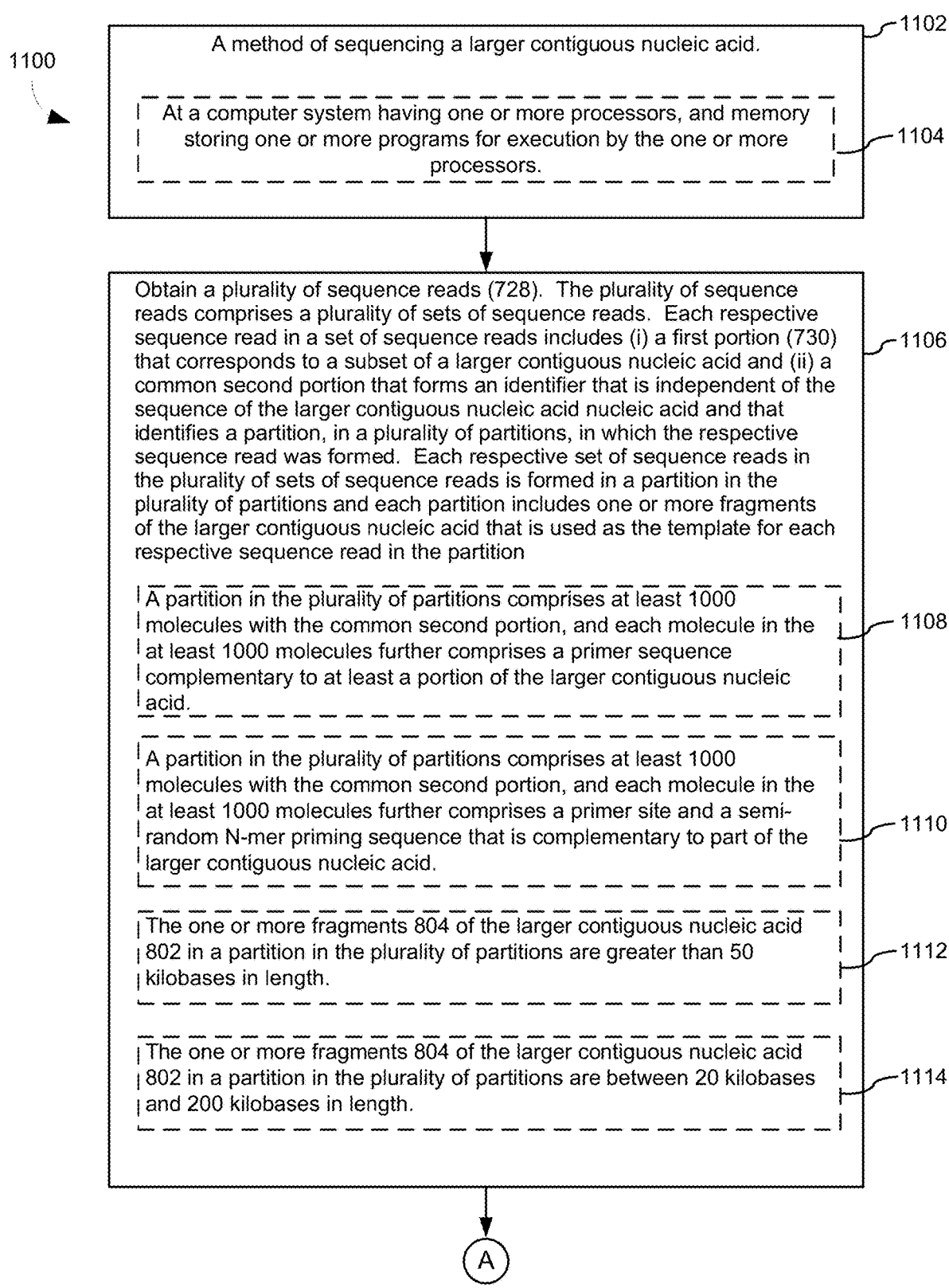

Referring to FIG. 11A (1108), in some embodiments, a partition in the plurality of partitions comprises at least 10 molecules, at least 100 molecules, at least 1000 molecules, at least $1 \times 10^4$ molecules, at least $1 \times 10^5$ molecules, at least $1 \times 10^6$ molecules, at least $1 \times 10^7$ molecules, or at least $1 \times 10^8$ molecules with the common second portion 732. In other words, the partition includes at least at least 10 molecules, at least 100 molecules, at least 1000 molecules, at least $1 \times 10^4$ molecules, at least $1 \times 10^5$ molecules, at least $1 \times 10^6$ molecules, at least $1 \times 10^7$ molecules, or at least $1 \times 10^8$ molecules 1202 (FIG. 12A), and each such molecule 1202 further comprises a primer sequence 1210 complementary to at least a portion of the larger contiguous nucleic acid 802.

Referring to FIG. 11A (1110), in some embodiments, a partition in the plurality of partitions comprises at least 10 molecules, at least 100 molecules, at least 1000 molecules, at least $1 \times 10^4$ molecules, at least $1 \times 10^5$ molecules, at least $1 \times 10^6$ molecules, at least $1 \times 10^7$ molecules, or at least $1 \times 10^8$ molecules with the common second portion 732, and each such molecule 1202 further comprises a primer site 1210 and a semi-random N-mer priming sequence 1216 that is complementary to part of the larger contiguous nucleic acid (1110).

Referring to FIG. 11A (1112), in some embodiments, each fragment 804 in the one or more fragments of the larger contiguous nucleic acid 802 in a partition in the plurality of partitions is greater than 1 kilobase in length, is greater than 5 kilobases in length, is greater than 50 kilobases in length, is greater than 100 kilobases in length, is greater than 200 kilobases in length, is greater than 250 kilobases in length, is greater than 300 kilobases in length, or is greater than 350 kilobases in length. Typically, the fragments 804 of the larger contiguous nucleic acid 802 that are partitioned into partitions are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb. In some embodiments the one or fragments in a partition in the plurality of partitions have an N50 (where the sum of the fragment 804 lengths that are greater than the stated N50 number is 50% of the sum of all fragment 804 lengths) of at least about 10 kb, at least about 20 kb, at least about 50 kb, at least about 100 kb, at least about 150 kb, at least about 200 kb, at least about 250 kb, at least about 300 kb, at least about 350 kb, at least about 400 kb, at least about 500 kb, in excess of 1 Mb, or even in excess of 2 Mb. In some embodiments the one or fragments in each partition across the plurality of partitions have an overall N50 (where the sum of the fragment 804 lengths that are greater than the stated N50 number is 50% of the sum of all fragment 804 lengths) of at least about 10 kb, at least about 20 kb, at least about 50 kb, at least about 100 kb, at least about 150 kb, at least about 200 kb, at least about 250 kb, at least about 300 kb, at least about 350 kb, at least about 400 kb, at least about 500 kb, in excess of 1 Mb, or even in excess of 2 Mb. In some embodiments, the one or more fragments 804 of the larger contiguous nucleic acid 802 in a partition in the plurality of partitions are between 20 kilobases and 200 kilobases in length (1114). In some embodiments, the one or more fragments of the larger contiguous nucleic acid in a partition in the plurality of partitions are between 20 kilobases and 200 kilobases in length (1116).

Referring to FIG. 11B (1118), in some embodiments, the one or more fragments 804 of the larger contiguous nucleic acid in a partition in the plurality of partitions consists of between 1 and 500 different fragments, between 10 and 1000 different fragments, between 100 and 1000 different fragments, between 25 and 150 different fragments, between 5 and 500 different fragments, between 25 and 400 different fragments, between 100 and 10,000 different fragments, between 50 and 250 different fragments, or between 2 and 125 different fragments of the larger contiguous nucleic acid (1118). In some embodiments, the one or more fragments 804 of the larger contiguous nucleic acid in a partition in the plurality of partitions comprises more than 2 different fragments 804, more than 10 different fragments 804, more than 20 different fragments 804, more than 50 different fragments 804, more than 100 different fragments 804, more than 200 different fragments 804, more than 300 different fragments 804, more than 400 different fragments 804, or more than 500 different fragments 804 of the larger contiguous nucleic acid (1118). In a specific embodiment, the one or more fragments 804 of the larger contiguous nucleic acid 802 in a partition in the plurality of partitions consists of between 5 and 100 fragments 804 of the larger contiguous nucleic acid 802 (1120).

Referring to FIG. 11B (1122), in some embodiments, the plurality of sequence reads is obtained from less than 5 nanograms of nucleic or ribonucleic acid. That is, the total amount of nucleic acid 804 needed for the plurality of partitions is advantageously less than 5 nanograms in some embodiments. In varying embodiments in accordance with the present disclosure, the plurality of sequence reads is obtained from less than 500 nanograms of nucleic or ribonucleic acid, less than 250 nanograms of nucleic or ribonucleic acid, less than 50 nanograms of nucleic or ribonucleic acid, less than 5 nanograms of nucleic or ribonucleic acid, or less than 2 nanograms of nucleic or ribonucleic acid.

Referring to FIG. 11B (1124), in some embodiments, the identifier in the second portion 732 of each respective sequence read 728 in the set of sequence reads encodes a common value selected from the set $\{1, \ldots, 1024\}$, the set $\{1, \ldots, 4096\}$, the set $\{1, \ldots, 16384\}$, the set $\{1, \ldots, 65536\}$, the set $\{1, \ldots, 262144\}$, the set $\{1, \ldots, 1048576\}$, the set $\{1, \ldots, 4194304\}$, the set $\{1, \ldots, 16777216\}$, the set $\{1, \ldots, 67108864\}$, or the set $\{1, \ldots, 1\times10^{12}\}$. For instance, consider the case in which the identifier is represented by a set of five nucleotide positions. In this instance, each nucleotide position contributes four possibilities (A, T, C or G), giving rise, when all five positions are considered, to 4×4×4×4×4=1024 possibilities. As such, the five nucleotide positions form the basis of the set $\{1, \ldots, 1024\}$. Thus, when the barcode sequence is a 5-mer, the second portion 732 of each sequencing read 728 encodes a unique predetermined value selected from the set $\{1, \ldots, 1024\}$. Likewise, when the barcode sequence is represented by a set of six nucleotide positions, the six nucleotide positions collectively contribute 4×4×4×4×4×4=4096 possibilities. As such, the six nucleotide positions form the basis of the set $\{1, \ldots, 4096\}$. In other words, when the barcode sequence is a 6-mer, the second portion 732 of each sequencing read 128 encodes a unique predetermined value selected from the set $\{1, \ldots, 4096\}$. In some embodiments, the identifier is an N-mer, and N is an integer selected from the set $\{4, \ldots, 20\}$ (1126).

In some embodiments, the identifier 732 of a sequencing read 728 in the plurality of sequencing reads is localized to a contiguous set of oligonucleotides within the sequencing read. In one such exemplary embodiment, the contiguous set of oligonucleotides is an N-mer, where N is an integer selected from the set $\{4, \ldots, 20\}$ (214). In other words, in some embodiments, the barcode 732 in, for instance FIG. 12A, panel B, is a contiguous set of nucleotide positions (e.g., 4 contiguous nucleotide positions, 5 contiguous nucleotide positions, 6 contiguous nucleotide positions, 7 contiguous nucleotide positions, 8 contiguous nucleotide positions, 9 contiguous nucleotide positions, 10 contiguous nucleotide positions, 11 contiguous nucleotide positions, 12 contiguous nucleotide positions, 13 contiguous nucleotide positions, 14 contiguous nucleotide positions, 15 contiguous nucleotide positions, 16 contiguous nucleotide positions, 17 contiguous nucleotide positions, 18 contiguous nucleotide positions, 19 contiguous nucleotide positions, or 20 contiguous nucleotide positions) within oligonucleotide tag 1202 which ultimately becomes second portion 732 upon transcription of the larger contiguous nucleic acid.

By contrast, in some embodiments, the identifier in the second portion of a sequencing read in the plurality of sequencing reads is localized to a noncontiguous set of oligonucleotides within the sequencing read. In one such exemplary embodiment, the predetermined noncontiguous set of nucleotides collectively consists of N nucleotides, where N is an integer in the set $\{4, \ldots, 20\}$. As an example, in some embodiments, referring to FIG. 12A, panel B, barcode sequence 732 comprises a first set of contiguous nucleotide positions at a first position in oligonucleotide tag 1202 and a second set of contiguous nucleotide positions at a second position in oligonucleotide tag 120, that is displaced from the first set of contiguous nucleotide positions by a spacer. In one specific example, the barcode sequence 732 comprises $(X1)_n Y_z (X2)_m$, where X1 is n contiguous nucleotide positions, Y is a constant predetermined set of z contiguous nucleotide positions, and X2 is m contiguous nucleotide positions. In this example, the identifier in the second portion of the sequencing read 728 produced by a schema invoking this exemplary barcode is localized to a noncontiguous set of oligonucleotides, namely $(X1)_n$ and $(X2)_m$. This is just one of many examples of noncontiguous formats for barcode sequence within the scope of the present disclosure.

The nucleic acid barcode sequences 732 will typically include from 6 to about 20 or more nucleotides within the sequence of the oligonucleotides. In some embodiments, these nucleotides are completely contiguous, e.g., in a single stretch of adjacent nucleotides. In alternative embodiments, they are separated into two or more separate subsequences that are separated by one or more nucleotides. Typically, separated subsequences are separated by about 4 to about 16 intervening nucleotides.

Referring to FIG. 11B (1128 and 1130), in some embodiments, an average sequence read length of the plurality of sequence reads is between 40 bases and 200 bases (1128), between 40 bases and 200 bases, between 60 bases and 140 bases, or between 30 bases and 130 bases. In some embodiments the sequence reads have a sequence length that is compatible with the flow cells of ILLUMINA, HISEQ, MISEQ or related systems.

In some embodiments, the plurality of sequence reads, in the aggregate, have an N50 (where the sum of the sequence read lengths that are greater than the stated N50 number is 50% of the sum of all sequence read lengths) of at least about 10 kb, at least about 20 kb, or at least about 50 kb. In some aspects, sequence read lengths having an N50 of at least about 100 kb, at least about 150 kb, at least about 200 kb, and in many cases, at least about 250 kb, at least about 300 kb, at least about 350 kb, at least about 400 kb, and in some cases, or at least about 500 kb or more, are attained. In still other cases, maximum sequence read lengths in excess of 200 kb, in excess of 300 kb, in excess of 400 kb, in excess of 500 kb, in excess of 1 Mb, or even in excess of 2 Mb are obtained in accordance with the present disclosure.

Figure 11C:
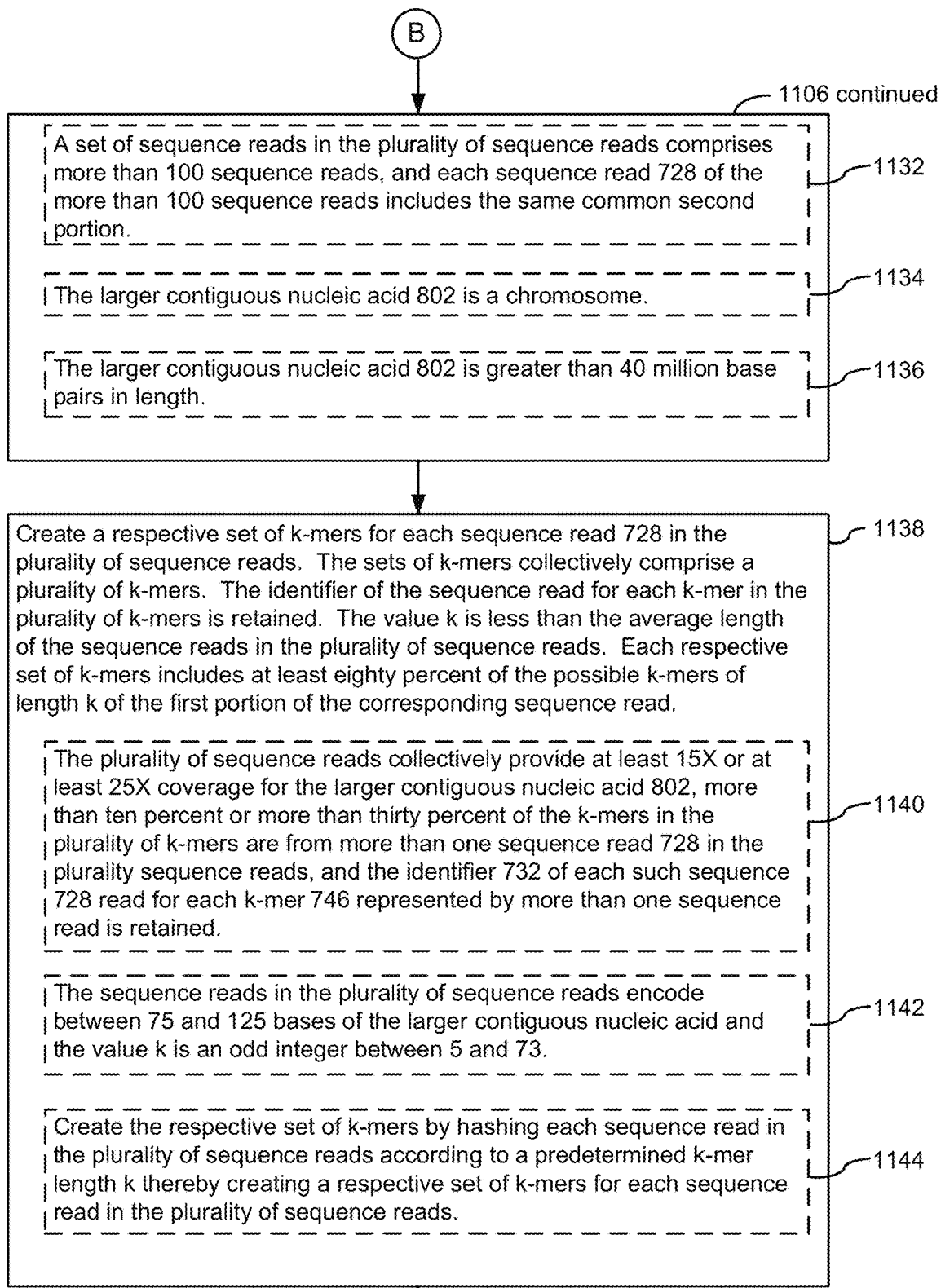

Referring to FIG. 11C (1128 and 1130), in some embodiments, a set of sequence reads in the plurality of sequence reads comprises more than 100 sequence reads, and each sequence read 728 of the more than 100 sequence reads includes the same common second portion (1132). That is, a given partition in the plurality of partitions yields 100 sequence reads and each such sequence read 728 has the same identifier 732. More generally, in some embodiments, a set of sequence reads in the plurality of sequence reads comprises more than 10 sequence reads, more than 200 sequence reads, more than 500 sequence reads, more than 1000 sequence reads, more than 2500 sequence reads, or more than 5000 sequence reads and each such sequence read 728 includes the same common second portion (the same identifier 732).

Referring to FIG. 11C (1134, 1136), in some embodiments, the larger contiguous nucleic acid 802 is a chromosome (1134). In some embodiments, the larger contiguous nucleic acid 802 is the genome of a multi-chromosomal organism such as a human. In some embodiments, the larger contiguous nucleic acid 802 includes whole genomes, individual chromosomes, exomes, amplicons, or any of a variety of different nucleic acids of interest. In some embodiments, the larger contiguous nucleic acid 802 is greater than 40 million base pairs in length (1136). In some embodiments, the larger contiguous nucleic acid 802 is greater than 100,000 base pairs in length, is greater than 1 million base pairs in length, is greater than 5 million base pairs in length, is greater than 10 million base pairs in length, is greater than 20 million base pairs in length, is greater than 30 million base pairs in length, or is greater than 50 million base pairs in length.

Create a set of k-mers. Referring to FIG. 11C (1138), once the plurality of sequence reads is obtained, a respective set of k-mers is created for each sequence read 728 in the plurality of sequence reads. Taken together, the sets of k-mers collectively comprise a plurality of k-mers. That is, the sets of k-mers from the plurality of sequence reads are pooled to form a plurality of k-mers. Importantly, the identifier 732 of the source sequence read 728 for each k-mer 746 in the plurality of k-mers is retained. For instance, a data structure that lists, for each respective k-mer 746 observed, the barcodes (second portions) 732 of the sequence reads 728 that contain the respective k-mer is used in some embodiments of the present disclosure. In general, any technique or data structure that tracks the barcodes 732 associated with the sequence reads 728 that contain a respective k-mer 746 are within the scope of the present disclosure.

The value k is necessarily less than the average length of the sequence reads 728 in the plurality of sequence reads. In some embodiments, k have a value of 11, 13, 15, 17, 19, 21, 23, 25, 27, 29, 31, 33, 35, 37, 39, 41, 43, 45, 47, 49, 51, or 43. In some embodiments k is an even integer between 6 and 100. In some embodiments k is an odd integer between 5 and 99. In some embodiments, each respective set of k-mers includes at least eighty percent of the possible k-mers of length k of the corresponding sequence read 728 (1138). For example, referring to FIG. 10, if the sequence read has the sequence GATCCATCTT (SEQ ID NO: 1) and k is set to 3, the corresponding set of k-mers includes at least 80 percent of the 8 possible k-mers, e.g., at least 6 of the 8 possible k-mers.

In some embodiments, each respective set of k-mers includes at least sixty percent, at least seventy percent, at least eighty percent, at least ninety percent, at least ninety-five percent, or all of the possible k-mers of length k of the corresponding sequence read 728 (1138). In some embodiments, a respective set of k-mers includes at least sixty percent, at least seventy percent, at least eighty percent, at least ninety percent, at least ninety-five percent, or all of the possible k-mers of length k of the first portion of the corresponding sequence read 728 (1138). In some embodiments, two or more sets of k-mers includes at least sixty percent, at least seventy percent, at least eighty percent, at least ninety percent, at least ninety-five percent, or all of the possible k-mers of length k of the corresponding sequence read 728 (1138).

Referring to FIG. 11C (1140), in some embodiments, the plurality of sequence reads collectively provide at least 15× or at least 25× coverage for the larger contiguous nucleic acid 802, more than ten percent or more than thirty percent of k-mers 746 in the plurality of k-mers are from more than one sequence read 728 in the plurality sequence reads, and the identifier 732 of each such sequence read 728 for each k-mer 746 represented by more than one sequence read is retained.

In some embodiments, more than ten percent, more than twenty percent, more than thirty percent, more than forty percent, more than fifty percent, more than sixty percent, more than seventy percent, or more than eighty percent of the k-mers in the plurality of k-mers are from more than one sequence read 728 in the plurality sequence reads. In instances where a respective k-mer 746 is found in more than one sequence read 728, the barcode (second portion) 732 of each sequence read 728 is associated with the respective k-mer 746.

In some embodiments, the plurality of sequence reads collectively provide at least 5×, 10×, 15×, 20×, 25×, or at least 30× coverage for the larger contiguous nucleic acid 802.

Referring to FIG. 11C (1140), in some embodiments, the sequence reads 728 in the plurality of sequence reads encode between 75 and 125 bases of the larger contiguous nucleic acid 802 and the value k is an odd integer between 5 and 73 (1142). In some embodiments, the sequence reads 728 in the plurality of sequence reads encode between 80 and 120 bases of the larger contiguous nucleic acid 802 and the value k is an odd integer between 11 and 51. In some embodiments, the sequence reads 728 in the plurality of sequence reads encode between 90 and 110 bases of the larger contiguous nucleic acid 802 and the value k is an odd integer between 13 and 45.

Referring to FIG. 11C (1144), in some embodiments, the respective set of k-mers is created by hashing the first portion 730 each sequence read 728 in the plurality of sequence reads according to a predetermined k-mer length k thereby creating a respective set of k-mers for each sequence read 728 in the plurality of sequence reads. One such method of generating k-mers from a sequence read involves computing a hash function at each position of a sliding window of nucleotide length k overlayed on the first portion 730 of sequence read 728, in order to form a set of k-mers corresponding to the first portion 730 of the sequence read. In this method, each possible k-mer of length k is hashed using a simple function, called the hash function. One possible hash function h(W) for nucleic acid sequences maps a k-mer of the form $W=w_1w_1, \ldots w_k$ from the first portion 730 of the sequence read 728 according to:

$$h(W)=f(w_k)+f(w_{k-1})\times 4+ \ldots +f(w_1)\times 4^{k-1}$$

where f ($w_i$)=0, 1, 2, 3 for $w_i$=A, C, G, T. Other hash functions are possible. In general any function that assigns a k-mer of the sequence W=$w_1w_1 \ldots w_k$ from a sequence read to a unique number that can be used to reconstruct the actual nucleic acid sequence of the k-mer can be used. FIG. 9 shows the possible values of h(W) for the 64 possible k-mers of length three. Accordingly, in some embodiments, the value h(W) for each k-mer 746 is stored in hash table 740 or some other form of data structure. In some embodiments, as illustrated in FIG. 7, for each sequence read 728, the associated second portion 732 (e.g., bar code) of the partition from which the sequence read 728 is retained. Further, in some embodiments, the data structure for k-mers 740 further includes the position of each k-mer 746 in the corresponding sequence read 728. In typical embodiments, each possible k-mer in the first portion 730 of sequence read 728 is converted to a k-mer 746. For instance, in an example where the k-mer length is three and W=$w_1w_1 \ldots w_k$ (e.g., the second portion 732 of the sequence read 728) is GATC-CATCTT (SEQ ID NO: 1), the k-mers of FIG. 10 would be generated and hash values, e.g., h(W) values, for each of these k-mers would be generated.

Figure 11D:
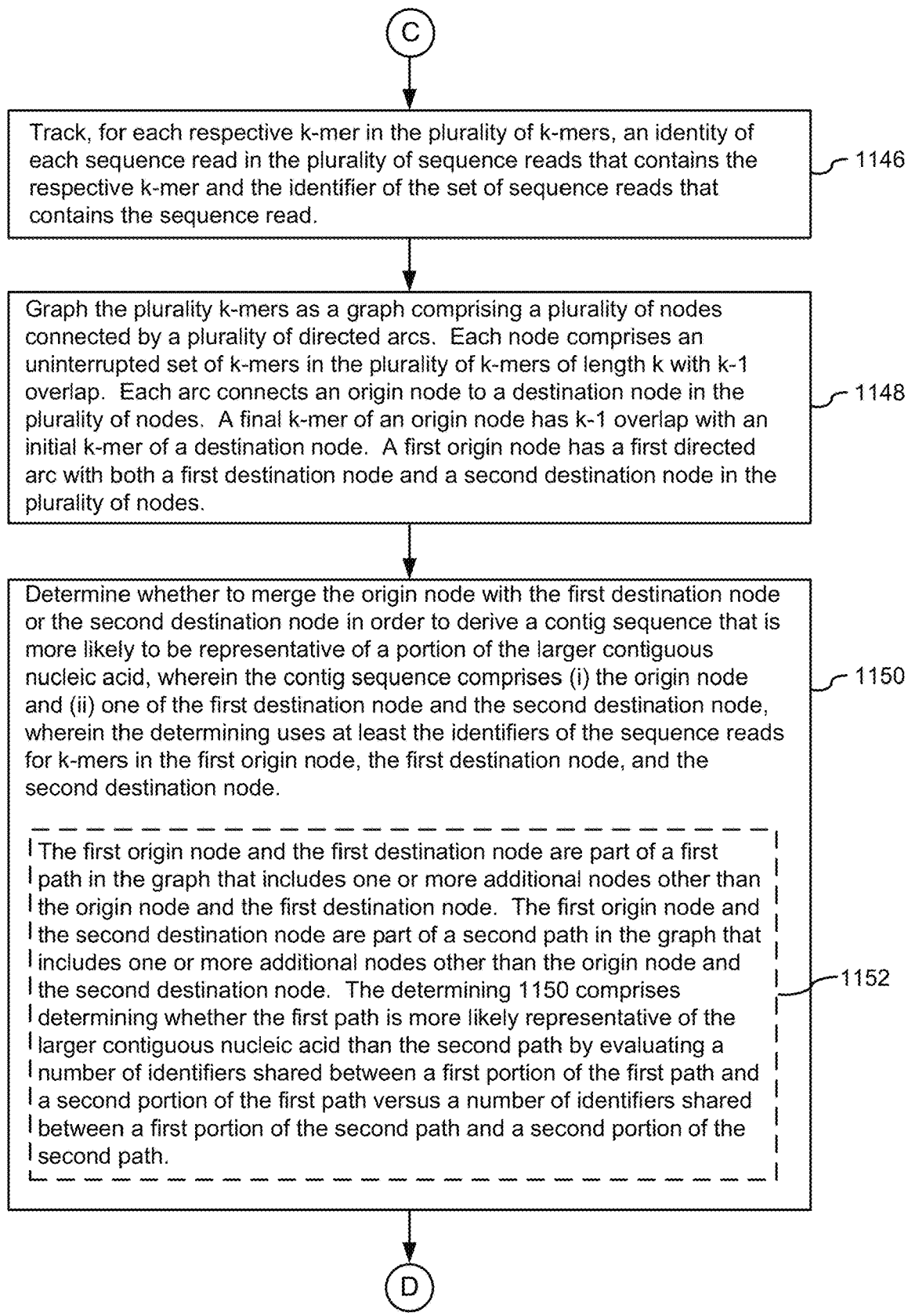

Track the k-mers. Referring to FIG. 11D (1146), for each respective k-mer 746 in the plurality of k-mers, an identity of each sequence read 728 in the plurality of sequence reads that contains the respective k-mer 746 and the identifier 732 of the set of sequence reads that contains the sequence read is tracked. For example, referring to FIG. 7, one way to accomplish this is to track all the k-mers 746 generated from a sequence read 728 along with the barcode 732. Alternative ways are possible. For instance, a data structure, or collection of data structures, that track all the sequence reads 728 that contain a respective k-mer 746, along with the barcodes 732 of these sequence reads 728, may be implemented. This data structure, or collection of data structures, would further track the sequence reads 728 that contain all other respective k-mer 746, along with the barcodes 732 of these sequence reads 728.

Graph the k-mers. Referring to FIG. 11D (1148), the plurality k-mers are graphed as a graph comprising a plurality of nodes connected by a plurality of directed arcs. Each node comprises an uninterrupted set of k-mers in the plurality of k-mers of length k with k–1 overlap. Each arc connects an origin node to a destination node in the plurality of nodes. A final k-mer of an origin node has k–1 overlap with an initial k-mer of a destination node. A first origin node has a first directed arc with both a first destination node and a second destination node in the plurality of nodes (1148).

Figure 14:
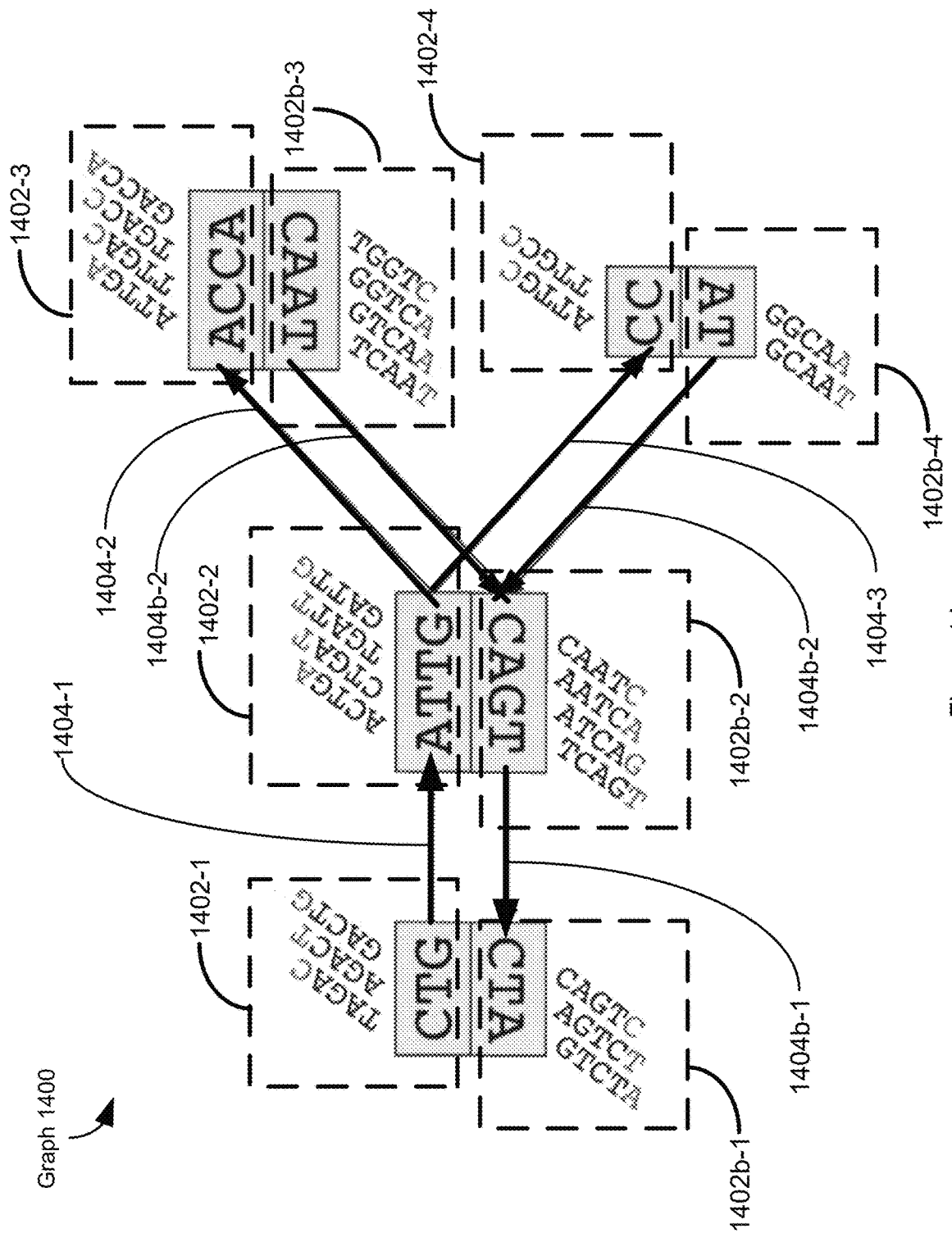
FIG. 14 illustrates a de Bruijn graph in accordance with some embodiments.

FIG. 14 illustrates one such graph 1400, which is known in the art as a de Bruijn graph. See Zerbino and Birney, "Velvet: Algorithms for de novo short read assembly using de Bruijn graphs," Genome Reach 2008, 18:821-829, which is hereby incorporated by reference in its entirety. Each node 1402 represents a series of overlapping k-mers. In the case of FIG. 14, k=5. Adjacent k-mers in a node 1402 overlap by k–1 nucleotides. The marginal information contained by a k-mer is its last (e.g., last 3') nucleotide. The sequence of those final nucleotides is called the sequence of the node 1402b, or s(N). In FIG. 14, and in optional embodiments, each node 1402 is attached to a twin node 1402b, which represents the reverse series of reverse complement k-mers. This ensures that overlaps between reads from opposite strands are taken into account. Note that the sequences attached to a node and its twin do not need to be reverse complements of each other. The union of a node 1402 and its twin 1402b is referred to a "block." Nodes 1402 are connected by a directed "arc" 1404. In that case, the last k-mer of an arc's origin node overlaps with the first of its destination node. Because of the symmetry of the blocks, if an arc goes from node 1402-1 to node 1402-2, a symmetric arc goes from node 1402b-2 to 1402b-1. On these nodes 1402 and arcs 1404, reads are mapped as "paths" traversing the graph. Extracting the nucleotide sequence from a path is taken from the initial k-mer of the first node and the sequences of all the nodes in the path.

FIG. 14 illustrates a situation in which a first origin node has a first directed arc with both a first destination node and a second destination node in the plurality of nodes (1148). In particular node 1402-2 is an origin node with a first directed arc 1404-2 to node 1402-3 and a second directed art 1404-3 to node 1402-4. This is because there is k–1 overlap between last k-mer of node 1402-2 (GATTG) and the first k-mer of node 1402-3 (ATTGA), i.e., an overlap of ATTG, as well as an overlap between last k-mer of node 1402-2 (GATTG) and the first k-mer of node 1402-4 (ATTGC), i.e., an overlap of ATTG. Thus, there are two paths in graph 1400, the path that comprises 1402-1→1404-1→1402-2→1404-2→1402-3 and the path that comprises 1402-1→1404-1→1402-2→1404-3→1402-4. The disclosed methods are useful in determining which path more likely represents the corresponding sequence of the larger nucleic acid 802.

Determine which nodes to merge. Referring to FIG. 11D (1150), a determination as to whether to merge the origin node with the first destination node or the second destination node is made in order to derive a contig sequence comprising (i) the origin node and (ii) one of the first destination node and the second destination node. The contig sequence that is more likely to be representative of the corresponding portion of the larger contiguous nucleic acid 802 is determined and selected. For example, referring to FIG. 14, a determination is made as to whether to merge node 1402-2 (origin node) and 1402-3 (first destination node) or to merge 1402-2 (origin node) and 1402-4 (second destination node). This determining 1150 advantageously uses at least the identifiers 732 of the sequence reads 728 for k-mers 740 in the first origin node, the first destination node, and the second destination node to identify the contig that is more likely to be representative of the corresponding portion of the larger contiguous nucleic acid 802.

In some embodiments, step 1150 is accomplished, at least in part, by evaluating the barcodes 732 associated with each k-mer in two or more paths. For instance, in graph 1400, the barcodes 732 of the k-mers in path 1402-1→1404-1→1402-2→1404-2→1402-3 and the barcodes 732 of the k-mers in path 1402-1→1404-1→1402-2→1404-3→1402-4 are evaluated. Since the source nucleic acid 802 typically includes multiple copies of the target nucleic acid (e.g., multiple copies of the same target chromosome or other nucleic acid that is to be sequenced), there are typically multiple barcodes 732 for each k-mer in a node. Nevertheless, the correct path, that is the path that represents a true sequence found in the larger contiguous nucleic acid 802, will have more barcodes in common than paths that do not represent the true sequence found in the larger contiguous nucleic acid 802. The actual method by which barcodes are used to identify the correct path is dependent upon a number of variables and so may vary.

In some embodiments, the more likely path, that is the better contig sequence comprising (i) the origin node and (ii) one of the first destination node and the second destination node, is selected by imposing a cut off, for instance, requiring at least 30 percent of the barcodes representing any of the k-mers in the origin node and any of the k-mers in the selected destination node be common between the two nodes.

In some embodiments, the more likely path, that is the better contig sequence comprising (i) the origin node and (ii) one of the first destination node and the second destination node, is selected by imposing a cut off, for instance, requiring at least 10 percent of the barcodes representing, at least 20 percent of the barcodes representing, at least 30 percent of the barcodes representing, at least 40 percent of the barcodes representing, at least 50 percent of the barcodes representing or at least 60 percent of the barcodes representing any of the k-mers in the origin node and any of the k-mers in the selected destination node be common between the two nodes.

In some embodiments, the more likely path, that is the better contig sequence comprising (i) the origin node and (ii) one of the first destination node and the second destination node, is selected by identifying the node pair that has the highest percentage of shared barcodes.

Referring to FIG. 11D (1152), in some embodiments, the first origin node and the first destination node are part of a first path in the graph that includes one or more additional nodes other than the origin node and the first destination node. The first origin node and the second destination node are part of a second path in the graph that includes one or more additional nodes other than the origin node and the second destination node. This is illustrated in FIG. 14 as path 1402-1→1404-1→1402-2→1404-2→1402-3 and path 1402-1→1404-1→1402-2→1404-3→1402-4 where node 1402 is an additional node in both instances. In some such embodiments, the determining of 1150 comprises determining whether the first path is more likely representative of the larger contiguous nucleic acid than the second path by evaluating a number of identifiers 728 shared between the k-mers of the nodes of a first portion of the first path and the k-mers of the nodes of a second portion of the first path versus a number of identifiers shared between the k-mers of the nodes of a first portion of the second path and the k-mers of the nodes of a second portion of the second path (1152). In some embodiments, this is done on a relative basis. For instance, of the total number of identifiers 746 associated with any of the k-mers in a path, what percentage of them are shared between a first portion of the path and a second portion of the path. For example, referring to FIG. 15, consider an instance where path 1 comprises nodes 1502, 1504, 1506, 1508, 1510, and path 2 comprises nodes 1512, 1514, 1506, 1516, and 1518. Path 1 can be divided into a first portion consisting of nodes 1502, 1504, and 1506 and a second portion consisting of nodes 1508 and 1510. The identifiers 732 associated with any of the k-mers of nodes 1502, 1504, and 1506 are determined. The identifiers 732 associated with any of the k-mers of nodes 1508 and 1510 are determined. This is repeated for the second path. That is, path 2 is divided into a first portion consisting of nodes 1512, 1514, and 1506 and a second portion consisting of nodes 1516 and 1518. The identifiers 732 associated with any of the k-mers of nodes 1512, 1514, and 1506 are determined. The identifiers 732 associated with any of the k-mers of nodes 1516 and 1518 are determined. The extent to which there is overlap between the identifiers 732 of the first and second portions of the first path is compared to the extent to which there is overlap between the identifiers 732 of the first and second portions of the second path. For instance, consider the case in which thirty percent of the total number of identifiers found in either the first or second portion of the first path is found in both the first and second portion of the first path. Further, forty-five percent of the total number of identifiers found in either the first or second portion of the second path is found in both the first and second portion of the second path. In this instance, the second path will be deemed to be more likely representative of a corresponding part of the larger contiguous nucleic acid 802. Other techniques for comparing the barcodes 732 of k-mers in paths may be used, such as Bayesian analysis or Pearson's chi-squired test. The instance discovery is the use of the barcodes 732 to break ambiguity in the paths.

Figure 11E:
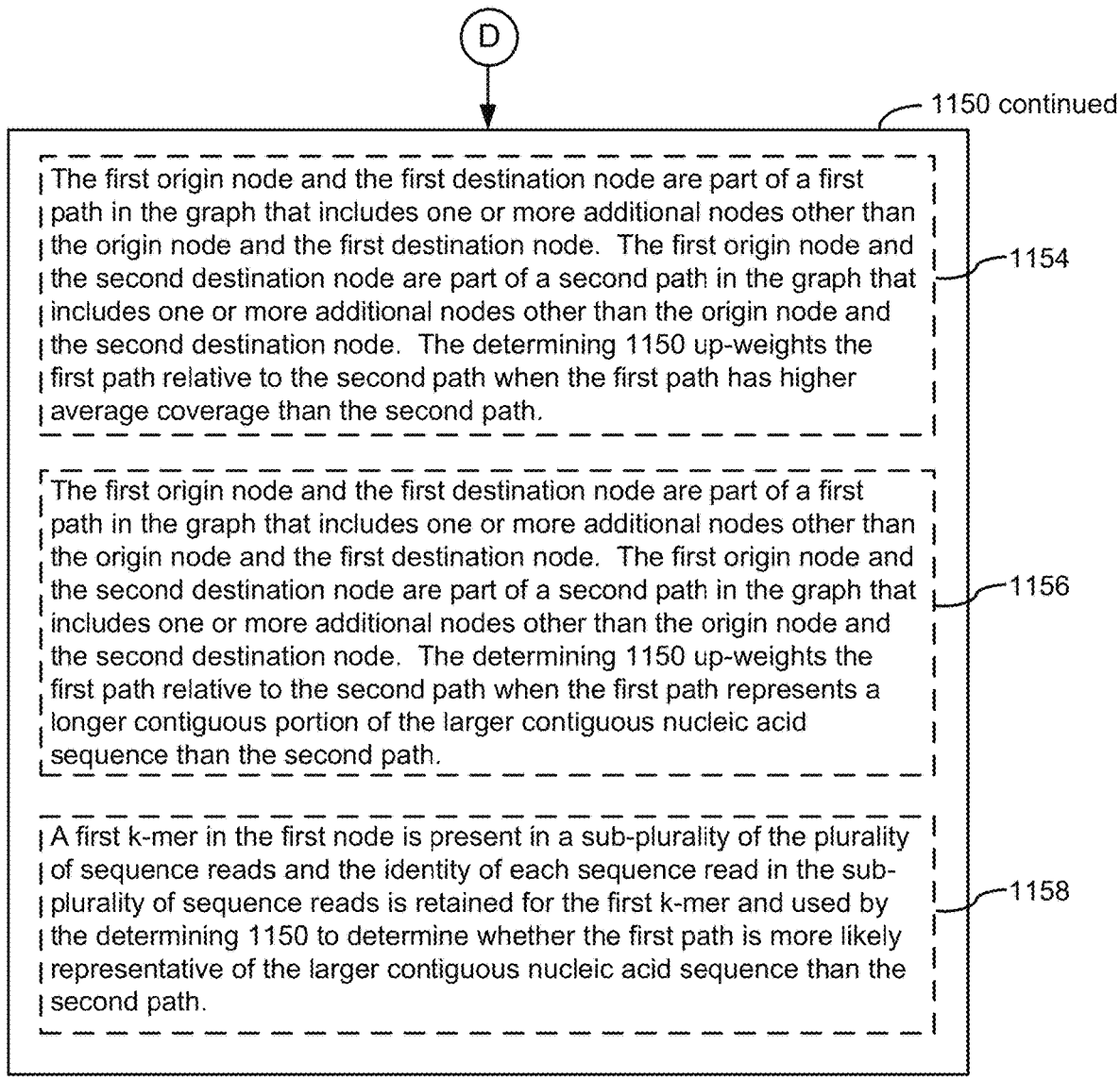

Referring to FIG. 11E (1154), in some embodiments, the first origin node and the first destination node are part of a first path in the graph that includes one or more additional nodes other than the origin node and the first destination node. The first origin node and the second destination node are part of a second path in the graph that includes one or more additional nodes other than the origin node and the second destination node. The determining up-weights the first path relative to the second path when the first path has higher average coverage than the second path (1154). Referring again to FIG. 15 to illustrate and again considering path 1 (1502, 1504, 1506, 1508, 1510), and path 2 (nodes 1512, 1514, 1506, 1516, and 1518), if there is higher coverage by the k-mers of the nodes of path 1 relative to the k-mers of the nodes of path 2, this may be used as a tie breaker in instances where process 1150 or 1152 of FIG. 11 was not able to identify a clear winner based on the sequence identifiers alone.

Referring to FIG. 11E (1156), in some embodiments, the first origin node and the first destination node are part of a first path in the graph that includes one or more additional nodes other than the origin node and the first destination node. The first origin node and the second destination node are part of a second path in the graph that includes one or more additional nodes other than the origin node and the second destination node. The determining up-weights the first path relative to the second path when the first path represents a longer contiguous portion of the larger contiguous nucleic acid sequence than the second path (1156). In some embodiments, process 1156 is used as a tie breaker in instances where process 1150, 1152, or 1154 of FIG. 11 is not able to identify a clear winner based on the sequence identifiers alone. In some embodiments, process 1156 is used in conjunction with processes 1150, 1152, and/or 1154 of FIG. 11 to identify a winner using multiple sources of information.

Referring to FIG. 11E (1158), in some embodiments, a first k-mer 746 in the first node is present in a sub-plurality of the plurality of sequence reads 728 and the identity of each sequence read 728 in the sub-plurality of sequence reads is retained for the first k-mer 728 and used by the determining 1150 to determine whether the first path is more likely representative of the larger contiguous nucleic acid sequence than the second path (1158). This arises in many instances where the sample of the larger contiguous nucleic acid 802 that is partitioned into fragments 804 in fact constitutes multiple copies of a target nucleic acid (e.g., multiple copies of the same target chromosome or other nucleic acid that is to be sequenced). This results in multiple barcodes 732 for each k-mer 746 in a node. As such, any of the processes 1150, 1152, 1154, 1156 and/or 1158 are capable of taking this into account.

Another aspect of the present disclosure provides a sequencing method comprising, at a computer system having one or more processors, and memory storing one or more programs for execution by the one or more processors, obtaining a plurality of sequence reads as disclosed above in relation to 1106 of FIG. 11A. The plurality of sequence reads comprises a plurality of sets of sequence reads. Each respective sequence read in a set of sequence reads includes (i) a unique first portion that corresponds to a subset of a larger contiguous nucleic acid and (ii) a common second portion that forms an identifier that is independent of the sequence of the larger contiguous nucleic acid and that identifies a partition, in a plurality of partitions, in which the respective sequence read was formed. Each respective set of sequence reads in the plurality of sets of sequence reads is formed in a partition in the plurality of partitions. Each such partition includes one or more fragments of the larger contiguous nucleic acid that is used as the template for each respective sequence read in the partition.

In the method, a respective set of k-mers is created for each sequence read in the plurality of sequence reads as discussed above in relation to element 1138 of FIG. 11C. The sets of k-mers collectively comprise a plurality of k-mers. The identifiers 732 of the sequence read 728 for each k-mer 746 in the plurality of k-mers is retained. The value k is less than the average length of the sequence reads in the plurality of sequence reads. Each respective set of k-mers includes at least some of (e.g., at least eighty percent of) the possible k-mers of the first portion of the corresponding sequence read.

Figure 15:
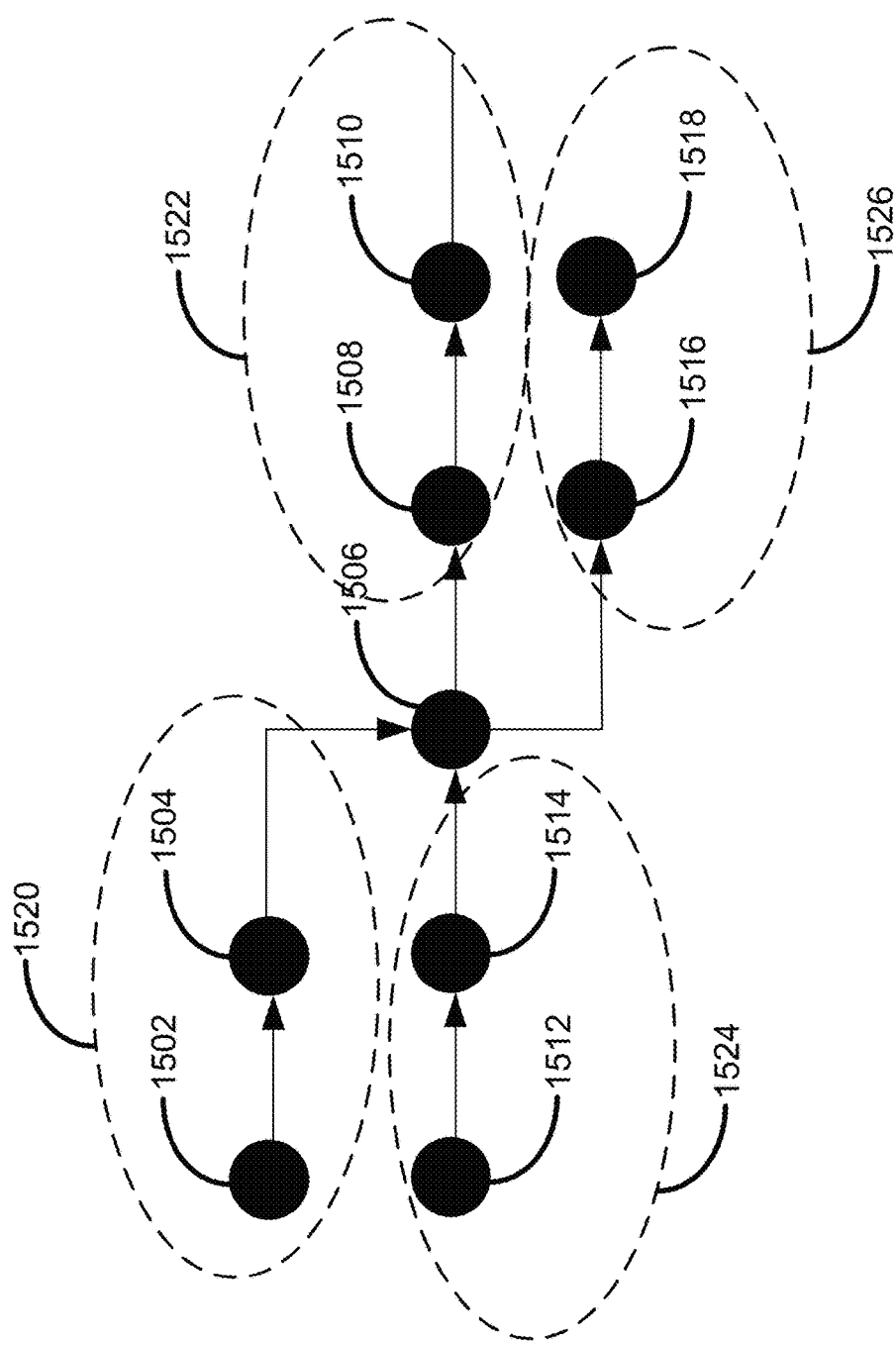
FIG. 15 illustrates another de Bruijn graph in accordance with some embodiments.

In the method, there is tracked, for each respective k-mer in the plurality of k-mers, an identity of each of the sequence reads in the plurality of sequence reads that contains the respective k-mer. A first path is identified. The first path comprises a first set of k-mers with k−1 overlap in the plurality of k-mers (e.g., nodes 1502, 1504, 1506, 1508, and 1510 of FIG. 15). A second path is identified. The second path comprises a second set of k-mers with k−1 overlap in the plurality of k-mers (e.g., nodes 1512, 1514, 1506, 1516, and 1518 of FIG. 15). The first path intersects the second path (e.g., as illustrated in FIG. 15), thereby forming the set of branch segments comprising: a left portion of the first path (nodes 1502 and 1504), a right portion of the first path (nodes 1508 and 1510), a left portion of the second path (nodes 1512 and 154) and a right portion of the second path (1516 and 1518) where the choice of what do with the bisecting node 1506 (e.g, not use it, put it in paths, or put it in one portion of each path) is application dependent. The identifiers associated with the k-mers of the set of branch segments are used to verify the connectivity of the branch segments. In some embodiments, this comprises evaluating a number of identifiers shared between each possible branch segment pairs in the set of branch segments. In some instances, this may result in rerouting a path. For example, in evaluating the graph of FIG. 15, four possible paths are possible, as set forth in the following Table. As the table indicates, path 1520 to 1522 (nodes 1502, 1504, 1506, 1508, and 1510) and path 1524 to 1526 (1512, 1514, 1506, 1516, and 1518 are verified as correct because they each have more overlapping barcodes, on a relative basis, than path 1520 to 1526 and 1524 to 1522.

| Left Path branch segment | Left Path branch segment | Number of Sequence Identifiers 732 in Left Branch Segment | Number of Sequence Identifiers 732 in Right Branch Segment | Number of Sequence Identifiers 732 that overlap left and right branch |
|---|---|---|---|---|
| 1520 | 1522 | 100 | 110 | 65 |
| 1520 | 1526 | 100 | 105 | 3 |
| 1524 | 1522 | 90 | 110 | 8 |
| 1524 | 1526 | 90 | 105 | 50 |

In some embodiments, additional information such as path lengths and path coverage is used to verify these connections. It will be appreciated that any form of statistical analysis may be applied to the information such as that in the above table to verify the paths.

III. Exemplary Assembly Process

The following is an example of an overall de novo assembly process as described above, is set forth below, and schematically illustrated in the process flow chart shown in FIG. 4. As shown, following sequencing and read generation, the short read sequences are aggregated in a data structure and subjected to pre-assembly processing at step 402. In these reads, sequence data associated with functional components of the sequenced fragments, e.g., adapter sequences, read primer sequences, etc., are removed from the sequence reads. Duplicate reads may be eliminated by identifying those that are duplicated both in the first two k-mers of the sense read and the partner or antisense read. Where the initial k-mers are common among duplicate reads and their complements, all but one can be removed as a duplicate using, e.g., A FastUniq algorithm, or other similar algorithms. In some cases, duplicate reads may get through the pre-assembly process, where one or more of those duplicates include a sequencing error. Because these first few k-mers occur at the beginning of a sequencing run where errors are fewer, it would be expected that the probability of this occurring would be low. In addition to duplicate reads, low complexity reads, e.g., reads where a single base makes up 90% or more of the read, or reads that are entirely or substantially made up of 2, 3, or 4 base repeat units.

The reads are then subjected to an error correction algorithm at step 404, as uncorrected errors in sequence reads result in fragmented assemblies and add computational complexity. Different error correction algorithms are generally available (see, e.g., Tahir et al., "Review of Genome Sequence Short Read Error Correction Algorithms", Am. J. Bioinformatics Res. 2013; 3(1) 1-9, which is hereby incorporated herein by reference) and include, for example the QUAKE, and standalone ALLPATHS-LG error correction algorithm.

Following the preassembly processing and error correction, using a k-mer size of, e.g., k=20 or k=24, a frequency spectrum of k-mers is generated across all of the aggregated reads at step 406. Assuming a typical genome profile, sequenced without significant bias, the expectation would be for a Gaussian distribution of k-mer frequency, where the center of the peak indicates the mean k-mer coverage of the genome. The size of the k-mer used for calculation of the frequency spectrum may generally vary depending upon the complexity of the genome being analyzed, the expected level of sequencing coverage, and the like.

An initial assembly graph is then assembled at step 408 from the error corrected reads, using the k-mer assembly process described with reference to FIG. 1B. In some cases, longer k-mer sequences may be used, e.g., for sequence reads of 150 bases, k-mers of 40 or more, 50 or more, or 60 or more bases may be used. From the graph, unbranched paths are collapsed into individual primary paths.

Hanging ends that represent relatively short branches, e.g., of 1, 2 or 3 k-mers, are generally prevalent in the sequence and can result from a number of origins, including from uncorrected reads. These short paths are easily recognized and may be removed from the assembly graph, either before or after identifying the primary paths. In some cases, short branches may appear, but may be derived from missing sequence in the error corrected reads, which can result from low coverage.

The barcode sequences coupled with the error corrected reads are then associated with their respective primary paths, at step 410 generating a list of the barcodes associated with each primary path. For each primary path, a copy number of that primary path within the genome is estimated. As noted, the copy number of a given primary path will generally depend upon the complexity of the genome and the length and complexity of the primary path. Copy number can generally be estimated from the number of reads that touch a primary path, and comparing it to the mean k-mer coverage derived from the k-mer spectrum calculated at step 406. Short primary paths may generally be ignored, as determining their copy number is more difficult since a much larger proportion of reads that touch on those primary paths may only partially overlap them. From this, low copy number primary paths, e.g., with a copy number approaching 1, also referred to as CN1 paths, as noted above, may be identified at step 412.

Figure 5:
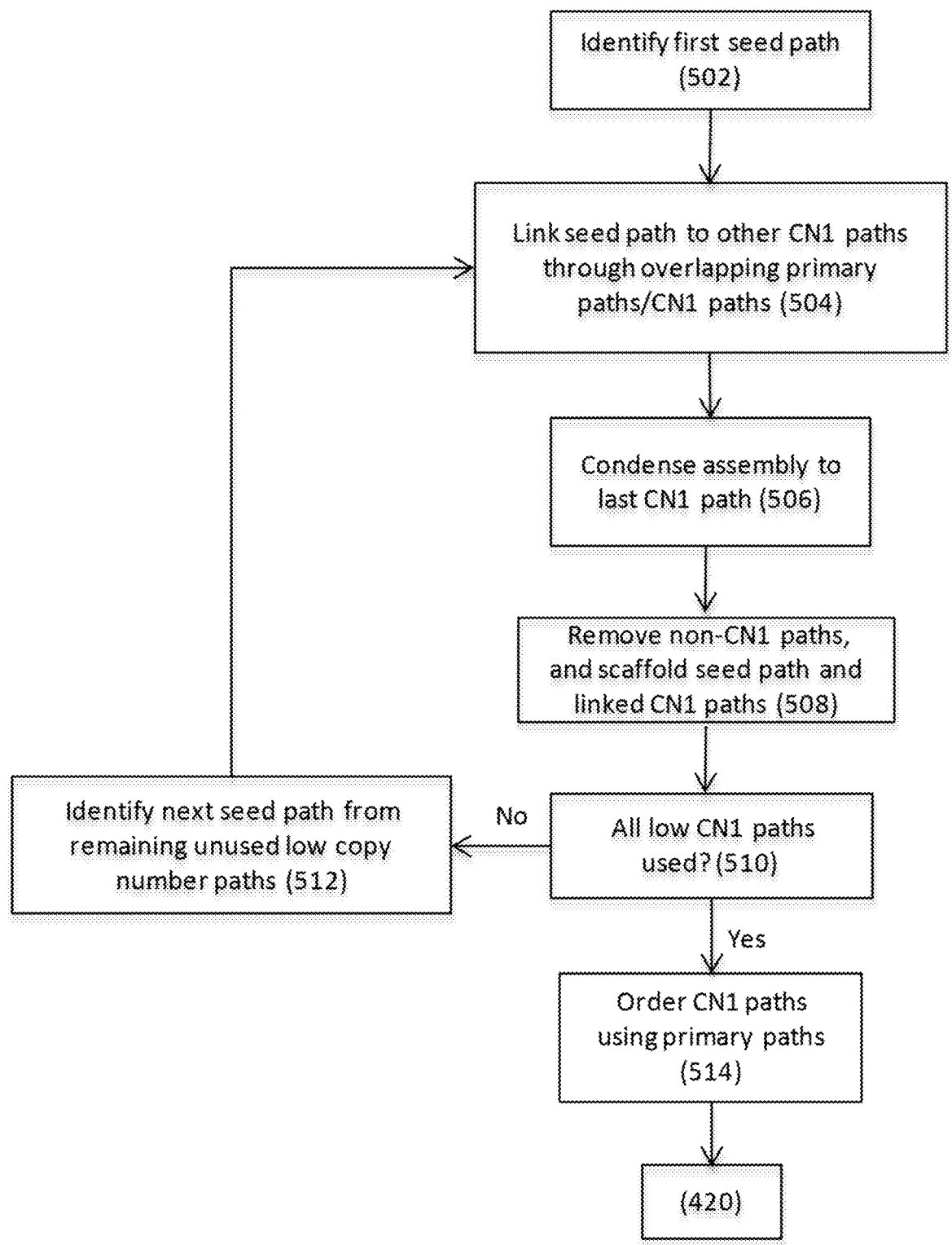
FIG. 5 schematically illustrates aspects of the assembly processes in accordance with some embodiments.
Figure 6A:
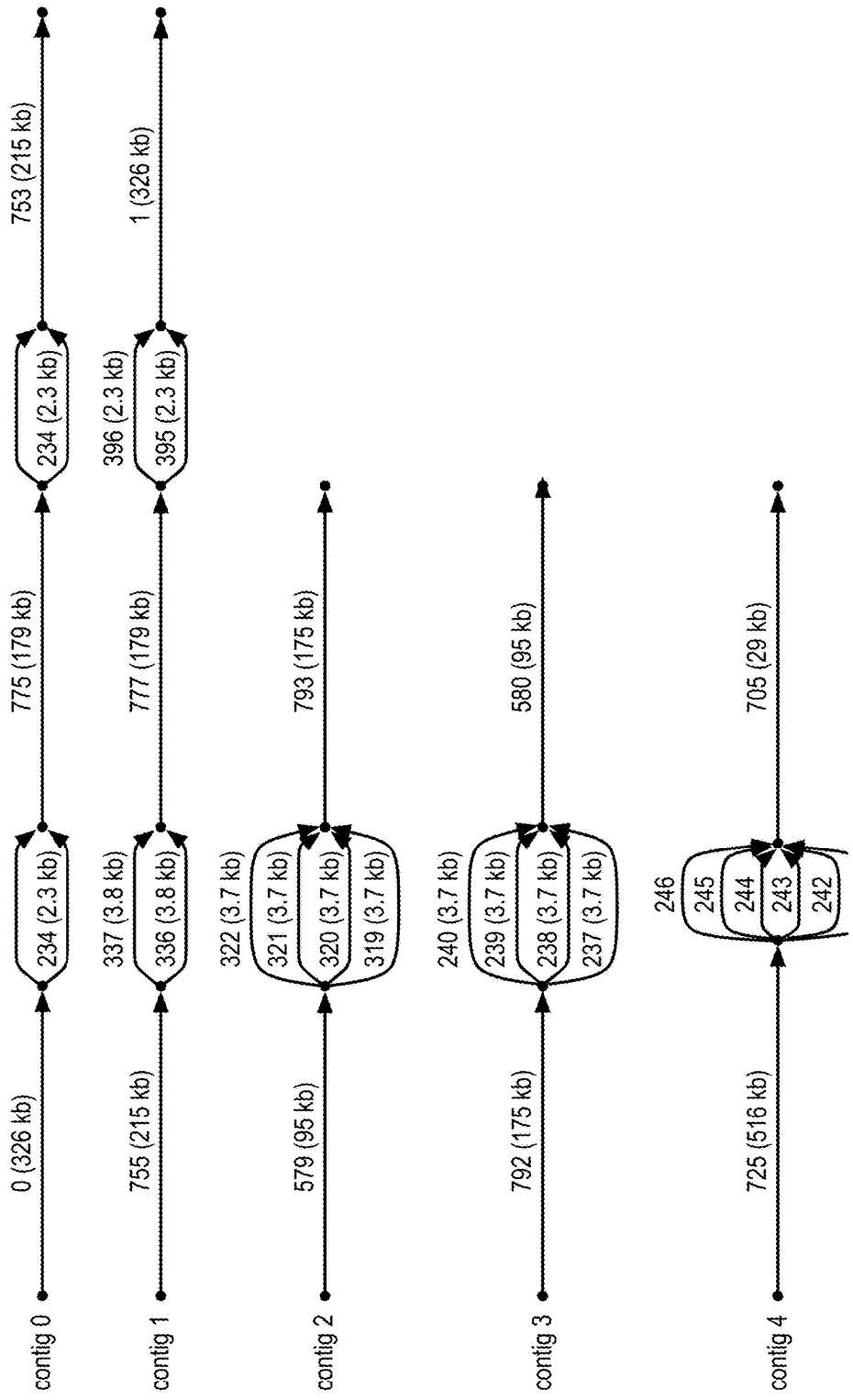
FIGS. 6A, 6B, 6C, and 6D show de novo assembly of E. coli sequence data using the barcoded sequencing methods described herein.
Figure 6B:
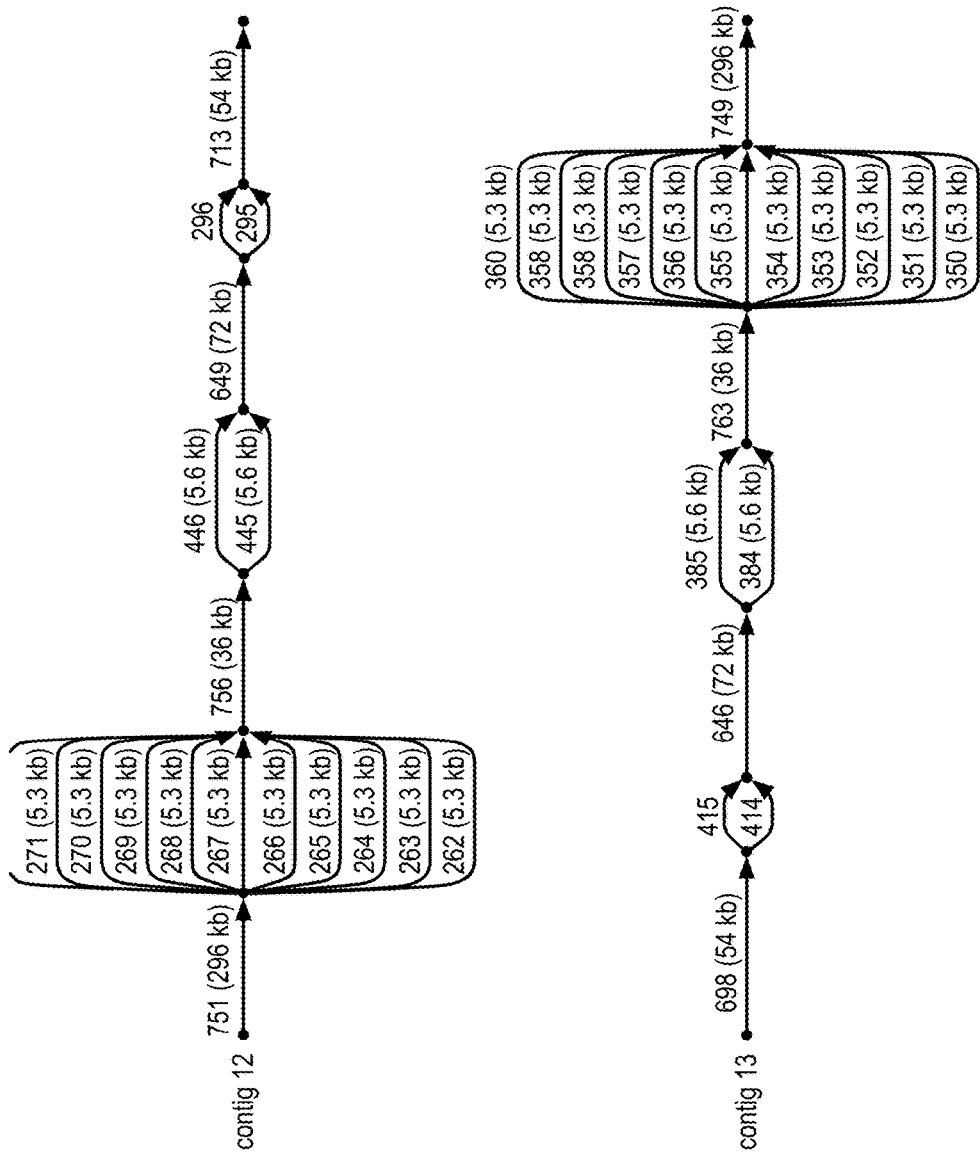
Figure 6C:
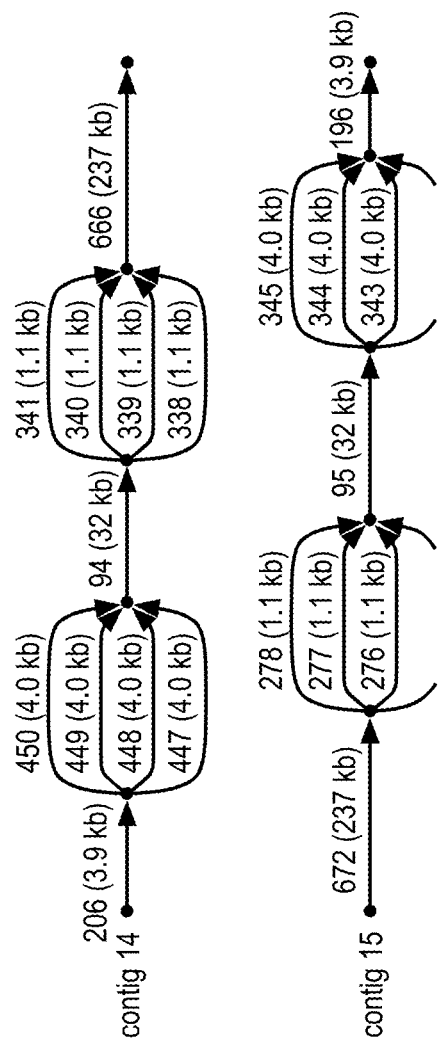
Figure 6D:
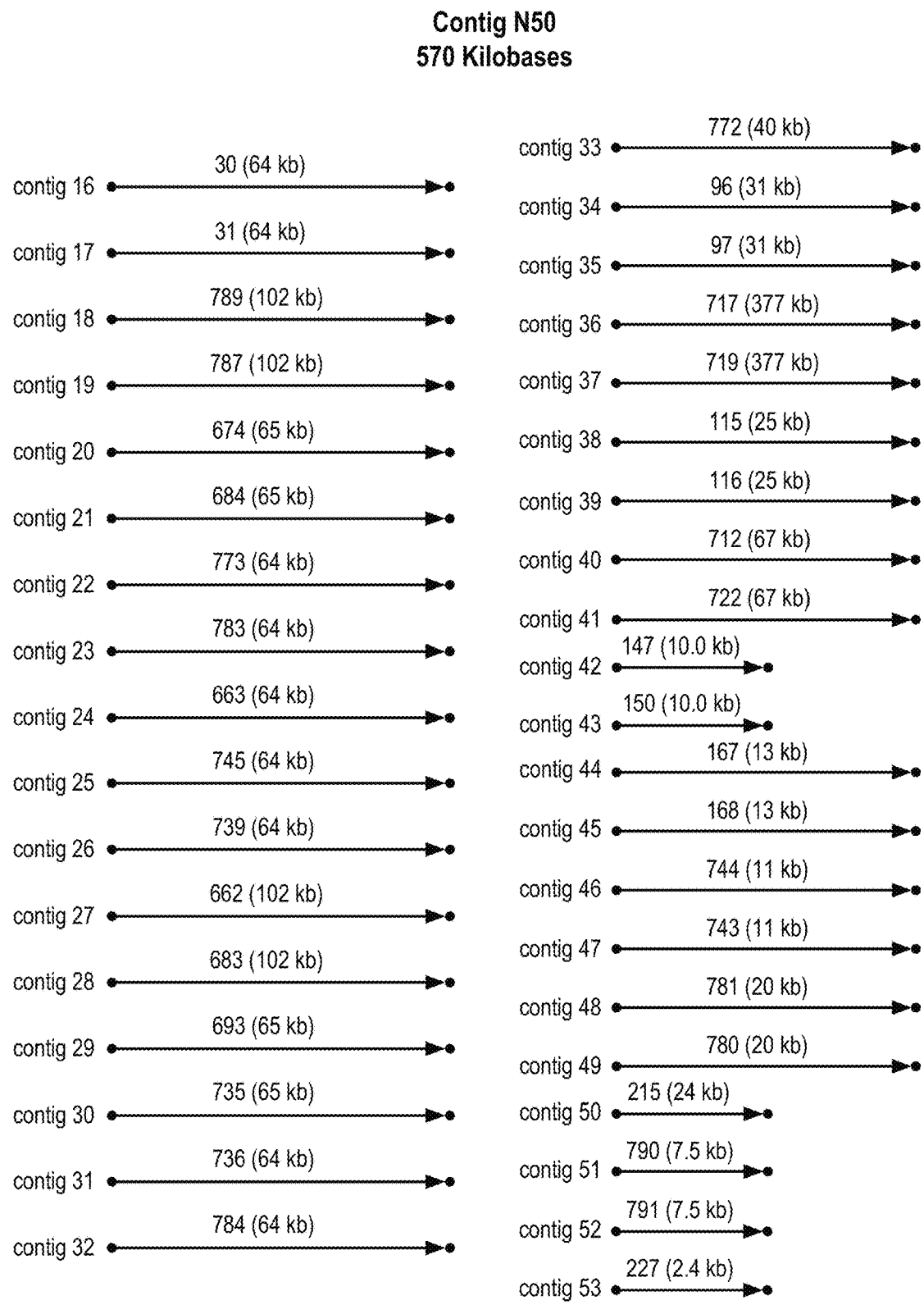

The CN1 primary paths are then assembled in a scaffold with the aid of the associated barcode sequences. In particular, the CN1 primary path that is associated with the largest number of barcodes is selected as a seed path at step 414. At step 416, the seed path is then extended to all other overlapping primary paths containing the common barcode sequence, considering each primary path only once, and ignoring primary paths that have a barcode frequency below a desired level, e.g., less than half the barcode frequency in the seed path. FIG. 5 illustrates the process in greater detail. In particular, the first seed path is identified at step 502. That first seed path is ten extended as described for step 416, above. In particular, the extension is continued through primary paths and additional CN1 paths at step 504, until the end of a given branch is reached. The path is then trimmed back to the last CN1 path through which the path traveled at step 506, such that the assembled sequence will always begin an end on a CN1 path, and be anchored around the seed path.

The paths through the CN1 paths are then condensed by removing all of the non-CN1 paths, then merging together to form a single scaffold that defines the order to the CN1 paths around the first seed path at step 508. These CN1 paths are then designated as used.

The process is then repeated at step 512 using the CN1 path, from the remaining CN1 paths, that represents the highest remaining barcode frequency as the next seed path, and scaffolding against the remaining sets of CN1 paths. This is continued until all CN1 paths are designated as used. The set of condensed primary paths is then further merged to provide a final path or scaffold that gives the relative order of all of the CN1 paths in the genome at step 514. This forms the anchor scaffold which provides the basis for final assembly.

Once the CN1 path scaffold is assembled, local assembly is carried out to fill in the scaffold gaps between CN1 paths at step 420. For each gap in the scaffold, the adjacent primary paths are selected and the barcodes associated with them are identified. The group of reads that includes these barcodes are then used in conjunction with the adjacent CN1 paths to assemble a local primary path assembly graph in the same manner as used to assemble the global primary path graph. From each CN1 path, all paths that connect to the other primary path are identified. In many cases, only a single path will be identified allowing the use of that path as the patch to the gap. Where more than one path is identified between two adjacent CN1 primary paths, the path with the strongest read support is used to patch together the adjacent CN1 primary paths and close the gap. In cases where read support does not allow selection as between two paths, both paths may be included in the graph, or one can allow the gap to remain open.

From the full assembly, a linear graph of the entire genome is created that, ideally, includes no remaining gaps or doubled paths. However, in many cases, the linear graph may include some locations of dual paths or remaining gaps, but the overall order of the sequence is known. For remaining gaps or double paths, one may further examine uncorrected sequence data, or discarded sequence data to determine if any gaps or doubles may be informed by those sequences that were removed from the process early on. Alternatively, other disambiguation techniques may be used, such as using copy number information to inform ambiguous assemblies, or using read pair information to evaluate relative likelihood of multiple solutions for ambiguous assemblies.

In certain aspects, the methods provided herein are computer-implemented methods, wherein at least one or more steps of the method are carried out by a computer program. In some embodiments, the methods provided herein are implemented in a computer program stored on computer-readable media, such as the hard drive of a standard computer. For example, a computer program for determining at least one consensus sequence from replicate sequence reads can include one or more of the following: code for providing or receiving the sequence reads, code for identifying regions of sequence overlap between the sequence reads, code for aligning the sequence reads to generate a layout, contig, or scaffold, code for consensus sequence determination, code for converting or displaying the assembly on a computer monitor, code for applying various algorithms described herein, and a computer-readable storage medium comprising the codes.

In some embodiments, a system (e.g., a data processing system) that determines at least one assembly from a set of replicate sequences includes a processor, a computer-readable medium operatively coupled to the processor for storing memory, wherein the memory has instructions for execution by the processor, the instructions including one or more of the following: instructions for receiving input of sequence reads, instructions for overlap detection between the sequence reads, instructions that align the sequence reads to generate a layout, contig, or scaffold, instructions that apply a consensus sequence algorithm to generate at least one consensus sequence (e.g., a "best" consensus sequence, and optionally one or more additional consensus sequences), instructions that compute/store information related to various steps of the method, and instructions that record the results of the method.

In certain embodiments, various steps of the processes described herein utilize information and/or programs and generate results that are stored on computer-readable media (e.g., hard drive, auxiliary memory, external memory, server, database, portable memory device and the like. For example, information used for and results generated by the methods that can be stored on non-transitory computer-readable media include but are not limited to input sequence read information, set of pair-wise overlaps, newly generated consensus sequences, quality information, technology information, and homologous or reference sequence information.

In some aspects, the invention includes an article of manufacture for determining at least one sequence assembly that includes a machine-readable medium containing one or more programs which when executed implement the steps of the invention as described herein.

As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component, or to which the user uploads data to be processed using the above described hardware and/or software, at the remote location or locations, in accordance with the processes set forth herein.

The co/i genome (strain K12_DH10B) was used to model the de-novo assembly processes described herein. Sixty physical copies of the genome were sheared to an average size of 50 kilobases (standard deviation 5 kilobases) and partitioned at random into 5000 partitions, each containing a unique barcode. The process of the creation of a barcode-sequencing library was simulated within each partition. This was followed by simulation of sequencing of this library utilizing 150 bp paired-end reads to a mean depth of 30×. The simulation of the sequencing process incorporated an empirical error rate model derived from real sequencing data. FIG. 6 shows a de novo assembly plot for the above-described modeled data. As shown, the assembly resulted in N50 contigs of 750 kb as compared to N50 contigs of 60 kb for data based upon short read sequence alone, e.g., without barcodes.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. For example, particle delivery can be practiced with array well sizing methods as described. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

SEQUENCE LISTING

```
<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: reference sequence

<400> SEQUENCE: 1
gatccatctt                                                           10
```

Information appliances (or digital devices) that are generally used in conjunction with the processes describe herein include conventional logic systems, such as conventional computer systems, including both individual or personal computers, networked computers, computer mainframes, and the like. Interaction with these processes may not be limited to such conventional computing systems, but may additionally or alternatively include any information appliance for interacting with a remote data application, and could include such devices as a digitally enabled television, cell phone/smart phone, personal digital assistant, tablet, wearable electronic devices, e.g., Google Glass, smart watch, etc. Programming for carrying out the processes described herein on any of the foregoing types of devices may reside within the memory of the device itself (either main memory or auxiliary memory), or it may be accessed from other locations and devices, e.g., computers through, e.g., an API on the device, and an appropriate communications network, e.g., LAN, WAN, Wi-Fi, cellular, Bluetooth or other communications system.

What is claimed is:

1. A method of determining a sequence of a nucleic acid comprising, at a computer system having one or more processors, and memory storing one or more programs for execution by the one or more processors:

(A) obtaining, in electronic form, a plurality of sequence reads of the nucleic acid, wherein
the plurality of sequence reads comprises a plurality of sets of sequence reads,
the nucleic acid is greater than 100,000 base pairs in length,
each sequence read in the plurality of sequence reads has a length of less than 1000 bases,
the plurality of sets of sequence reads comprises more than 100,000 sets of sequence reads,
each respective sequence read in each respective set of sequence reads includes (i) a first portion that corresponds to a subset of the nucleic acid and (ii) a common second portion that forms an identifier that is independent of the sequence of the nucleic acid and that identifies a reaction partition, in a plurality of reaction partitions, in which the respective sequence read was formed, and each respective set of sequence reads in the plurality of sets of sequence reads is formed in a corresponding reaction partition in the plurality of reaction partitions and each reaction partition includes one or more fragments of the nucleic acid that is used as a template for respective sequence reads in the reaction partition;

(B) creating a respective set of k-mers for each sequence read in the plurality of sequence reads, wherein the sets of k-mers collectively comprise a plurality of k-mers and the identifiers of the source sequence reads for each k-mer in the plurality of k-mers are retained, (C) tracking, for each respective k-mer in the plurality of k-mers, an identity of each sequence read in the plurality of sequence reads that contains the respective k-mer and the identifier of the set of sequence reads that contains the sequence read;

(D) determining, using the plurality of k-mers, whether to derive a contig sequence that is more likely to be representative of a portion of the nucleic acid, wherein the contig sequence comprises (i) an origin node comprising a first uninterrupted set of overlapping k-mers within the plurality of k-mers and (ii) one of a first destination node comprising a second uninterrupted set of overlapping k-mers within the plurality of k-mers and a second destination node comprising a third uninterrupted set of overlapping k-mers within the plurality of k-mers, wherein the determining uses at least the identifiers of the sequence reads for k-mers in the first, second, and third uninterrupted set of overlapping k-mers; and (E) assembling the sequence of the nucleic acid from the plurality of k-mers using at least the contig sequence.

2. The sequencing method of claim 1, wherein,
the first origin node and the first destination node are part of a first path in a graph that includes one or more additional nodes other than the origin node and the first destination node,
the first origin node and the second destination node are part of a second path in the graph that includes one or more additional nodes other than the origin node and the second destination node, and
the determining (D) comprises determining whether the first path is more likely representative of the sequence of the nucleic acid than the second path by evaluating a number of identifiers shared between the k-mers of the nodes of a first portion of the first path and the k-mers of the nodes of a second portion of the first path versus a number of identifiers shared between the k-mers of the nodes of a first portion of the second path and the k-mers of the nodes of a second portion of the second path.

3. The sequencing method of claim 1, wherein
the first origin node and the first destination node are part of a first path in a graph that includes one or more additional nodes other than the origin node and the first destination node,
the first origin node and the second destination node are part of a second path in the graph that includes one or more additional nodes other than the origin node and the second destination node, and
the determining (D) up-weights the first path relative to the second path when the first path has higher average coverage than the second path.

4. The sequencing method of claim 1, wherein
the first origin node and the first destination node are part of a first path in a graph that includes one or more additional nodes other than the origin node and the first destination node,
the first origin node and the second destination node are part of a second path in the graph that includes one or more additional nodes other than the origin node and the second destination node, and
the determining (D) up-weights the first path relative to the second path when the first path represents a longer contiguous portion of the larger contiguous nucleic acid sequence than the second path.

5. The sequencing method of claim 1, wherein a first k-mer in the first node is present in a portion of the plurality of sequence reads and the identity of each sequence read in the portion of sequence reads is retained for the first k-mer and used by the determining (D) to determine whether the first path is more likely representative of the nucleic acid sequence than the second path.

6. The sequencing method of claim 1, wherein
a reaction partition in the plurality of reaction partitions comprises at least 1000 molecules with the common second portion, and
each molecule in the at least 1000 molecules further comprises a primer sequence complementary to at least a portion of the nucleic acid.

7. The sequencing method of claim 1, wherein
a reaction partition in the plurality of reaction partitions comprises at least 1000 molecules with the common second portion, and
each molecule in the at least 1000 molecules further comprises a primer site and a semi-random N-mer priming sequence that is complementary to part of the nucleic acid.

8. The sequencing method of claim 1, wherein the one or more fragments of the nucleic acid in a reaction partition in the plurality of reaction partitions are greater than 50 kilobases in length.

9. The sequencing method of claim 1, wherein the one or more fragments of the nucleic acid in a reaction partition in the plurality of reaction partitions are between 20 kilobases and 200 kilobases in length.

10. The sequencing method of claim 1, wherein the one or more fragments of the nucleic acid in a reaction partition in the plurality of reaction partitions consists of between 1 and 500 different fragments of the nucleic acid.

11. The sequencing method of claim 1, wherein the plurality of sequence reads is obtained from less than 5 nanograms of nucleic or ribonucleic acid.

12. The sequencing method of claim 1, wherein the identifier in the second portion of each respective sequence read in a respective set of sequence reads encodes a common value selected from the set $\{1, \ldots, 1024\}$, the set $\{1, \ldots, 4096\}$, the set $\{1, \ldots, 16384\}$, the set $\{1, \ldots, 65536\}$, the set $\{1, \ldots, 262144\}$, the set $\{1, \ldots, 1048576\}$, the set $\{1, \ldots, 4194304\}$, the set $\{1, \ldots, 16777216\}$, the set $\{1, \ldots, 67108864\}$, or the set $\{1, \ldots, 1 \times 10^{12}\}$.

13. The sequencing method of claim 1, wherein the identifier is an N-mer, and N is an integer selected from the set $\{4, \ldots, 20\}$.

14. The sequencing method of claim 1, wherein an average sequence read length of the plurality of sequence reads is between 40 bases and 200 bases.

15. The sequencing method of claim 1, wherein
the plurality of sequence reads collectively provide at least 15× coverage for the nucleic acid, more than ten percent of the k-mers in the plurality of
k-mers are from more than one sequence read in the
plurality sequence reads, and the identifier of each sequence read for each k-mer
represented by more than one sequence read is retained.

16. The sequencing method of claim 1, wherein the plurality of sequence reads collectively provide at
least 25× coverage for the nucleic acid, more than thirty percent of the plurality of k-mers are
from more than one sequence read in the plurality
sequence reads, and the identifier of each sequence read for each k-mer
represented by more than one source sequence read is
retained.

17. The sequencing method of claim 1, wherein each sequence read in the plurality of sequence reads encodes between 75 and 125 bases of the nucleic acid and the value k is an odd integer between 5 and 73.

18. The sequencing method of claim 1, wherein a set of sequence reads in the plurality of sets of sequence reads comprises more than 100 sequence reads, and each sequence read of the more than 100 sequence reads includes the same common second portion.

19. The sequencing method of claim 1, wherein the nucleic acid is a chromosome, or is greater than 40 million base pairs in length.

20. The sequencing method of claim 1, wherein creating the respective set of k-mers comprises hashing each sequence read in the plurality of sequence reads according to a predetermined k-mer length thereby creating a respective set of k-mers for each sequence read in the plurality of sequence reads.

* * * * *